United States Patent
Nakamura et al.

(10) Patent No.: US 8,232,282 B2
(45) Date of Patent: Jul. 31, 2012

(54) COMPOUND HAVING BICYCLIC PYRIMIDINE STRUCTURE AND PHARMACEUTICAL COMPOSITION COMPRISING THE SAME

(75) Inventors: Keiji Nakamura, Suita (JP); Hiroyuki Nakagawa, Osaka (JP); Yoko Kan, Osaka (JP)

(73) Assignees: Dainippon Sumitomo Pharma Co., Ltd., Osaka (JP); Sumitomo Chemical Company, Limited, Tokyo (JP)

( * ) Notice: Subject to any disclaimer, the term of this patent is extended or adjusted under 35 U.S.C. 154(b) by 186 days.

(21) Appl. No.: 12/311,335

(22) PCT Filed: Sep. 28, 2007

(86) PCT No.: PCT/JP2007/068974
§ 371 (c)(1),
(2), (4) Date: Mar. 26, 2009

(87) PCT Pub. No.: WO2008/038768
PCT Pub. Date: Apr. 3, 2008

(65) Prior Publication Data
US 2010/0093771 A1 Apr. 15, 2010

(30) Foreign Application Priority Data
Sep. 28, 2006 (JP) .................... 2006-265965

(51) Int. Cl.
*A01N 43/00* (2006.01)
(52) U.S. Cl. .................... 514/264.1; 544/279
(58) Field of Classification Search ............... 514/264.1; 544/279
See application file for complete search history.

(56) References Cited

FOREIGN PATENT DOCUMENTS

| JP | 7-330768 | | 12/1995 |
|---|---|---|---|
| JP | 7-330769 | | 12/1995 |
| JP | 2006083085 A | * | 3/2006 |
| WO | 2005/082887 | | 9/2005 |
| WO | 2008/130581 | | 10/2008 |
| WO | 2008/130584 | | 10/2008 |

OTHER PUBLICATIONS

JP2006-083085, machine translation.*
Mockus et al The chemical abstracts service chemical registry system. VII. Tautomerism and alternating double bonds, J. Chem, Inf. Comput. Sci. 1980, vol. 20, pp. 18-22 i.*
Patani et al "Bioisosterism: a rational approach in drug design", Chem., Rev., 1996, vol. 96, No. 8, pp. 3147-3176.*
Schafer et al. Drug Discovery Today 2008, 13 (21/22), 913-916.*
Horig et al. Journal of Translational Medicine 2004, 2(44).*
, Fabian et al "Azabenzenes (Azines)-the nitrogen derivatives of benzene with one to six N atoms: stability, homodesmotic stabilization energy, electron distribution, and magnetic ring current; a computational study", Can. J. Chem, vol. 82, pp. 50-69, 2004.*
Extended European Search Report issued Oct. 14, 2009 in connection with corresponding European Application No. 07 82 8715.
Cao et al., "Cloning and Functional Characterization of a Mouse Intestinal Acyl-CoA:Monoacylglycerol Acyltransferase, MGAT2*" *The Journal of Biological Chemistry*, vol. 278, No. 16, pp. 13860-13866, 2003.
Cao et al., A Predominant Role of Acyl-CoA:monoacylglycerol Acyltransferase-2 in Dietary Fat Absorption Implicated by Tissue Distribution, Subcellular Localization, and Up-regulation by High Fat Diet*, *The Journal of Biological Chemistry*, vol. 279, No. 18, pp. 18878-18886, 2004.

* cited by examiner

*Primary Examiner* — Brandon Fetterolf
*Assistant Examiner* — Jean Cornet
(74) *Attorney, Agent, or Firm* — Wenderoth, Lind & Ponack, L.L.P.

(57) ABSTRACT

The present invention relates to a bicyclic pyrimidine compound of the following formula (I) or a salt thereof.

wherein $R^1$ is lower alkyl, cyclic lower alkyl. etc.; $R^2$ is H, lower alkyl, lower alkenyl, etc.; $R^3$ is H, lower alkyl, lower alkenyl, etc.; X is O, S or —N($R^4$)—; $R^4$ is H or lower alkyl; or $R^2$ and $R^4$ may combine each other to form cyclic amino; Y is amido, keto, sulfonyl, etc.; $R^5$ is H or lower alkyl; Z is O or S; m and n are 1 or 2. Said compound (I) or a salt thereof have MGAT inhibitory activity, and are useful as an agent for treatment or prophylaxis of adiposity, metabolic syndromes, hyperlipidemia, hyper neutral lipemia, hyper VLDL-mia, hyper fatty acidemia, diabetes mellitus, arteriosclerosis.

16 Claims, No Drawings

COMPOUND HAVING BICYCLIC PYRIMIDINE STRUCTURE AND PHARMACEUTICAL COMPOSITION COMPRISING THE SAME

This application is a U.S. national stage of International Application No. PCT/JP2007/068974, filed Sep. 28, 2007.

TECHNICAL FIELD

The present invention relates to a compound having a bicyclic pyrimidine structure and exhibiting an inhibitory activity of monoacylglycerol acyltransferase (hereinafter occasionally referred to as MGAT), and a pharmaceutical composition comprising the same.

BACKGROUND ART

Recently, the number of patients having so-called lifestyle-related diseases such as diabetes mellitus, hyperlipidemia, hypertension, etc. is drastically increasing. These diseases largely result from the fact that a condition of excessive accumulation of fatty tissues, i.e., obesity is increased in the modern society having hyperalimentation and the lack of exercise. Therefore, it is very important to treat/cure obesity. In Japan, obesity is considered as a disorder such as adiposity, and a guideline for positively diagnosing/treating adiposity has been published. That is, patients having a BMI (body mass index) of 25 or more, and further having a health disturbance caused by or relating to obesity, and requiring body weight control, for example, one of the diseases selected from type 2 diabetes mellitus/glucose intolerance, abnormal lipid metabolism, hypertension, hyperuricemia/gout, coronary arterial disease, cerebral infarction, sleep apnea syndrome, fatty liver, orthopedic diseases, and menstruation problems, are diagnosed as adiposity. In addition, patients having no such a health disturbance but patients with visceral fat-type obesity are also diagnosed as adiposity.

In the treatment of adiposity, diet therapy and exercise therapy are usually employed, but when the expected satisfactory effects are not obtained thereby, medication therapy is further employed. As an anti-obesity agent, fat absorption inhibitor, orlistat; central anorectic drug, mazindol, sibutramine, etc. have been known, but none of these drugs is sufficient enough in view of both of medicinal effect and side effects. Under these circumstances, it has been desired to develop a new more effective drug from viewpoint of medicinal effect and side effects.

Neutral fats taken from the diet (triglycerol (TG)) are decomposed by pancreatic lipase in the digestive tract into fatty acid and monoacylglycerol (MG), and form a micell, which is further absorbed into the small intestine epithelial cells. The absorbed fatty acid is further converted into acyl-CoA by acyl-CoA synthetase. Further, diacylglycerol (DG) is synthesized from MG and acyl-CoA by monoacylglycerol acyltransferase (MGAT), and further, TG is synthesized again from DG and acyl-CoA by diacylglycerol acyltransferase (DGAT). The synthesized TG associates with cholesterol ester and apo-protein by microsomal triglycerol transfer protein (MTP) to give chylomicron, which is secreted into the blood through lymph duct and transported into peripheral tissues.

As mentioned above, MGAT catalyzes the reaction of MG and acyl-CoA to produce DG, and plays an important role in the process of fat absorption at the small intestine. However, the purification of MGAT is quite difficult so that the study of MGAT has not been progressed yet, and the identification of gene thereof has been finally completed recently. Until now, three molecular species of MGAT (MGAT1, MGAT2, MGAT3) have been cloned and reported (Non-patent Documents 1 to 5). MGAT1 is expressed in the stomach and the kidney, but not expressed in the small intestine. On the other hand, MGAT2 is highly expressed in the small intestine. Further, the gene of MGAT3 has been reported only in human MGAT3, and expressed specifically in the small intestine. Therefore, it is speculated that MGAT2 and MGAT3 may participate in the fat absorption in the small intestine.

It has been reported that the MGAT activity in the small intestine is elevated in OLETF rats, which show obesity and hypertriglyceridemia, by which the involvement of MGAT with obesity and hypertriglyceridemia has been suggested (Non-patent Document 6). In addition, the increased protein amount of MGAT 2 and the elevated MGAT activity in the small intestine in db/db mice showing obesity, and in DIO (diet induced obesity) mice have been reported, and the involvement of MGAT with obesity is indicated (Non-patent Document 7).

Under these circumstances, the present inventors thought that the fat absorption at the small intestine may be suppressed by inhibiting the MGAT activity at the small intestine, which is effective to obesity, and further they intensively studied and finally found a MGAT-inhibitory compound having fat absorption inhibitory activity.

On the other hand, as a compound having a bicyclic pyrimidine structure, Patent Document 1 discloses 2-[2-(substituted amino)-benzylthio]-5,6,7,8-tetrahydropyrido[3,4-d]pyrimidine-4(3H)-one derivatives of the following Chemical formula 1, and Patent Document 2 discloses 2-[2-(substituted amino)benzylthio]-5,6,7,8-tetrahydropyrido-[4,3-d]pyrimidine-4(3H)-one derivatives of the following Chemical formula 2, but $R^1$ of these compounds is restricted to a hydrogen atom or a lower alkyl group. In addition, these compounds are disclosed to be useful as a peptic ulcer agent, but the MGAT inhibitory activity or fat absorption inhibitory activity thereof is not disclosed at all.

[Chemical formula 1]

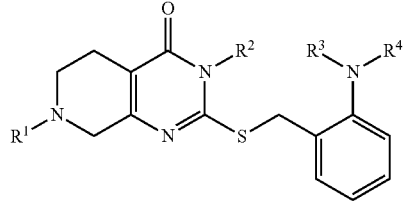

wherein $R^1$ and $R^2$ are a hydrogen atom or a lower alkyl group; and $R^3$ and $R^4$ are the same or different lower alkyl group.

[Chemical formula 2]

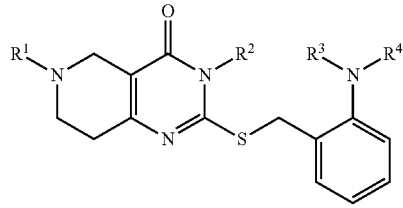

wherein R¹ is a hydrogen atom, a lower alkyl group, a hydroxyalkyl group or a lower alkoxyalkyl group; R² is a hydrogen atom or a lower alkyl group; R³ and R⁴ are the same or different lower alkyl group.

In addition, as a compound having a bicyclic pyrimidine structure, Non-patent document 8 discloses a compound of the following Chemical formula 3, but the substituent of the nitrogen atom of the piperidine nucleus is restricted to a benzyl group, and the pharmacological activities of these compounds have not been disclosed yet.

[Chemical formula 3]

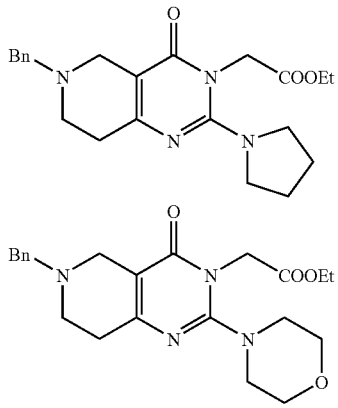

wherein Bn is a benzyl group, and Et is an ethyl group.
Patent document 1: JP-A-H07-330768
Patent document 2: JP-A-H07-330769
Non-patent document 1: Proceedings of the National Academy of Sciences, 99, 8512-8517, 2002
Non-patent document 2: Journal of Biological Chemistry, 278, 18532-18537, 2003
Non-patent document 3: Journal of Biological Chemistry, 278, 13860-13866, 2003
Non-patent document 4: American Journal of Physiology, 285, E927-E937, 2003
Non-patent document 5: Journal of Biological Chemistry, 278, 13611-13614, 2003
Non-patent document 6: Diabetes Research and Clinical Practice, 57, 75-82, 2002
Non-patent document 7: Journal of Biological Chemistry, 279, 18878-18886, 2004
Non-patent document 8: Heterocycles, 115-126, 2001

DISCLOSURE OF INVENTION

Problems to be Solved by Invention

An object of the present invention is to provide a compound having MGAT inhibitory activity and a pharmaceutically acceptable salt thereof.

Means for Solving the Problems

The present inventors intensively studied and found that the compound having a bicyclic pyrimidine structure of the following formula (I) and a pharmaceutically acceptable salt thereof exhibit MGAT inhibitory activity, and finally accomplished the present invention. Namely, the present invention provides the following inventions.

[1] A compound having a bicyclic pyrimidine structure of the following formula (I) or a pharmaceutically acceptable salt thereof.

[Chemical formula 4]

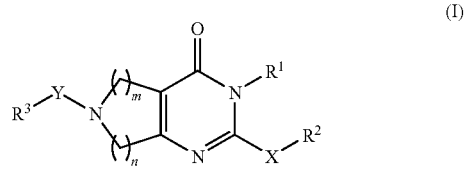

(I)

wherein R¹ is an optionally substituted lower alkyl group, an optionally substituted cyclic lower alkyl group, an optionally substituted cyclic lower alkenyl group, an optionally substituted phenyl group, an optionally substituted naphthyl group, or a saturated or unsaturated optionally substituted heterocyclic group, R² is a hydrogen atom, an optionally substituted lower alkyl group, an optionally substituted lower alkenyl group, an optionally substituted lower alkynyl group, an optionally substituted cyclic lower alkyl group, an optionally substituted cyclic lower alkenyl group, an optionally substituted lower alkanoyl group, an optionally substituted phenylcarbonyl group, an optionally substituted phenyl group, an optionally substituted naphthyl group, or a saturated or unsaturated optionally substituted heterocyclic group, R³ is a hydrogen atom, an optionally substituted lower alkyl group, an optionally substituted lower alkenyl group, an optionally substituted lower alkynyl group, an optionally substituted cyclic lower alkyl group, an optionally substituted cyclic lower alkenyl group, an optionally substituted phenyl group, an optionally substituted naphthyl group, or a saturated or unsaturated optionally substituted heterocyclic group, X is an oxygen atom, a sulfur atom, or —N(R⁴)—, R⁴ is a hydrogen atom or a lower alkyl group, or R² and R⁴ may combine each other to form a cyclic amino group, Y is the following (II), (III) or (IV):

[Chemical formula 5]

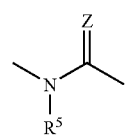

(II)

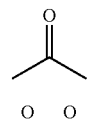

(III)

(IV)

R⁵ is a hydrogen atom or a lower alkyl group,
Z is an oxygen atom or a sulfur atom,
m and n are each an integer of 1 or 2.

[2] The compound of the above [1] or a pharmaceutically acceptable salt thereof, wherein m and n are different and each is an integer of 1 or 2.

[3] The compound of the above [1] or a pharmaceutically acceptable salt thereof, wherein X is a sulfur atom or —N($R^4$)— ($R^4$ is the same as defined in [1]).

[4] The compound of the above [1] or a pharmaceutically acceptable salt thereof, wherein Y is the following (II) or (III).

[Chemical formula 6]

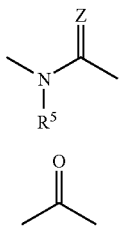

($R^5$ and Z are the same as defined in [1]).

[5] The compound of the above [1] or a pharmaceutically acceptable salt thereof, wherein in the formula (I), $R^1$ is a $C_{1-8}$ alkyl group, a cyclic $C_{3-8}$ alkyl group, a cyclic $C_{3-8}$ alkenyl group, a phenyl group, a naphthyl group, or a saturated or unsaturated heterocyclic group, $R^2$ is a hydrogen atom, a $C_{1-8}$ alkyl group, a $C_{2-8}$ alkenyl group, a $C_{2-8}$ alkynyl group, a cyclic $C_{3-8}$ alkyl group, a cyclic $C_{3-8}$ alkenyl group, a $C_{1-8}$ alkanoyl group, a phenylcarbonyl group, a phenyl group, a naphthyl group, or a saturated or unsaturated heterocyclic group, $R^3$ is a hydrogen atom, a $C_{1-8}$ alkyl group, a $C_{2-8}$ alkenyl group, a $C_{2-8}$ alkynyl group, a cyclic $C_{3-8}$ alkyl group, a cyclic $C_{3-8}$ alkenyl group, a phenyl group, a naphthyl group, or a saturated or unsaturated heterocyclic group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 7]

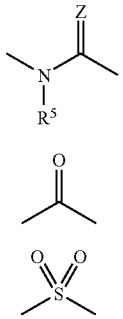

$R^5$ is a hydrogen atom or a $C_{1-8}$ alkyl group,

Z is an oxygen atom or a sulfur atom, m and n are an integer of 1 or 2, in which the above-mentioned alkyl, alkenyl, alkynyl and alkanoyl groups for $R^1$, $R^2$ and $R^3$ may be substituted by 1 to 3 substituents selected from a halogen atom, a cyclic $C_{3-8}$ alkyl group, a phenyl group, a phenyloxy group, a $C_{1-8}$ alkoxy group, a trifluoromethoxy group, a $C_{1-8}$ alkylthio group, a hydroxy group, a nitro group, a cyano group, a carboxyl group, a $C_{1-8}$ alkoxycarbonyl group, a benzyloxycarbonyl group, a carbamoyl group, a mono- or di-substituted $C_{1-8}$ alkylaminocarbonyl group, a cyclic aminocarbonyl group, an amino group, a mono- or di-substituted $C_{1-8}$ alkylamino group, a cyclic amino group, a $C_{1-8}$ alkylsulfonylamino group, a benzenesulfonylamino group, a $C_{1-8}$ alkanoylamino group, a benzoylamino group, a $C_{1-8}$ alkoxycarbonylamino group, a carbamoylamino group, a mono- or di-substituted $C_{1-8}$ alkylaminocarbonylamino group, a cyclic aminocarbonylamino group, a sulfamoyl group, a mono- or di-substituted $C_{1-8}$ alkylaminosulfonyl group, a cyclic aminosulfonyl group and a saturated or unsaturated heterocyclic group, When the above-mentioned alkyl group for $R^1$, $R^2$ and $R^3$ is substituted by a phenyl group, then said phenyl group may further be substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a $C_{1-8}$ alkylthio group, a nitro group, a cyano group, a carboxyl group, a $C_{1-8}$ alkoxycarbonyl group, a carbamoyl group, an amino group, a mono- or di-substituted $C_{1-8}$ alkylamino group, a $C_{1-8}$ alkanoylamino group, a carbamoylamino group and a sulfamoyl group, the above-mentioned cyclic alkyl, cyclic alkenyl, phenylcarbonyl, phenyl, naphthyl and saturated or unsaturated heterocyclic groups for $R^1$, $R^2$ and $R^3$ may be substituted by 1 to 3 substituents selected from a halogen atom, a $C_{1-8}$ alkyl group, a cyclic $C_{3-8}$ alkyl group, a phenyl group, a phenyloxy group, a $C_{1-8}$ alkoxy group, a trifluoromethyl group, a trifluoromethoxy group, a $C_{1-8}$ alkylthio group, a hydroxy group, a hydroxy-$C_{1-8}$ alkyl group, a nitro group, a cyano group, a carboxyl group, a $C_{1-8}$ alkoxycarbonyl group, a benzyloxycarbonyl group, a carbamoyl group, a mono- or di-substituted $C_{1-8}$ alkylaminocarbonyl group, a cyclic aminocarbonyl group, an amino group, a mono- or di-substituted $C_{1-8}$ alkylamino group, a cyclic amino group, a $C_{1-8}$ alkylsulfonylamino group, a benzenesulfonylamino group, a $C_{1-8}$ alkanoylamino group, a benzoylamino group, a $C_{1-8}$ alkoxycarbonylamino group, a carbamoylamino group, a mono- or di-substituted $C_{1-8}$ alkylaminocarbonylamino group, a cyclic aminocarbonylamino group, a sulfamoyl group, a mono- or di-substituted $C_{1-8}$ alkylaminosulfonyl group and a cyclic aminosulfonyl group.

[6] The compound of the above [5] or a pharmaceutically acceptable salt thereof, wherein in the formula (I), $R^1$ is a $C_{1-8}$ alkyl group, a cyclic $C_{3-8}$ alkyl group, a cyclic $C_{3-8}$ alkenyl group, a phenyl group, or a saturated or unsaturated heterocyclic group, $R^2$ is a $C_{1-8}$ alkyl group, a cyclic $C_{3-8}$ alkyl group, a phenyl group, or a saturated or unsaturated heterocyclic group, $R^3$ is a $C_{1-8}$ alkyl group, a $C_{2-8}$ alkenyl group, a cyclic $C_{3-8}$ alkyl group, a cyclic $C_{3-8}$ alkenyl group, a phenyl group, or a saturated or unsaturated heterocyclic group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 8]

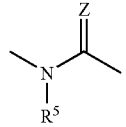

-continued (III)

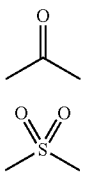

(IV)

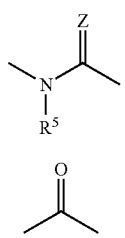

$R^5$ is a hydrogen atom or a $C_{1-8}$ alkyl group,

Z is an oxygen atom or a sulfur atom, m and n are an integer of 1 or 2, in which the above-mentioned alkyl and alkenyl groups for $R^1$, $R^2$ and $R^3$ may be substituted by 1 to 3 substituents selected from a halogen atom, a phenyl group, a phenyloxy group, a $C_{1-8}$ alkoxy group, a trifluoromethoxy group, a cyano group, a carboxyl group, a carbamoyl group, an amino group, a mono- or di-substituted $C_{1-8}$ alkylamino group, a $C_{1-8}$ alkanoylamino group, a sulfamoyl group and a saturated or unsaturated heterocyclic group, When the above-mentioned alkyl group for $R^1$, $R^2$ and $R^3$ is substituted by a phenyl group, then said phenyl group may be further substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, the above-mentioned cyclic alkyl, cyclic alkenyl, phenyl and saturated or unsaturated heterocyclic groups for $R^1$, $R^2$ and $R^3$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group.

[7] The compound of the above [6] or a pharmaceutically acceptable salt thereof, wherein in the formula (I), $R^1$ is a $C_{1-8}$ alkyl group, a cyclic $C_{3-8}$ alkyl group, a phenyl group, or a saturated or unsaturated heterocyclic group, $R^2$ is a $C_{1-8}$ alkyl group, a cyclic $C_{3-8}$ alkyl group, or a phenyl group, $R^3$ is a $C_{1-8}$ alkyl group, a cyclic $C_{3-8}$ alkyl group, a phenyl group, or a saturated or unsaturated heterocyclic group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 9]

(II)

(III)

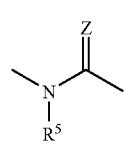

(IV)

$R^5$ is a hydrogen atom or a $C_{1-8}$ alkyl group,

Z is an oxygen atom or a sulfur atom, m and n are an integer of 1 or 2, in which the above-mentioned alkyl group for $R^1$, $R^2$ and $R^3$ may be substituted by 1 to 3 substituents selected from a halogen atom, a phenyl group, a phenyloxy group, a $C_{1-8}$ alkoxy group, a trifluoromethoxy group, a cyano group, a carboxyl group, a carbamoyl group, an amino group, a mono- or di-substituted $C_{1-8}$ alkylamino group, a $C_{1-8}$ alkanoylamino group, a sulfamoyl group and a saturated or unsaturated heterocyclic group, When the above-mentioned alkyl group for $R^1$, $R^2$ and $R^3$ is substituted by a phenyl group, then said phenyl group may be further substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, the above-mentioned cyclic alkyl, phenyl and saturated or unsaturated heterocyclic groups for $R^1$, $R^2$ and $R^3$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group.

[8] The compound of the above [5] or a pharmaceutically acceptable salt thereof, wherein m and n are different and each is an integer of 1 or 2.

[9] The compound of the above [5] or a pharmaceutically acceptable salt thereof, wherein X is a sulfur atom or —N($R^4$)— ($R^4$ is the same as defined in [5]).

[10] The compound of the above [5] or a pharmaceutically acceptable salt thereof, wherein Y is the following (II) or (III):

[Chemical formula 10]

($R^5$ and Z are the same as defined in [5])

[11] The compound of the above [6] or a pharmaceutically acceptable salt thereof, wherein m and n are different, and each is an integer of 1 or 2.

[12] The compound of the above [6] or a pharmaceutically acceptable salt thereof, wherein X is a sulfur atom or —N($R^4$)— ($R^4$ is the same as defined in [6]).

[13] The compound of the above [6] or a pharmaceutically acceptable salt thereof, wherein Y is the following (II) or (III):

[Chemical formula 11]

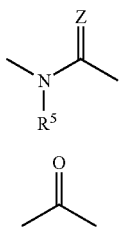

($R^5$ and Z are the same as defined in [6]).

[14] The compound of the above [7] or a pharmaceutically acceptable salt thereof, wherein m and n are different, and each is an integer of 1 or 2.

[15] The compound of the above [7] or a pharmaceutically acceptable salt thereof, wherein X is a sulfur atom or —N($R^4$)— ($R^4$ is the same as defined in [7]).

[16] The compound of the above [7] or a pharmaceutically acceptable salt thereof, wherein Y is the following (II) or (III):

[Chemical formula 12]

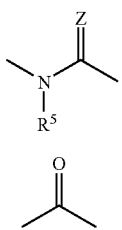

($R^5$ and Z are the same as defined in [7]).

[17] A pharmaceutical composition containing a compound as set forth in any one of the above [1] to [16] or a pharmaceutically acceptable salt thereof.

[18] An MGAT inhibitor containing as the active ingredient a compound as set forth in any one of the above [1] to [16] or a pharmaceutically acceptable salt thereof.

[19] A fat absorption inhibitor containing as the active ingredient a compound as set forth in any one of the above [1] to [16] or a pharmaceutically acceptable salt thereof.

[20] An agent for treatment or prophylaxis of adiposity, metabolic syndromes, hyperlipidemia, hyper neutral lipemia, hyper VLDL-mia, hyper fatty acidemia, diabetes mellitus, arteriosclerosis, which comprises as the active ingredient a compound as set forth in any one of the above [1] to [16] or a pharmaceutically acceptable salt thereof.

The pharmaceutically acceptable salt includes a pharmaceutically acceptable acid addition salt, an alkali metal salt, an alkaline earth metal salt or a salt with an organic base. Examples of the acid addition salt are a salt with an inorganic acid such as hydrochloride, hydrobromate, hydroiodide, sulfate, phosphate, and a salt with an organic acid such as oxalate, maleate, fumarate, malonate, lactate, malate, citrate, tartrate, benzoate, methanesulfonate, p-toluene-sulfonate, gluconate, etc. The alkali metal salt includes, for example, an inorganic alkali metal salt such as sodium salt, potassium salt, etc. and the alkaline earth metal salt includes, for example, calcium salt, magnesium salt, etc. In addition, the salt with an organic base includes, for example, a salt with ammonia, methylamine, triethylamine, N-methylmorpholine.

The compound of the formula (I) and a pharmaceutically acceptable salt thereof may exist in the form of hydrate and/or solvate thereof, and these hydrates and solvates are also included in the present compounds.

Further, the compound of the formula (I) may have one or more asymmetric carbon atom(s) and give a geometric isomerization or axial chirality based thereon, by which the present compound may exist in the form of several stereoisomers. These stereoisomers or a mixture thereof or racemic compounds are also included in the present compounds.

The terms used in the present specification are explained below.

The lower alkyl group and the lower alkyl moiety mean a straight chain or branched chain alkyl group having 1 to 8 carbon atoms, and include, for example, methyl, ethyl, propyl, isopropyl, butyl, isobutyl, sec-butyl, tert-butyl, pentyl, isopentyl, tert-pentyl, hexyl, isohexyl, octyl.

The cyclic lower alkyl group means a cyclic alkyl group having 3 to 8 carbon atoms, and includes, for example, cyclopropyl, cyclobutyl, cyclopentyl, cyclohexyl, cycloheptyl, cyclooctyl.

The lower alkoxy group and the lower alkoxy moiety mean a straight chain or branched chain alkoxy group having 1 to 8 carbon atoms, and include, for example, methoxy, ethoxy, propoxy, isopropoxy, butoxy, isobutoxy, sec-butoxy, tert-butoxy.

The lower alkylthio group means a group wherein a sulfur atom is attached to the binding site of a straight chain or branched chain alkyl group having 1 to 8 carbon atom, and includes, for example, methylthio, ethylthio, propylthio, isopropylthio, butylthio, isobutylthio, sec-butylthio, tert-butylthio.

The lower alkenyl group means a carbon chain where at least one carbon-carbon bond of a lower alkyl group having 2 to 8 carbon atoms is replaced by a double bond, and includes, for example, vinyl, allyl, 3-butenyl, isobutenyl, 1,4-heptandienyl.

The cyclic lower alkenyl group means a carbon chain where one or two carbon-carbon bond(s) of a cyclic lower alkyl group having 3 to 8 carbon atoms are replaced by a double bond, and includes, for example, cyclopropenyl, cyclobutenyl, cyclopentenyl, cyclohexenyl, cycloheptenyl, cyclooctenyl.

The lower alkynyl group means a carbon chain where at least one carbon-carbon bond of a lower alkyl group having 2 to 8 carbon atoms is replaced by a triple bond, and includes, for example, ethynyl, propargyl, 2-butynyl, 3-butynyl, 4-heptynyl.

The halogen atom means fluorine, chlorine, bromine, iodine.

The cyclic amino group and the cyclic amino moiety mean a 4- to 7-membered cyclic amine containing at least one nitrogen atom and further optionally containing an oxygen atom and a sulfur atom, or a 4- to 7-membered cyclic amine containing at least one nitrogen atom condensed with a benzene ring and further optionally containing an oxygen atom and a sulfur atom, and include, for example, azethydinyl, pyrrolidyl, piperidyl, morpholyl, thiomorpholyl, hexahydroazepinyl, tetrahydroquinolyl, tetrahydroisoquinolyl, indolyl, isoindolyl, 1-oxoisoindolyl, 1,3-dioxoisoindolyl.

The lower alkanoyl group and the lower alkanoyl moiety mean a straight chain or branched chain alkanoyl group having 1 to 8 carbon atoms, and include, for example, formyl, acetyl, propionyl, butyryl, isobutyryl, valeryl, pivaloyl.

The saturated or unsaturated heterocyclic group means a saturated or unsaturated 5- or 6-membered heterocyclic group having 1 to 4 heteroatoms selected from an oxygen atom, a sulfur atom and a nitrogen atom, or a saturated or unsaturated 5- or 6-membered heterocyclic group containing 1 to 4 heteroatoms selected from an oxygen atom, a sulfur atom and a nitrogen atom, which is condensed with a benzene ring, and includes, for example, pyrrolyl, furanyl, thienyl, furyl, imidazolyl, oxazolyl, thiazolyl, oxadiazolyl, pyridyl, pyrimidyl, pyrazyl, pyrazolyl, indolyl, isoxazolyl, isothiazolyl, imidazolyl, oxazolyl, thiazolyl, triazolyl, indazolyl, benzofuranyl, benzodiaoxazolyl, benzo-thienyl, benzothiazolyl, benzoimidazolyl, benzoxazolyl, benzothiazolyl, quinolyl, isoquinolyl.

The optionally substituted lower alkyl group means a lower alkyl group optionally substituted by 1 to 3 substituents selected from a halogen atom, a cyclic lower alkyl group; a phenyl group, a phenyloxy group, a lower alkoxy group, a trifluoromethoxy group, a lower alkylthio group, a hydroxy group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonylamino group, a lower alkanoylamino group, a benzoylamino group, a lower alkoxycarbonylamino group, a carbamoylamino group, a mono- or di-substituted lower alkylaminocarbonyl-amino group, a cyclic aminocarbonylamino group, a sulfamoyl group, a mono- or di-substituted lower alkylaminosulfonyl group, a cyclic aminosulfonyl group and a saturated or unsaturated heterocyclic group, and includes, for example, methyl, ethyl, propyl, isopropyl, butyl, isobutyl, sec-butyl, tert-butyl, chloromethyl, methoxymethyl, 2-methoxyethyl, cyclopropylmethyl, benzyldiphenylmethyl, benzyl, phenethyl, 3-phenylpropyl, 4-phenylbutyl, hydroxymethyl, methoxy-carbonylmethyl, hydroxycarbonylmethyl, carbamoylmethyl, 2-chloro-ethyl, 2-bromoethyl, 2,2-dichloroethyl, 2,2,2-trifluoroethyl, 2-amino-ethyl, 3-chloropropyl, 3-nitropropyl, 3-cyanopropyl, 3-(methylamino)-propyl, 3-(dimethylamino)propyl, 3-(1-pyrrolidyl) propyl, cyclohexylmethyl, phenylmethyl, phenylethyl, 2-, 3- or 4-methylphenylmethyl, 2-, 3- or 4-methoxyphenylmethyl, 2-, 3- or 4-chlorophenylmethyl, 2-, 3- or 4-fluorophenylmethyl, 3-aminophenylmethyl, 3-dimethylaminophenylmethyl, 3-acetylaminophenylmethyl, 3-carboxyphenylmethyl, 2-, 3- or 4-pyridylmethyl, 5-benzodioxalylmethyl, 2-thienylmethyl, 2-furylmethyl.

The optionally substituted cyclic lower alkyl group means a cyclic lower alkyl group optionally substituted by 1 to 3 substituents selected from a halogen atom, a lower alkyl group, a cyclic lower alkyl group, a phenyl group, a phenyloxy group, a lower alkoxy group, a trifluoromethyl group, a trifluoromethoxy group, a lower alkylthio group, a hydroxy group, a hydroxy-lower alkyl group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzene-sulfonylamino group, a lower alkanoylamino group, a benzoylamino group, a lower alkoxycarbonylamino group, a carbamoylamino group, a mono- or di-substituted lower alkylaminocarbonylamino group, a cyclic aminocarbonylamino group, a sulfamoyl group, a mono- or di-substituted lower alkylaminosulfonyl group and a cyclic aminosulfonyl group, and includes, for example, 2- or 3-methylcyclopentyl, 2- or 3-fluorocyclohexyl, 2-, 3- or 4-methylcyclohexyl, 2-, 3- or 4-fluorocyclohexyl, 2-, 3- or 4-chlorocyclohexyl, 4,4-dimethylcyclohexyl, 2- or 3-methoxycyclohexyl.

The optionally substituted lower alkenyl group means a lower alkenyl group optionally substituted by 1 to 3 substituents selected from a halogen atom, a cyclic lower alkyl group, a phenyl group, a phenyloxy group, a lower alkoxy group, a trifluoromethoxy group, a lower alkylthio group, a hydroxy group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonylamino group, a lower alkanoylamino group, a benzoylamino group, a lower alkoxycarbonyl-amino group, a carbamoylamino group, a mono- or di-substituted lower alkylaminocarbonylamino group, a cyclic aminocarbonylamino group, a sulfamoyl group, a mono- or di-substituted lower alkylaminosulfonyl group, a cyclic aminosulfonyl group and a saturated or unsaturated heterocyclic group, and includes, for example, styryl, 2- or 3-phenylpropenyl, 3-phenylallyl, 4-(fluoro)styryl, 4-(methyl)styryl, 4-(methoxy)-styryl, 4-(trifluoromethyl)styryl, 3-(4-fluoro)phenylpropenyl, 3-(4-methyl)phenylpropenyl, 3-(4-methoxy) phenylpropenyl, 3-(4-trifluoromethyl)phenylpropenyl.

The optionally substituted cyclic lower alkenyl group means a cyclic lower alkenyl group optionally substituted by 1 to 3 substituents selected from a halogen atom, a lower alkyl group, a cyclic lower alkyl group, a phenyl group, a phenyloxy group, a lower alkoxy group, a trifluoromethyl group, a trifluoromethoxy group, a lower alkylthio group, a hydroxy group, a hydroxy-lower alkyl group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonyl-amino group, a lower alkanoylamino group, a benzoylamino group, a lower alkoxycarbonylamino group, a carbamoylamino group, a mono- or di-substituted lower alkylaminocarbonylamino group, a cyclic amino-carbonylamino group, a sulfamoyl group, a mono- or di-substituted lower alkylaminosulfonyl group and a cyclic aminosulfonyl group, and includes, for example, 2-methylcyclohexen-2-yl, 3-methylcyclohexen-2-yl, 4-methylcyclohexen-2-yl, 4-methylcyclohexen-3-yl, 4,4-dimethylcyclohexen-2-yl.

The optionally substituted lower alkynyl group means a lower alkynyl group optionally substituted by 1 to 3 substituents selected from a halogen atom, a cyclic lower alkyl group, a phenyl group, a phenyloxy group, a lower alkoxy group, a trifluoromethoxy group, a lower alkylthio group, a hydroxy group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonylamino group, a lower alkanoylamino group, a benzoylamino group, a lower alkoxycarbonyl-amino group, a carbamoylamino group, a mono- or di-substituted lower alkylaminocarbonylamino group, a cyclic aminocarbonylamino group, a sulfamoyl group, a mono- or di-substituted lower alkylaminosulfonyl group, a cyclic aminosulfonyl group and a saturated or unsaturated heterocyclic group, and includes, for example, phenylethynyl, phenyl-propy-1-nyl, 4-(fluoro)phenylethynyl, 4-(methyl)phenylethynyl.

The optionally substituted lower alkanoyl group means a lower alkanoyl group optionally substituted by 1 to 3 substituents selected from a halogen atom, a cyclic lower alkyl group, a phenyl group, a phenyloxy group, a lower alkoxy group, a trifluoromethoxy group, a lower alkylthio group, a hydroxy group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonylamino group, a lower alkanoylamino group, a benzoylamino group, a lower alkoxycarbonyl-amino group, a carbamoylamino group, a mono- or di-substituted lower alkylaminocarbonylamino group, a cyclic aminocarbonylamino group, a sulfamoyl group, a mono- or di-substituted lower alkylaminosulfonyl group, a cyclic aminosulfonyl group and a saturated or unsaturated heterocyclic group, and includes, for example, trifluoroacetyl, trichloroacetyl, methoxycarbonyl, ethoxycarbonylmethoxyacetyl, cyclopentanoyl, cyclopentenoyl, cyclohexanoyl, cyclohexenoyl.

The optionally substituted phenyl group and the optionally substituted phenyl moiety mean a phenyl group optionally substituted by 1 to 3 substituents selected from a halogen atom, a lower alkyl group, a phenyl group, a phenyloxy group, a lower alkoxy group, a trifluoromethyl group, a trifluoromethoxy group, a lower alkylthio group, a hydroxy group, a hydroxy-lower alkyl group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonyl-amino group, a lower alkanoylamino group, a benzoylamino group, a lower alkoxycarbonylamino group, a carbamoylamino group, a mono- or di-substituted lower alkylaminocarbonylamino group, a cyclic amino-carbonylamino group, a sulfamoyl group, a mono- or di-substituted lower alkylaminosulfonyl group and a cyclic aminosulfonyl group, and include, for example, phenyl, 2-, 3- or 4-chlorophenyl, 2-, 3- or 4-bromophenyl, 2-, 3- or 4-fluorophenyl, 2,4-dichlorophenyl, 2,5-dichlorophenyl, 3,4-dichlorophenyl, 3,5-dichlorophenyl, 2,3-dibromophenyl, 2,4-difluorophenyl, 2,5-difluorophenyl, 3,4-difluorophenyl, 3,5-difluorophenyl, 3-chloro-2-fluorophenyl, 4-chloro-2-fluorophenyl, 3-chloro-4-fluorophenyl, 2-, 3- or 4-methylphenyl, 2-chloro-4-methylphenyl, 2-chloro-5-methylphenyl, 2-fluoro-5-methylphenyl, 3-chloro-4-methylphenyl, 3-fluoro-4-methylphenyl, 4-chloro-2-methylphenyl, 5-chloro-2-methylphenyl, 5-fluoro-2-methylphenyl, 4-fluoro-3-methylphenyl, 2-, 3- or 4-methoxyphenyl, 5-chloro-2-methoxyphenyl, 3-chloro-4-methoxyphenyl, 2-, 3- or 4-aminophenyl, 4-methylaminophenyl, 2-, 3- or 4-trifluoromethylphenyl, 2-chloro-4-trifluoromethylphenyl, 2-fluoro-3-trifluoromethylphenyl, 3-fluoro-5-trifluoromethylphenyl, 4-chloro-2-trifluoromethylphenyl, 4-fluoro-2-trifluoromethylphenyl, 4-chloro-3-trifluoromethylphenyl, 4-fluoro-3-trifluoromethylphenyl, 3-dimethylaminophenyl, 2-, 3- or 4-cyanophenyl, 2-, 3- or 4-nitrophenyl, 4-biphenyl, 2-, 3- or 4-trifluoromethoxyphenyl, 4-ethylthiophenyl, 2-, 3- or 4-hydroxyphenyl, 4-hydroxymethylphenyl, 2-, 3- or 4-carboxylphenyl, 4-methoxycarbonylphenyl, 2-(methanesulfonylamino)phenyl, 4-(benzenesulfonylamino)phenyl, 2-, 3- or 4-(acetylamino)phenyl, 4-(benzoylamino)phenyl, 4-(ethoxycarbonylamino)phenyl, phenyloxy-phenyl.

The optionally substituted naphthyl group means a naphthyl group optionally substituted by 1 to 3 substituents selected from a halogen atom, a lower alkyl group, a phenyl group, a phenyloxy group, lower alkoxy group, a trifluoromethyl group, a trifluoromethoxy group, a lower alkylthio group, a hydroxy group, a hydroxy-lower alkyl group, a nitro group, a cyano group, a carboxyl group, a lower alkoxycarbonyl group, a benzyloxycarbonyl group, a carbamoyl group, a mono- or di-substituted lower alkylaminocarbonyl group, a cyclic aminocarbonyl group, an amino group, a mono- or di-substituted lower alkylamino group, a cyclic amino group, a lower alkylsulfonylamino group, a benzenesulfonylamino group, a lower alkanoylamino group, a benzoylamino group, a lower alkoxycarbonylamino group, a carbamoylamino group, a mono- or di-substituted lower alkylaminocarbonylamino group, a cyclic aminocarbonylamino group, a sulfamoyl group, a mono- or di-substituted lower alkylaminosulfonyl group and a cyclic aminosulfonyl group, and includes, for example, naphthyl, 2-, 3-, 4-, 5-, 6-, 7- or 8-chloronaphthyl, 2-, 3-, 4-, 5-, 6-, 7- or 8-methylnaphthyl, 2-, 3-, 4-, 5-, 6-, 7- or 8-methoxynaphthyl, 6,7-dibromo-2-naphthyl, 3-acetylaminolnaphthyl.

The saturated or unsaturated optionally substituted heterocyclic group means a heterocyclic group optionally substituted by 1 to 3 substituents selected from ones as described above for the optionally substituted phenyl group, and includes, for example, in addition to the above-mentioned saturated or unsaturated heterocyclic groups, 2-chloro-3-thienyl, 3-methyl-2-thienyl, 2-methyl-3-indolyl, 4-methylamino-3-pyridyl, 6-cyano-2-isoquinolyl.

The mono- or di-substituted lower alkylamino group and the mono- or di-substituted lower alkylamino moiety mean an amino group substituted by 1 or 2 lower alkyl group(s), and include, for example, methylamino, dimethylamino, ethylamino, diethylamino.

The methods of preparing the present compounds are explained below. The compounds of the present invention of the formula (I) may be prepared, for example, by the following Methods A to D.

In the following each step, when the starting compounds have a function group having possibilities of participating in the reaction within the structure thereof, i.e., an amino group, a carboxyl group, a hydroxy group, a carbonyl group, etc., then these groups may be protected by inserting a protecting group being conventionally used for these groups, and in such cases, the desired compounds can be obtained by suitably removing said protecting groups.

When the protection or de-protection procedure is needed in the following each step, such procedures can be carried out by a conventional method, for example, by the methods disclosed in Protective Groups in Organic Synthesis (written by Theodora W. Greene, Peter G. M. Wuts, published by John Wiley & Sons, Inc. 1999).

The protecting group for amino group, the protecting group for hydroxy group and the protecting group for carboxyl group are ones which can be easily removed by a method being usually used in the organic chemistry, such as reduction or hydrolysis, for example, in addition to the protecting groups disclosed in Protective Groups in Organic Synthesis (written by Theodora W. Greene, Peter G. M. Wuts, published by John Wiley & Sons, Inc., 1999), any substituents which can be removed enzymatically or non-enzymatically in the living body.

The protecting group for amino group includes, for example, methoxycarbonyl group, ethoxycarbonyl group, 2,2,2-trichloroethoxy-carbonyl group, isobutoxycarbonyl group, allyloxycarbonyl group, tert-butoxycarbonyl group, benzyloxycarbonyl group, vinyloxycarbonyl group, 9-fluorenylmethoxycarbonyl group, formyl group, acetyl group, propionyl group, benzoyl group, trifluoroacetyl group, p-toluenesulfonyl group, benzenesulfonyl group, methanesulfonyl group, benzyl group, diphenylmethyl group, triphenylmethyl group, pivaloyloxymethyl group, acetoxymethyl group, acetoxymethoxycarbonyl group, 1-acetoxyethoxycarbonyl group and alanyl group.

The protecting group for hydroxy group include, for example, in addition to methyl group, ethyl group, isopropyl group, tert-butyl group, allyl group, benzyl group, diphenylmethyl group, triphenylmethyl group, methoxymethyl group, methoxyethoxymethyl group, tetrahydropyranyl group, phenacyl group, acetyl group, propionyl group, pivaloyl group, benzoyl group, carbamoyl group, methoxycarbonyl group, ethoxycarbonyl group, 2,2,2-trichloroethoxycarbonyl group, allyloxycarbonyl group, isobutoxycarbonyl group, tert-butoxycarbonyl group and benzyloxycarbonyl group, further includes silyl protecting groups such as tert-butyldimethylsilyl group, tert-butyldiphenylsilyl group, triethylsilyl group, etc.

The protecting group for carboxyl group includes, for example, methyl group, ethyl group, isopropyl group, tert-butyl group, methyloxymethyl group, ethyloxymethyl group, allyl group, benzyl group, p-methyloxybenzyl group, p-nitrobenzyl group and benzhydryl group.

Method A

Among the compounds of the formula (I), the compound of the formula (I) wherein X is —N($R^4$)— ($R^4$ is the same as defined in [1]), Y is a group of the following formula (II):

[Chemical formula 13]

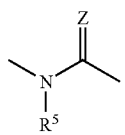

($R^5$ is the same as defined in [1]), i.e., the compound of the formula [A] may be prepared, for example, by the following method.

[Chemical formula 14]

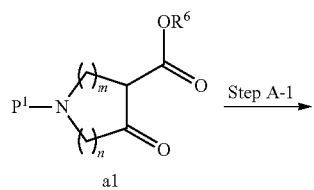

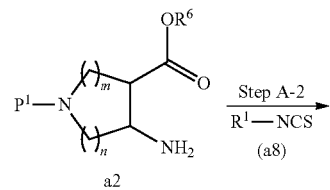

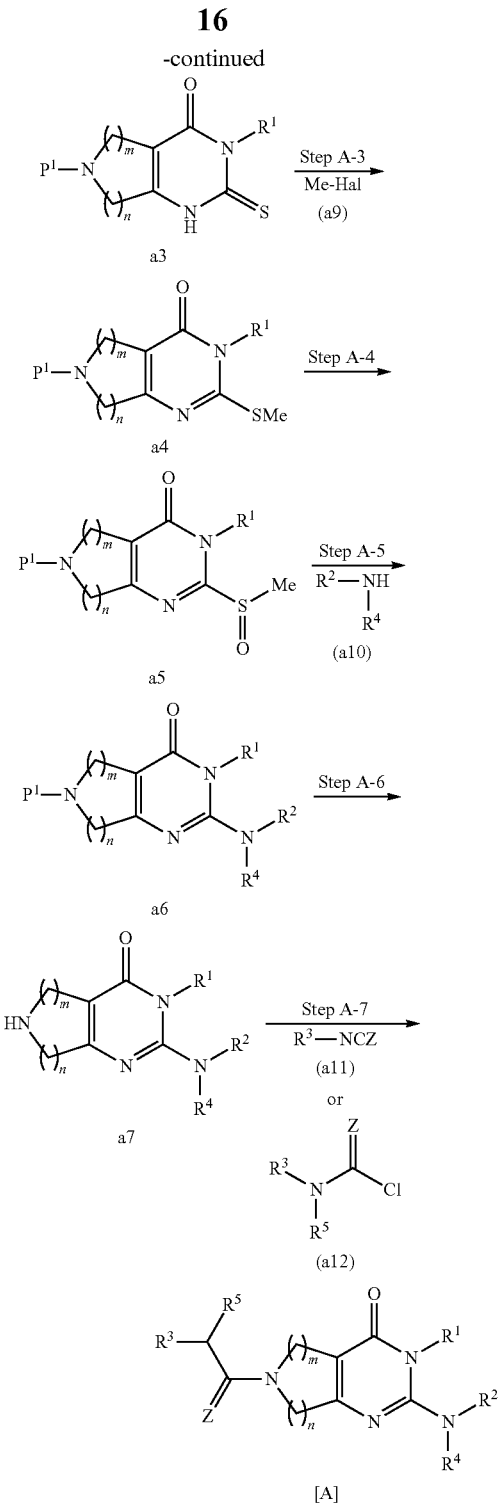

(wherein $R^1$ to $R^5$, Z, m, n are the same as defined in [1]; $P^1$ is a protecting group for amino group; $R^6$ is a lower alkyl group; Me is methyl group; and Hal is a halogen atom)

[Step A-1]

The present step is a step for obtaining Compound a2 by reacting Compound a1 with ammonia in a suitable solvent. The solvent used in this step may be selected from ones as exemplified below, and the preferable solvent is methanol or water.

[Step A-2]

This step is a step for obtaining Compound a3 by reacting Compound a2 obtained in the above Step A-1 with Compound a8. This step is carried out by the method disclosed in Heterocycles, 55 (2001), 115-126 or the method disclosed in Reference Example 2 as described hereinafter, or a modified method thereof.

[Step A-3]

This step is a step for obtaining Compound a4 by reacting Compound a3 obtained in the above Step A-2 with methyl halide (a9) in the presence of various bases in a suitable solvent. The base used in this step is selected from bases exemplified hereinafter, and the preferable base is 1,8-diazabicyclo[5.4.0]-7-undecene (DBU).

The solvent used in this step is selected from the solvents exemplified hereinafter, and the preferable solvent is N,N-dimethylformamide (DMF).

[Step A-4]

This step is a step for obtaining Compound a5 by reacting Compound a4 obtained in the above Step A-3 with various oxidizing agents in a suitable solvent. The oxidizing agent used in this step includes, for example, m-chloroperbenzoic acid, hydrogen peroxide, etc., and the preferable oxidizing agent is m-chloroperbenzoic acid.

The solvent used in this step is selected from the solvents exemplified hereinafter, and the preferable solvent is methylene chloride.

[Step A-5]

This step is a step for obtaining Compound a6 by reacting Compound a5 obtained in the above Step A-4 with Compound a10 in the presence of various bases in a suitable solvent. The base used in this step is selected from the bases exemplified hereinafter, and the preferable base is diisopropylethylamine, 4-dimethylaminopyridine (DMAP). The solvent used in this step is selected from the solvents exemplified hereinafter, and the preferable solvent is dioxane.

[Step A-6]

This step is a step for obtaining Compound a7 by removing the protecting group for amino group: $P^1$, of Compound a6 obtained in the above Step A-5. This step is carried out by the method disclosed in Protective Groups in Organic Synthesis (written by Theodora W. Greene, Peter G. M. Wuts, published by John Wiley & Sons, Inc., 1999) or a modified method thereof.

[Step A-7]

This step is a step for obtaining the compound of the formula [A] by reacting Compound a7 obtained in the above Step A-6 with Compound a11 or Compound a12 in the presence or absence of various bases in a suitable solvent, followed by removing the protecting group(s) for amino, hydroxy or carboxyl group for $R^1$ to $R^5$. The bases used in this step are selected from the bases exemplified hereinafter, and the preferable base is diisopropylethylamine. The solvents used in this step are selected from the solvents exemplified hereinafter, and the preferable one is tetrahydrofuran.

When $R^2$ is an optionally substituted lower alkanoyl group or an optionally substituted phenylcarbonyl group, then Compound a6 may be prepared, for example, by the following process.

[Chemical formula 15]

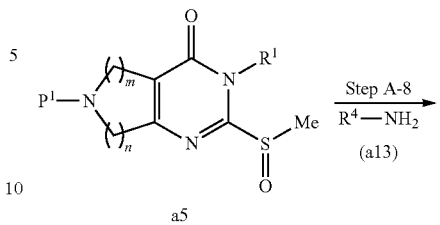

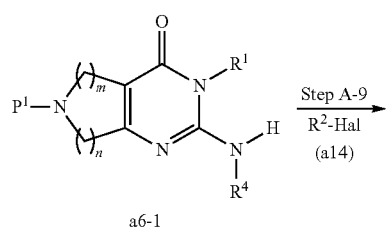

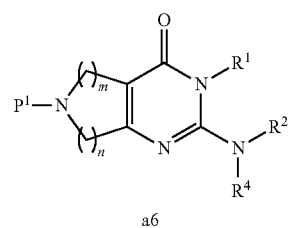

(wherein $R^1$, $R^2$, $R^4$, m, n are the same as defined in [1]; $P^1$, Me, Hal are the same as defined above)

[Step A-8]

This step is a step for obtaining Compound a6-1 by reacting Compound a5 obtained in the above Step A-4 with Compound a13 in a suitable solvent. The solvents used in this step are selected from ones as exemplified hereinafter, and the preferable one is dioxane.

[Step A-9]

This step is a step for obtaining Compound a6 by reacting Compound a6-1 obtained in the above Step A-8 with Compound a14 in the presence of various bases in a suitable solvent. The bases used in this step are selected from ones as exemplified hereinafter, and the preferable one is diisopropylethylamine. The solvents used in this step are selected from ones exemplified hereinafter, and the preferable one is tetrahydrofuran.

Method B

Among the compounds of the formula (I), the compound of the formula (I) wherein X is —N($R^4$)— ($R^4$ is the same as defined in [1]) and Y is a group of the following formula (III):

[Chemical formula 16]

(III)

i.e., the compound of the formula [B] may be prepared, for example, by the following method.

[Chemical formula 17]

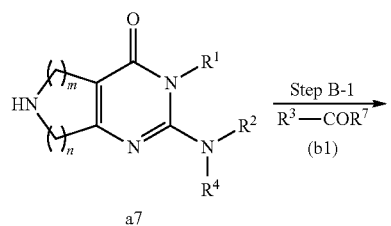

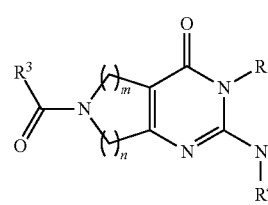

(wherein $R^1$ to $R^4$, m, n are the same as defined in [1]; $R^7$ is a halogen atom or a hydroxy group)

[Step B-1]

This step is a step for obtaining the compound of the formula [B] by reacting Compound a7 obtained in the above Step A-6 with Compound b1, if necessary, followed by removing a protecting group for amino group, hydroxy group or carboxyl group for $R^1$ to $R^4$. When $R^7$ is a halogen atom, then the compound of the formula [B] may be prepared by reacting Compound b1 in the presence of various bases in a suitable solvent. The bases used in this step are selected from ones exemplified hereinafter, and the preferable one is diisopropylethylamine. The solvents used in this step are selected from ones exemplified hereinafter, and the preferable one is methylene chloride.

When $R^7$ is a hydroxy group, the compound of the formula [B] may be prepared by reacting Compound b1 in the presence of various condensing agents in a suitable solvent. The condensing agents used in this step are, for example, dicyclohexylcarbodiimide (DCC), 1-ethyl-3-(3-dimethylaminopropyl)carbodiimide (WSC) (including hydrochloride thereof), N,N-carbonyldiimidazole (CDI), etc., and when dicyclohexyl-carbodiimide or 1-ethyl-3-(3-dimethylaminopropyl) carbodiimide hydrochloride is used, then said reaction is carried out by adding N-hydroxysuccinimide, 1-hydroxybenzotriazole, etc.

When $R^7$ is a hydroxy group, the compound of the formula [B] can also be prepared by activating Compound b1 by a conventional activation method of various carboxylic acids, followed by reacting with Compound a7. The activation method of carboxylic acid includes, for example, converting into an acid chloride with thionyl chloride, oxazolyl chloride, etc.; converting into an active ester with p-nitrobenzoyl chloride, 2,4,6-trichlorobenzoyl chloride, etc.

Method C

Among the compounds of the formula (I), the compound of the formula (I) wherein X is —N($R^4$)— ($R^4$ is the same as defined in [1]) and Y is a group of the following formula (IV)]

[Chemical formula 18]

i.e., the compound of the formula [C] may be prepared, for example, by the following method.

[Chemical formula 19]

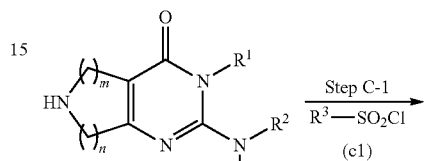

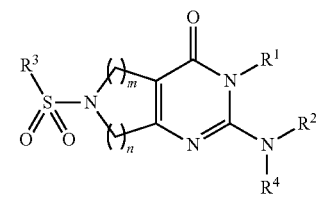

(wherein $R^1$ to $R^4$, m, n are the same as defined in [1])

This step is a step for obtaining the compound of the formula [C] by reacting Compound a7 obtained in the above Step A-6 with Compound c1 in the presence of various bases in a suitable solvent, if necessary, followed by removing the protecting groups for amino group, hydroxy group or carboxyl group for $R^1$ to $R^4$. The bases used in this step are selected from ones as exemplified hereinafter, and the preferable one is diisopropylethylamine. The solvents used in this step are selected from ones as exemplified hereinafter, and the preferable one is methylene chloride.

Method D

Among the compounds of the formula (I), the compound of the formula (I) wherein X is an oxygen atom or a sulfur atom, and Y is a group of the following formula (II), (III) or (IV):

[Chemical formula 20]

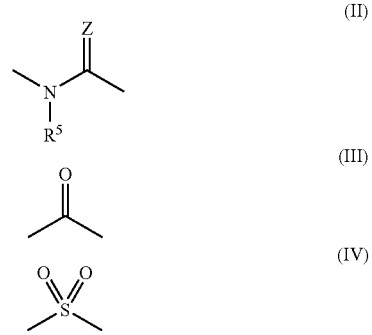

(wherein $R^5$ is as defined in [1]), i.e., the compounds of the formula [D], [E] or [F] may be prepared, for example, by the following method.

[Chemical formula 21]

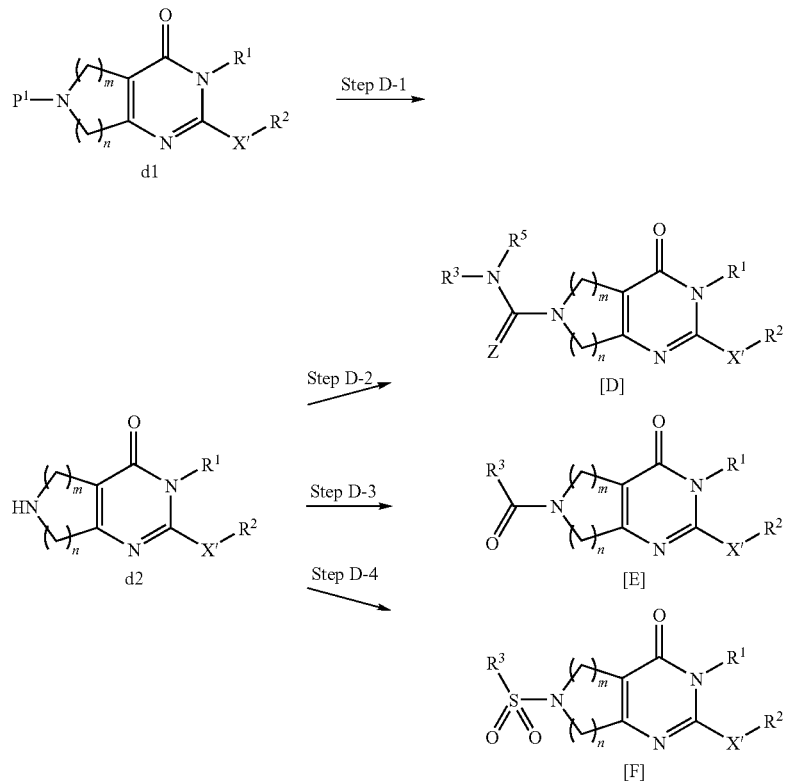

(wherein $R^1$ to $R^3$, $R^5$, Z, m, n are the same as defined in [1]; $P^1$ is the same as defined above; X' is an oxygen atom or a sulfur atom)

[Step D-1]

This step is a step for obtaining Compound d2 by removing a protecting group for amino group ($P^1$) of Compound d1 in a similar manner to the above Step A-6.

[Step D-2]

This step is a step for obtaining the compound of the formula [D] by reacting Compound d2 obtained in the above Step D-1 with Compound a11 or a12 in a similar manner to the above Step A-7.

[Step D-3]

This step is a step for obtaining the compound of the formula [E] by reacting Compound d2 obtained in the above Step D-1 with Compound b1 in a similar manner to the above Step B-1.

[Step D-4]

This step is a step for obtaining the compound of the formula [F] by reacting Compound d2 obtained in the above Step D-1 with Compound c1 in a similar manner to the above Step C-1.

[Step D-5]

When X is a sulfur atom, Compound d1 may be prepared, for example, by the following process.

[Chemical formula 22]

(wherein $R^1$, $R^2$, m, n are the same as defined in [1]; $P^1$, Hal are the same as defined above)

This step is a step for obtaining Compound d1 by reacting Compound a3 obtained in the above Step A-2 with Compound d3 in a similar manner to the above Step A-3.

[Step D-6]

When X is an oxygen atom, Compound d1 may be prepared, for example, by the following process.

[Chemical formula 23]

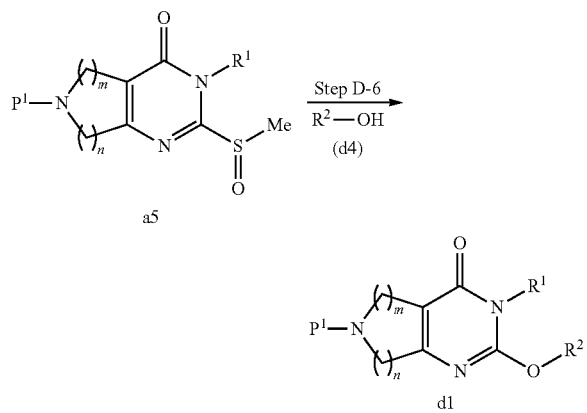

(wherein $R^1$, $R^2$, m, n are the as defined in [1]; $P^1$ is the same as defined above)

This step is a step for obtaining Compound d1 by reacting Compound a5 obtained in Step A-4 with Compound d4 in the presence of various bases in a suitable solvent. The bases used in this step are selected from ones exemplified hereinafter, and the preferable one is sodium hydride.

The starting compounds a1, a8, a9, a10, a11, a12, b1, c1, d3, d4 may be commercially available ones or may be prepared by a conventional method from commercially available compounds.

The compounds used in the above steps may be in the form of a salt, and such a salt includes, for example, the same salts of the present compounds as exemplified above.

The bases used in the above steps should suitably be selected according to the kinds of reaction or starting compounds, etc., and include, for example, alkali metal hydrogen carbonates such as sodium hydrogen carbonate, potassium hydrogen carbonate, etc.; alkali metal carbonates such as sodium carbonate, potassium carbonate, etc.; metal halides such as sodium hydride, potassium hydride, etc.; alkali metal hydroxides such as sodium hydroxide, potassium hydroxide, etc.; alkali metal alkoxides such as sodium methoxide, sodium t-butoxide, etc.; organic metal bases such as butyl lithium, lithium diisopropylamide, etc.; organic bases such as triethylamine, diisopropylethylamine, pyridine, 4-dimethylaminopyridine (DMAP), 1,8-diazabicyclo[5.4.0]-7-undecene (DBU), etc.

The solvents used in the above steps should be selected according to the kinds of reactions or starting compounds, etc., and include, for example, alcohols such as methanol, ethanol, isopropanol; ketones such as acetone, methyl ketone; halogenated hydrocarbons such as methylene chloride, chloroform; ethers such as tetrahydrofuran (THF), dioxane; aromatic hydrocarbons such as toluene, benzene; aliphatic hydrocarbons such as hexane, heptane; esters such as ethyl acetate, propyl acetate; amide such as N,N-dimethylformamide (DMF), N-methyl-2-pyrrolidone; sulfoxides such as dimethylsulfoxide (DMSO), nitriles such as acetonitrile, and these solvents may be used alone or in a mixture of two or more of these solvents. In addition, an organic base may be used as a solvent depending on the kinds of reaction.

The reaction temperature of the above each step should be suitably selected according to the kinds of reactions or starting compounds, etc., and it is usually in the range of $-100°$ C. to $200°$ C., and preferably in the range of $-70°$ C. to $100°$ C.

The reaction period in the above each step should be suitably selected according to the kinds of reaction or starting compounds, or solvents to be used, and it is usually in the range of 10 minutes to 48 hours, preferably in the range of 30 minutes to 24 hours.

In the compounds obtained in the above each step, the functional groups within the molecule thereof may be converted into a desired functional group by a combination method of conventional methods, for example, by the methods disclosed in Comprehensive Organic Transformations (written by Richard C. Larock, published by John Wiley & Sons, Inc., 1999).

The products obtained in the above each step may be isolated or purified by a conventional method such as extraction, column chromatography, recrystallization, reprecipitation, etc.

In addition, the present compounds may optionally be obtained in the form of a salt, a free acid or a free base depending on the reaction conditions to be employed, but these compounds can be converted into a desired salt, free acid or free base by a conventional method.

The present compound may be in the form of a crystal, which can be obtained by a conventional crystallization method.

When the present compound contains an optical isomer, a stereoisomer, a rotational isomer or a positional isomer, these isomers are also included in the scope of the present compound. These isomers can be obtained, for example, by synthesis from optically active starting compounds, or by a conventional separation method such as optical resolution, preferential crystallization, etc.

Pharmacological Experiments:

The pharmacological activities of the representative present compounds were studied.

Experiment 1: MGAT Activity of the Small Intestine Cells Microsome Fractions (1) Preparation of Microsome Fraction from Mouse Small Intestine Cells Small intestine was enucleated from the mice (ICR, male) and cut open, and the contents therein were washed with PBS. The cells lined at the intestinal wall of the washed small intestine were peeled off and collected with a medicine spoon within the iced Solution A (1 mM Tris solution containing 0.25 M sucrose, 1 mM EDTA, 1 mM DTT (pH7.5)). The obtained cell suspension was homogenized and centrifuged at 600×g for 15 minutes at 4° C. The obtained supernatant was further centrifuged at 105,000×g for 1 hour at 4° C. The resulting precipitates were suspended again in Solution A, and subjected to ultrasonication on ice for 6 times in a ON-OFF manner (ON: 15 seconds, OFF: 10 seconds). Further the resultant was centrifuged at 600×g for 5 minutes at 4° C., and the resulting supernatant was regarded as a microsome fraction.

(2) Measurement of MGAT Activity in the Microsome Fraction of Small Intestine Cells A solution of a test compound in DMSO (1.5 μL) in a prescribed concentration was added to a 1.5 μL Eppendorf tube. To said tube were added a 32 mM Tris solution (140 μL, pH7.4) containing 1.27 mg/mL BSA, 3.8 mM $MgCl_2$, 60 μM monooleylglycerol, 60 μM $^{14}$C-palmitoyl-CoA (GE healthcare), and the tube was incubated at 37° C. for 5 minutes. After incubation, the intestinal microsome fraction prepared by the above method (1) (0.1 mg/ml, 10 μL) (human small intestinal microsome was purchased from KAC Co., Ltd.) was added to the tube, and further incubated at 37° C. for 10 minutes. After 10 minutes, to the tube was added a solution of isopropanol:heptane:water (80:20:2 v/v) (0.3 mL), and the tube was shaken. Further, heptane (0.2 mL) and water (0.1 mL) were added thereto, and the tube was shaken again, and then centrifuged at 3,000 rpm, for 1 minute at room temperature. The lower phase (aqueous phase) was removed, and concentrated to dryness under reduced pressure. The resulting dried residue was dissolved in a mixture of chloroform:methanol (1:2 v/v, 30 µL), and spotted onto a TLC plate (Whatman). The TLC plate having a spot was developed in hexane:ethyl ether:acetic acid (75:25:1), and the radioactivity at the positions corresponding to triglyceride (TG) and diglyceride (DG) was measured using Imaging Analyzer (BAS2000, FUJIFILM Corporation).

The MGAT activity (TG radioactivity/2+DG radioactivity) when the DMSO solution was added is regarded as A, and the MGAT activity when a test compound was added is regarded as B, and then, MGAT activity inhibitory rate of said test compound is calculated according to the following equation.

MGAT Activity Inhibitory Rate (%)=$\{1-(B/A)\}\times 100$ (%)

The MGAT activity inhibitory Rates (%) of each test compound at a final concentration of 3 µM, 0.3 µM, 0.03 µM were calculated with the above equation. Further, $IC_{50}$ value, a concentration of a test compound to be needed for 50% inhibition of MGAT activity, was calculated by linear analysis using the obtained inhibitory rates.

The results are shown in Table 1.

TABLE 1

| Example No. of Test Compound | $IC_{50}$ (µM) |
|---|---|
| 1 | 0.961 |
| 2 | 0.106 |
| 6 | 0.435 |
| 8 | 0.025 |
| 61 | 0.162 |
| 102 | 0.206 |
| 119 | 0.119 |
| 120 | 0.189 |
| 124 | 0.225 |
| 126 | 0.284 |
| 161 | 0.933 |
| 164 | 0.630 |
| 169 | 0.020 |

Experiment 2: Inhibitory Activity of Fat Absorption at the Small Intestine

The inhibitory activity of fat absorption at the small intestine of compounds having MGAT inhibitory activity was studied. Mice (ICR, 9 weeks old, male, Japan SLC Inc.) were fasted overnight (about 18 hours), and water or olive oil (4 mL/kg) was administered via gavage. A compound was suspended in olive oil and administered. Three hours after the administration, the blood was collected from the heart under ether anesthesia to give the plasma. The measurement of TG in plasma chylomicron was carried out by free glycerol elimination method (Determiner-L TGII, KYOWA MEDEX Co., Ltd.) and agarose electrophoresis (Epalyzer 2, Helena Co. Ltd.). In the results, the compounds of Examples 1 and 2 suppressed the increase of plasma chylomicron TG by about more than 60% at a dose of 30 mg/kg. From the results, it is indicated that the compounds having MGAT inhibitory activity inhibit the fat absorption at the small intestine.

From the above results, the present compounds can be expected to be useful as MGAT inhibitors.

The present compound and a pharmaceutically acceptable salt thereof show MGAT inhibitory activity, and are useful as an agent for treatment and prophylaxis of adiposity, metabolic syndromes, hyperlipidemia, hyper neutral lipemia, hyper VLDL-mia, hyper fatty acidemia, diabetes mellitus, arteriosclerosis.

When the present compound is used as an MGAT inhibitor, it can be administered either orally, parenterally or rectally, but the oral administration is preferable. The dosage thereof may vary according to the administration route, conditions and ages of the patients, treatment methods (prophylaxis or treatment), etc., and it is usually in the range of 10 ng/kg/day to 10 mg/kg/day, preferably in the range of 0.1 µg/kg/day to 1 mg/kg/day, more preferably in the range of 1 µg/kg/day to 100 µg/kg/day.

The present compound is usually administered in the form of a pharmaceutical preparation, which is prepared by mixing with a pharmaceutical excipient or carrier. The pharmaceutical excipient or carrier may be any ones which are widely used in the pharmaceutical field and do not react with the present compound. For example, lactose, glucose, mannitol, dextrin, starch, white sugar, magnesium metasilicic aluminate, synthesized aluminum silicate, crystalline cellulose, sodium carboxymethyl cellulose, hydroxypropyl starch, calcium carboxymethyl cellulose, ion-exchange resin, methylcellulose, gelatin, gum arabic, hydroxypropyl cellulose, low-substituted hydroxy-propyl cellulose, hydroxypropylmethyl cellulose, polyvinylpyrrolidone, polyvinyl alcohol, light anhydrous silicic acid, magnesium stearate, talc, carboxyvinyl polymer, titanium oxide, sorbitan fatty acid ester, sodium laurylsulfate, glycerin, fatty acid glycerin ester, purified lanolin, glycerogelatin, polysolvate, macrogol, vegetable oil, wax, nonionic surfactant, propyleneglycol, water, etc.

The pharmaceutical preparation includes, for example, tablets, capsules, granules, powders, syrups, suspensions, suppositories, gels, injections, etc. These preparations may be prepared by a conventional method. In addition, for liquid preparation, it may be in such a form that it is dissolved or suspended in water or other suitable solvent when used. Tablets and granules may be coated by a conventional method. Injection preparations are prepared by dissolving a pharmaceutically acceptable salt of the compound of the formula (I) in water, but if necessary, it may further contain a tonicity agent, or a pH adjuster, a buffering agent or a preservative.

These preparations may contain the present compound in a ratio of 0.01% by weight or more, preferably in a ratio of 0.05 to 70% by weight. These preparations may further contain another active ingredient which is therapeutically effective.

BEST MODE FOR CARRYING OUT THE INVENTION

Hereinafter, the present invention will be explained in more detail by Reference Examples, Examples and Experiments, but the present invention should not be construed to be limited thereto. The identification of the compounds were done by hydrogen nuclear magnetic resonance spectrum (1H-NMR), high-performance liquid chromatograph-mass spectrography (LCMS).

Hydrogen nuclear magnetic resonance spectrum (1H-NMR) was measured by FT-NMR measuring device manufactured by Burker or JEOL. Tetramethylsilane was used as a standard substance, and the data was expressed with δ value (ppm) as chemical shift value. The abbreviations used in 1H-NMR are, for example, s is single line, d is double line, dd is a double of double line, t is triple line, m is multiple line, br is broad, and J is coupling constant.

High-performance liquid chromatograph-mass spectrography (LCMS) was measured using LCMS mass spectrometer manufactured by Finnigan or Shimadzu Corporation.

Mass spectrometry was carried out using atmospheric-pressure chemical ionization method (APCI) or Electrospray ionization method (ESI).

Herein below, the following abbreviations are occasionally used in order to simplify the description.

Me: methyl
Boc: tert-butoxycarbonyl
DMSO: Dimethylsulfoxide

Reference Example 1

Preparation of ethyl 4-amino-1-tert-butoxy-carbonyl-1,2,5,6-tetrahydropyridine-3-carboxylate

[Chemical formula 24]

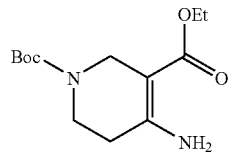

To ethyl 1-tert-butoxycarbonyl-4-oxopiperidin-3-carboxylate (65.88 g) was added a 25% aqueous ammonia (660 ml), and the mixture was heated under reflux for 2 hours. The reaction solution was diluted with ethyl acetate, and the organic layer was separated. The aqueous layer was extracted again with ethyl acetate. The organic layers were combined and dried over anhydrous sodium sulfate, and concentrated under reduced pressure. The obtained residue was purified by silica gel column chromatography (hexane/ethyl acetate: 5/3), and the obtained crude product was subjected to recrystallization (hexane/diethyl ether: 9/1) to give the title compound (37.67 g).

MS-APCI: m/z: 271 ([M+H]$^+$).
$^1$H-NMR (300 MHz, DMSO-d$_6$): δ (ppm)=7.00 (br.s, 2H), 4.05 (q, J=7.1, 2H), 3.92 (s, 2H), 3.37 (t, J=6.0, 2H), 2.26 (t, J=6.0, 2H), 1.40 (s, 9H), 1.18 (t, J=7.1, 3H).

Reference Example 2

Preparation of tert-butyl 4-oxo-3-phenyl-2-thioxo-1,3,4,5,7,8-hexahydropyrido[4,3-d]pyrimidine-6(2H)-carboxylate

[Chemical formula 25]

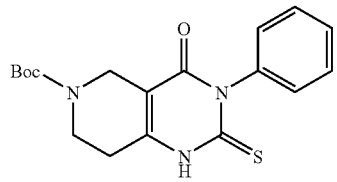

To a solution of the compound obtained in Reference Example 1 (19.3 g) in pyridine (165 ml) was added phenyl isothiocyanate (17.1 ml), and the mixture was heated at 90° C. with stirring overnight. The reaction mixture was concentrated under reduced pressure, and toluene was added to the residue, and the mixture was concentrated again under reduced pressure. The obtained crude crystals were washed with diethyl ether to give the title compound (26.75 g), which was used in the subsequent reaction without further purification.

Reference Example 3

Preparation of tert-butyl 2-(methylthio)-4-oxo-3-phenyl-3,5,7,8-tetrahydropyrido[4,3-d]pyrimidine-6(4H)-carboxylate

[Chemical formula 26]

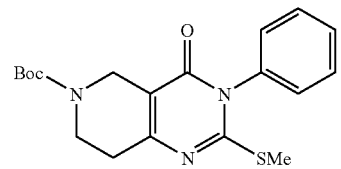

To a solution of the compound obtained in Reference Example 2 (26.75 g) in N,N-dimethylformamide (320 ml) were added 1,8-diazabicyclo[5.4.0]-7-undecene (10.6 ml) and methyl iodide (4.9 ml) at 0° C. The reaction mixture was stirred at 0° C. for 0.5 hour, and the reaction was quenched with a saturated aqueous sodium hydrogen carbonate solution. The mixture was extracted with methylene chloride, and the organic layer was washed with water, dried over anhydrous sodium sulfate, and concentrated under reduced pressure. The obtained residue was purified by silica gel column chromatography (hexane/ethyl acetate: 3/1) to give the title compound (22.03 g).

MS-APCI: m/z: 374 ([M+H]$^+$)
$^1$H-NMR (300 MHz, DMSO-d$_6$): δ (ppm)=7.57-7.52 (m, 3H), 7.37-7.34 (m, 2H), 4.17 (s, 2H), 3.61 (t, J=5.8, 2H), 2.65 (t, J=5.7, 2H), 2.39 (s, 3H), 1.43 (s, 9H).

Reference Example 4

Preparation of tert-butyl 2-(methanesulfinyl)-4-oxo-3-phenyl-3,5,7,8-tetrahydropyrido[4,3-d]pyrimidine-6(4H)-carboxylate

[Chemical formula 27]

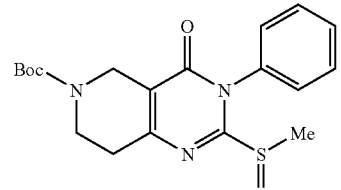

To a solution of the compound obtained in Reference Example 3 (5.0 g) in methylene chloride (100 ml) were added anhydrous magnesium sulfate (20 g) and sodium acetate (2.31 g). The reaction mixture was cooled to −70° C., and thereto was added dropwise a solution of m-chloroperbenzoic acid (9.89 g) in methylene chloride (150 ml). The reaction mixture was stirred at −70° C. for 3.5 hours, and the reaction was quenched by adding a 10% aqueous sodium thiosulfate solution at −30° C. The mixture was extracted with dichloromethane, and the organic layer was washed successively with a 10% aqueous sodium thiosulfate solution and a saturated aqueous sodium hydrogen carbonate solution, dried over anhydrous sodium sulfate, and concentrated under reduced pressure to give the title compound (6.15 g). The obtained compound was used in the subsequent reaction without further purification.

Reference Example 5

Preparation of tert-butyl 2-[(4-methoxybenzyl)-amino]-4-oxo-3-phenyl-3,5,7,8-tetrahydropyrido[4,3-d]pyrimidine-6(4H)-carboxylate

[Chemical formula 28]

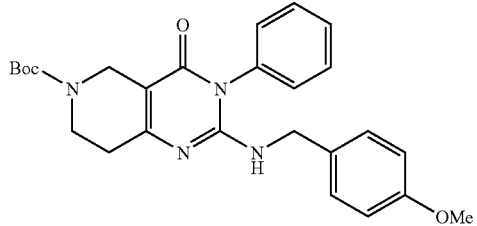

To a solution of the compound obtained in Reference Example 4 (6.15 g) in dioxane (80 ml) were added 4-methoxybenzylamine (3.5 ml), diisopropylethylamine (2.3 ml), 4-dimethylaminopyridine (0.16 g), and the mixture was heated with stirring at 50° C. for 4 hours. The reaction was quenched with water, and the mixture was extracted with ethyl acetate. The organic layer was washed successively with water, a saturated aqueous sodium hydrogen carbonate solution, a saturated aqueous sodium chloride solution, dried over anhydrous sodium sulfate and concentrated under reduced pressure. The obtained residue was purified by silica gel column chromatography (hexane/ethyl acetate: 1/1) to give the title compound (4.10 g).

$^1$H-NMR (300 MHz, DMSO-d$_6$): δ (ppm)=7.60-7.49 (m, 3H), 7.28 (dd, J=1.2, 8.2, 2H), 7.16 (d, J=8.7, 2H), 6.82 (d, J=8.7, 2H), 6.36 (t, J=5.9, 1H), 4.34 (d, J=5.5, 2H), 4.06 (s, 2H), 3.71 (s, 3H), 3.55 (t, J=5.8, 2H), 2.45 (t, J=5.7, 2H), 1.42 (s, 9H).

Reference Example 6

Preparation of 2-[(4-methoxybenzyl)amino]-3-phenyl-5,6,7,8-tetrahydropyrido[4,3-d]pyrimidin-4(3H)-one hydrochloride

[Chemical formula 29]

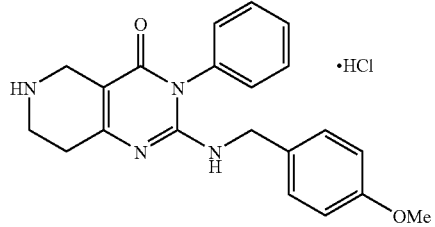

To a solution of the compound obtained in Reference Example 5 (4.10 g) in dioxane (12 ml) were added a 4 mol/l solution of hydrochloric acid in dioxane (60 ml) at 0° C. The reaction mixture was stirred at room temperature for one hour, and concentrated under reduced pressure. To the mixture was added dichloromethane, and further the mixture was concentrated under reduced pressure to give the title compound (4.03 g).

MS-APCI: m/z: 404 ([M+MeCN+H]$^+$), 363([M+H]$^+$)

$^1$H-NMR (300 MHz, DMSO-d$_6$): δ (ppm)=9.54 (br.s, 2H), 7.62-7.51 (m, 3H), 7.28 (dd, J=1.7, 8.2, 2H), 7.17 (d, J=8.7, 2H), 6.83 (d, J=8.7, 2H), 6.74 (t, J=5.6, 1H), 4.38 (d, J=5.8, 2H), 3.76-3.74 (m, 2H), 3.71 (s, 3H), 3.32-3.30 (m, 2H), 2.73-2.69 (m, 2H).

Reference Example 7

Preparation of ethyl 3-amino-1-tert-butoxy-carbonyl-1,2,5,6-tetrahydropyridine-4-carboxylate To ethyl 1-tert-butoxycarbonyl-3-oxopiperidine-4-carboxylate (80 g) was added a 7M solution of ammonia in methanol (600 ml), and the mixture was heated under reflux for 20 hours. The reaction mixture was concentrated under reduced pressure, and thereto was added a saturated aqueous sodium chloride solution, and the mixture was extracted with ethyl acetate. The organic layer was washed with a saturated aqueous sodium chloride solution, dried over anhydrous sodium sulfate, and concentrated under reduced pressure. The resulting residue was crystallized with hexane to give the title compound (60.5 g).

MS-APCI: m/z: 271 ([M+H]$^+$)

$^1$H-NMR (300 MHz, DMSO-d$_6$): δ (ppm)=7.13 (br.s, 2H), 4.03 (q, J=7.1, 2H), 3.95 (s, 2H), 3.36 (t, J=5.9, 2H), 2.19 (t, J=5.8, 2H), 1.40 (s, 9H), 1.17 (t, J=7.1, 3H).

Reference Example 8

Preparation of tert-butyl 4-oxo-3-phenyl-2-thioxo-1,3,4,5,6,8-hexahydropyrido[3,4-d]pyrimidine-7(2H)-carboxylate To a solution of the compound obtained in Reference Example 7 (50 g) in tetrahydrofuran (500 ml) was added sodium hydride (16.1 g, 55% in oil) in portions at 0° C. under stirring. The mixture was stirred at room temperature for 15 minutes, and thereto was added phenylisothiocyanate (32.7 g). The mixture was heated with stirring at 50° C. for 21 hours. The reaction was quenched with 1M hydrochloric acid, and the mixture was extracted with ethyl acetate. The organic layer was washed successively with a saturated aqueous sodium hydrogen carbonate solution and a saturated aqueous sodium chloride solution, dried over anhydrous sodium sulfate and concentrated under reduced pressure. The obtained residue was purified by silica gel column chromatography (hexane/ethyl acetate: 3/1) to give the title compound (45 g).

MS-APCI: m/z: 360 ([M+H]$^+$).

$^1$H-NMR (300 MHz, DMSO-d$_6$): δ (ppm)=12.69 (br.s, 1H), 7.48-7.35 (m, 3H), 7.16 (d, J=7.0, 2H), 4.30 (s, 2H), 3.53 (t, J=5.6, 2H), 2.31 (t, J=5.3, 2H), 1.44 (s, 9H).

Reference Example 9

Preparation of tert-butyl 2-(methylthio)-4-oxo-3-phenyl-3,5,6,8-tetrahydropyrido[3,4-d]pyrimidine-7(4H)-carboxylate The compound obtained in Reference Example 8 was reacted and treated in a similar manner to Reference Example 3 to give the title compound.

MS-APCI: m/z: 374 ([M+H]+).
¹H-NMR (300 MHz, DMSO-d₆): δ (ppm)=7.57-7.53 (m, 3H), 7.36-7.33 (m, 2H), 4.30 (s, 2H), 3.56 (t, J=5.7, 2H), 2.42 (t, J=5.6, 2H), 2.39 (s, 3H), 1.45 (s, 9H).

Reference Example 10

Preparation of tert-butyl 2-(methanesulfinyl)-4-oxo-3-phenyl-3,5,6,8-tetrahydropyrido[3,4-d]pyrimidine-7(4H)-carboxylate The compound obtained in Reference Example 9 was reacted and treated in a similar manner to Reference Example 4 to give the title compound.

Reference Example 11

Preparation of tert-butyl 2-[(4-methoxybenzyl)-amino]-4-oxo-3-phenyl-3,5,6,8-tetrahydropyrido[3,4-d]pyrimidine-7(4H)-carboxylate The compound obtained in Reference Example 10 was reacted and treated in a similar manner to Reference Example 5 to give the title Compound.
MS-APCI: m/z: 463 ([M+H]+). ¹H-NMR (300 MHz, DMSO-d₆): δ (ppm)=7.60-7.49 (m, 3H), 7.27 (d, J=6.7, 2H), 7.17 (d, J=8.6, 2H), 6.83 (d, J=8.7, 2H), 6.38 (t, J=5.6, 1H), 4.33 (d, J=5.5, 2H), 4.10 (s, 2H), 3.71 (s, 3H), 3.51 (t, J=5.5, 2H), 2.31 (t, J=5.3, 2H), 1.43 (s, 9H).

Reference Example 12

Preparation of 2-[(4-methoxybenzyl)amino]-3-phenyl-5,6,7,8-tetrahydropyrido[3,4-d]pyrimidin-4(3H)-one hydrochloride The compound obtained in Reference Example 11 was reacted and treated in a similar manner to Reference Example 6 to give the title compound.
MS-APCI: m/z: 404 ([M+MeCN+H]+), 363 ([M+H]+).
¹H-NMR (300 MHz, DMSO-d₆): δ (ppm)=9.81 (br.s, 2H), 7.62-7.51 (m, 3H), 7.28 (dd, J=1.6, 6.5, 2H), 7.18 (d, J=8.6, 2H), 6.83 (d, J=8.7, 2H), 6.72 (t, J=5.9, 1H), 4.35 (d, J=5.9, 2H), 3.83 (s, 2H), 3.71 (s, 3H), 3.26-3.24 (m, 2H), 2.53-2.50 (m, 2H).

Reference Example 13

Preparation of 2-(methylthio)-3-phenyl-3,5,7,8-tetrahydropyrido[4,3-d]pyrimidin-4(3H)-one To a solution of the compound obtained in Reference Example 3 in dioxane (50 ml) was added a solution of a 4 mol/l solution of hydrochloric acid in dioxane (150 ml) at 0° C. The reaction mixture was stirred at room temperature for one hour, and thereto was added a saturated aqueous sodium carbonate solution until the pH value of the mixture becomes pH 12. The mixture was extracted with methylene chloride, and the organic layer was dried over anhydrous sodium sulfate and concentrated under reduced pressure to give the title compound (6.7 g).
MS-APCI: m/z: 274 ([M+H]+).
¹H-NMR (300 MHz, DMSO-d₆): δ (ppm)=7.59-7.53 (m, 3H), 7.45-7.35 (m, 2H), 3.50 (s, 2H), 2.90 (t, 2H), 2.51-2.45 (m, 2H), 2.35 (s, 3H).

Reference Example 14

Preparation of tert-butyl 2-(benzylthio)-4-oxo-3-phenyl-3,5,7,8-tetrahydropyrido[4,3-d]pyrimidine-6(4H)-carboxylate The compound obtained in Reference Example 2 and benzyl bromide were reacted and treated in a similar manner to Reference Example 3 to give the title compound.
MS-APCI: m/z: 450 ([M+H]+).
¹H-NMR (300 MHz, DMSO-d₆): δ (ppm)=7.55-7.50 (m, 3H), 7.37-7.20 (m, 7H), 4.30 (s, 2H), 4.17 (s, 2H), 3.63 (t, J=5.8, 2H), 2.70 (t, J=5.6, 2H), 1.44 (s, 9H).

Reference Example 15

Preparation of 2-(benzylthio)-3-phenyl-3,5,7,8-tetrahydropyrido[4,3-d]pyrimidin-4(3H)-one hydrochloride The compound obtained in Reference Example 14 was reacted and treated in a similar manner to Reference Example 6 to give the title compound.
MS-APCI: m/z: 391 ([M+MeCN+H]+), (350 ([M+H]+).
¹H-NMR (300 MHz, DMSO-d₆): δ (ppm)=9.48 (br.s, 2H), 7.57-7.52 (m, 3H), 7.38-7.21 (m, 7H), 4.32 (s, 2H), 3.91 (s, 2H), 3.41 (t, J=6.0, 2H), 2.92 (t, J=5.9, 2H).

Example 1

Preparation of N-(2,4-dichlorophenyl)-2-[(4-methoxybenzyl)-amino]-4-oxo-3-phenyl-3,5,7,8-tetrahydropyrido[4,3-d]pyrimidine-6(4H)-carboxamide

[Chemical formula 30]

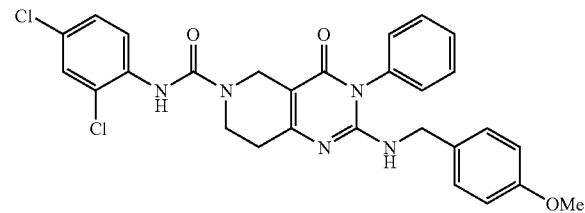

To a solution of the compound obtained in Reference Example 6 (1.40 g) in tetrahydrofuran (12 ml) were added 2,4-dichlorophenyl-isocyanate (0.726 g), diisopropylethylamine (2.75 ml), and the mixture was stirred at room temperature for 2 hours. The reaction mixture was diluted with chloroform, washed with a saturated aqueous sodium hydrogen carbonate solution. The organic layer was dried over anhydrous sodium sulfate, and concentrated under reduced pressure. The obtained residue was purified by silica gel column chromatography (hexane/ethyl acetate: 1/1) to give the title compound (1.68 g).
MS-APCI: m/z: 550, 552, 554 ([M+H]+).
¹H-NMR (300 MHz, DMSO-d₆): δ (ppm)=8.44 (s, 1H), 7.61-7.49 (m, 5H), 7.35 (dd, J=2.4, 8.7, 1H), 7.29 (dd, J=1.6, 8.3, 2H), 7.17 (d, J=8.7, 2H), 6.83 (d, J=8.7, 2H), 6.39 (t, J=5.9, 1H), 4.36 (d, J=5.9, 2H), 4.23 (s, 2H), 3.71 (s, 3H), 3.68 (t, J=5.7, 2H), 2.55-2.51 (m, 2H).

Hereinafter, the compounds of Examples 2 to 161 were obtained by reacting and treating in a similar manner to Reference Examples 1 to 6 or Example 1.

Example 2

Preparation of 2N-(3,4-difluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 518 ([M+H]$^+$).
$^1$H-NMR (300 MHz, DMSO-d$_6$): δ (ppm)=8.89 (s, 1H), 7.66-7.49 (m, 4H), 7.33-7.23 (m, 4H), 7.18 (d, J=8.7, 2H), 6.83 (d, J=8.7, 2H), 6.37 (t, J=6.0, 1H), 4.35 (d, J=5.9, 2H), 4.23 (s, 2H), 3.71 (s, 3H), 3.67 (t, J=5.76, 2H), 2.53-2.50 (m, 2H).

Example 3

Preparation of N-(2-fluorophenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 500 ([M+H]$^+$).
$^1$H-NMR (300 MHz, DMSO-d$_6$): δ (ppm)=8.46 (s, 1H), 7.61-7.50 (m, 3H), 7.45 (m, 1H), 7.30 (d, J=6.7, 2H), 7.21-7.08 (m, 5H), 6.84 (d, J=8.7, 2H), 6.37 (t, J=6.0, 1H), 4.36 (d, J=5.4, 2H), 4.22 (s, 2H), 3.72 (s, 3H), 3.68 (m, 2H), 2.54-2.49 (m, 2H).

Example 4

Preparation of N-(3-fluorophenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 500 ([M+H]$^+$).
$^1$H-NMR (300 MHz, DMSO-d$_6$): δ (ppm)=8.90 (s, 1H), 7.61-7.50 (m, 3H), 7.47-7.41 (m, 1H), 7.31-7.20 (m, 4H), 7.18 (d, J=8.7, 2H), 6.84 (d, J=8.7, 2H), 6.77-6.70 (m, 1H), 6.37 (t, J=6.0, 1H), 4.36 (d, J=5.4, 2H), 4.24 (s, 2H), 3.71 (s, 3H), 3.70-3.66 (m, 2H).

Example 5

Preparation of N-(4-fluorophenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 500 ([M+H]$^+$).
$^1$H-NMR (300 MHz, DMSO-d$_6$): δ (ppm)=8.72 (s, 1H), 7.61-7.52 (m, 3H), 7.50-7.43 (m, 2H), 7.28 (d, J=8.0, 2H), 7.17 (d, J=8.6, 2H), 7.05 (t, J=8.9, 2H), 6.83 (d, J=8.7, 2H), 6.36 (br. t, J=5.9, 1H), 4.35 (d, J=5.2, 2H), 4.22 (s, 2H), 3.71 (s, 3H), 3.68-3.64 (br. t, J=5.6, 2H), 2.51-2.49 (m, 2H).

Example 6

Preparation of N-(2-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 550 ([M+H]$^+$).
$^1$H-NMR (300 MHz, DMSO-d$_6$): δ (ppm)=8.36 (br.s, 1H), 7.69-7.37 (m, 7H), 7.29 (d, J=6.7, 2H), 7.18 (d, J=8.7, 2H), 6.83 (d, J=8.7, 2H), 6.36 (t, J=6.0, 1H), 4.36 (d, J=5.4, 2H), 4.21 (s, 2H), 3.71 (s, 3H), 3.67 (t, J=5.7, 2H), 2.51-2.49 (m, 2H).

Example 7

Preparation of N-[(3-trifluoromethyl)phenyl]-2-[(4-methoxybenzyl)amino]-4-oxo-3-phenyl-3,5,7,8-tetrahydropyrido[4,3-d]-pyrimidine-6(4H)-carboxamide MS-APCI: m/z: 550 ([M+H]$^+$).
$^1$H-NMR (300 MHz, DMSO-d$_6$): δ (ppm)=9.04 (s, 1H), 7.94 (s, 1H), 7.77 (d, J=8.0, 1H), 7.61-7.50 (m, 3H), 7.46 (t, J=8.0, 1H), 7.31-7.28 (m, 3H), 7.19-7.16 (m, 2H), 6.86-6.82 (m, 2H), 6.38 (t, J=6.0, 1H), 4.36 (d, J=5.3, 2H), 4.26 (s, 2H), 3.71 (s, 3H), 3.71-3.68 (m, 2H), 2.56-2.49 (m, 2H).

Example 8

Preparation of N-[(4-trifluoromethyl)phenyl]-2-[(4-methoxybenzyl)amino]-4-oxo-3-phenyl-3,5,7,8-tetrahydropyrido[4,3-d]-pyrimidine-6(4H)-carboxamide MS-APCI: m/z: 550 ([M+H]$^+$).
$^1$H-NMR (300 MHz, DMSO-d$_6$): δ (ppm)=9.09 (br.s, 1H), 7.70 (d, J=8.7, 2H), 7.68-7.50 (m, 5H), 7.29 (d, J=6.8, 2H), 7.17 (d, J=8.6, 2H), 6.83 (d, J=8.6, 2H), 6.38 (t, J=5.9, 1H), 4.36 (d, J=5.2, 2H), 4.26 (s, 2H), 3.71 (s, 3H), 3.71-3.65 (m, 2H), 2.55-2.50 (m, 2H).

Example 9

Preparation of N-(2-chlorophenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 516, 518 ([M+H]$^+$).

Example 10

Preparation of N-(3-chloro-2-fluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 534, 536 ([M+H]$^+$).
$^1$H-NMR (300 MHz, DMSO-d$_6$): δ (ppm)=8.68 (s, 1H), 7.62-7.49 (m, 3H), 7.42-7.36 (m, 1H), 7.32-7.26 (m, 3H), 7.21-7.09 (m, 3H), 6.84 (d, J=8.7, 2H), 6.38 (t, J=5.9, 1H), 4.36 (d, J=5.1, 2H), 4.23 (s, 2H), 3.71 (s, 3H), 3.68 (t, J=5.6, 2H), 2.53-2.49 (m, 2H).

Example 11

Preparation of N-(2,3-dichlorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 550, 552, 554 ([M+H]$^+$).
$^1$H-NMR (300 MHz, DMSO-d$_6$): δ (ppm)=8.54 (s, 1H), 7.61-7.53 (m, 3H), 7.50-7.47 (m, 1H), 7.46-7.41 (m, 1H), 7.33-7.27 (m, 3H), 7.18 (d, J=8.6, 2H), 6.84 (d, J=8.7, 2H), 6.39 (t, J=6.0, 1H); 4.36 (d, J=4.3, 2H), 4.24 (s, 2H), 3.72 (s, 3H), 3.71-3.67 (m, 2H), 2.54-2.49 (m, 2H).

Example 12

Preparation of N-(2-fluoro-3-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 568 ([M+H]$^+$).
$^1$H-NMR (300 MHz, DMSO-d$_6$): δ (ppm)=8.78 (s, 1H), 7.76 (t, J=7.7, 1H), 7.61-7.53 (m, 3H), 7.50-7.44 (m, 1H), 7.35-7.28 (m, 3H), 7.18 (d, J=8.7, 2H), 6.84 (d, J=8.7, 2H), 6.39 (t, J=6.0, 1H), 4.37 (d, J=4.8, 2H), 4.24 (s, 2H), 3.71 (s, 3H), 3.70-3.68 (m, 2H), 2.56-2.54 (m, 2H).

Example 13

Preparation of N-(2,4-difluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 518 ([M+H]$^+$).
$^1$H-NMR (300 MHz, DMSO-d$_6$): δ (ppm)=8.47 (s, 1H), 7.61-7.55 (m, 3H), 7.43-7.31 (m, 1H), 7.30 (d, J=8.0, 2H), 7.21 (m, 1H), 7.19 (d, J=8.6, 2H), 7.00 (t, J=8.7, 1H), 6.83 (d, J=8.7, 2H), 6.37 (br. t, J=6.0, 1H), 4.36 (d, J=5.3, 2H), 4.21 (s, 2H), 3.71 (s, 3H), 3.68-3.64 (br. t, J=5.6, 2H), 2.51-2.49 (m, 2H).

Example 14

Preparation of N-(4-chloro-2-fluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 534, 536 ([M+H]$^+$).
$^1$H-NMR (300 MHz, DMSO-d$_6$): δ (ppm)=8.57 (br. s, 1H), 7.60-7.37 (m, 5H), 7.29 (d, J=7.2, 2H), 7.20 (s, 1H), 7.18 (d, J=8.4, 2H), 6.83 (d, J=8.4, 2H), 6.36 (t, J=5.8, 1H), 4.36 (d, J=5.4, 2H), 4.21 (s, 2H), 3.71 (s, 3H), 3.68 (t, J=5.5, 2H), 2.51-2.49 (m, 2H).

Example 15

Preparation of N-(2-chloro-4-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 530, 532 ([M+H]$^+$).
$^1$H-NMR (300 MHz, DMSO-d$_6$): δ (ppm)=8.27 (s, 1H), 7.61-7.50 (m, 3H), 7.37-7.29 (m, 4H), 7.18 (d, J=8.7, 2H), 7.08 (dd, J=8.1, 1.3, 1H), 6.87-6.82 (m, 2H), 6.37 (t, J=6.0, 1H), 4.36 (d, J=5.8, 2H), 4.22 (s, 2H), 3.72 (s, 3H), 3.68 (t, J=5.7, 2H), 2.55-2.49 (m, 2H), 2.28 (s, 3H).

Example 16

Preparation of N-(4-chloro-2-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 530, 532 ([M+H]$^+$).
$^1$H-NMR (300 MHz, DMSO-d$_6$): δ (ppm)=8.25 (br. s, 1H), 7.62-7.50 (m, 3H), 7.35-7.12 (m, 5H), 7.17 (d, J=9.0, 2H), 6.84 (d, J=8.5, 2H), 6.37 (t, J=5.9, 1H), 4.36 (d, J=5.6, 2H), 4.22 (s, 2H), 3.71 (s, 3H), 3.71-3.62 (m, 2H), 2.55-2.50 (m, 2H), 2.15 (s, 3H).

Example 17

Preparation of N-(2-chloro-4-trifluoromethylphenyl)-2-[(4-methoxybenzyl)amino]-4-oxo-3-phenyl-3,5,7,8-tetrahydropyrido[4,3-d]pyrimidine-6(4H)-carboxamide MS-APCI: m/z: 584, 586 ([M+H]$^+$).
$^1$H-NMR (300 MHz, DMSO-d$_6$): δ (ppm)=8.57 (s, 1H), 7.85-7.82 (m, 2H), 7.67-7.50 (m, 4H), 7.30 (m, 2H), 7.18 (d, J=8.7, 2H), 6.84 (m, 2H), 6.41 (t, J=5.9, 1H), 4.36 (d, J=5.5, 2H), 4.26 (s, 2H), 3.73-3.69 (m, 2H), 3.71 (s, 3H), 2.56 (t, J=5.6, 2H).

Example 18

Preparation of N-(4-fluoro-2-trifluoromethylphenyl)-2-[(4-methoxybenzyl)amino]-4-oxo-3-phenyl-3,5,7,8-tetrahydropyrido[4,3-d]pyrimidine-6(4H)-carboxamide MS-APCI: m/z: 568 ([M+H]$^+$).
$^1$H-NMR (300 MHz, DMSO-d$_6$): δ (ppm)=8.39 (s, 1H), 7.61-7.46 (m, 6H), 7.30 (d, J=7.9, 2H), 7.18 (d, J=8.0, 2H), 6.84 (d, J=7.7, 2H), 6.36 (t, J=6.2, 1H), 4.36 (d, J=5.6, 2H), 4.20 (s, 2H), 3.72 (s, 3H), 3.67 (m, 2H), 2.54-2.49 (m, 2H).

Example 19

Preparation of N-(4-chloro-2-trifluoromethylphenyl)-2-[(4-methoxybenzyl)amino]-4-oxo-3-phenyl-3,5,7,8-tetrahydropyrido[4,3-d]pyrimidine-6(4H)-carboxamide MS-APCI: m/z: 584, 586 ([M+H]$^+$).
$^1$H-NMR (300 MHz, DMSO-d$_6$): δ (ppm)=8.44 (s, 1H), 7.74-7.68 (m, 2H), 7.61-7.47 (m, 4H), 7.28 (m, 2H), 7.18 (d, J=8.7, 2H), 6.85 (d, J=8.7, 2H), 6.38 (t, J=5.9, 1H), 4.36 (d, J=5.4, 2H), 4.21 (s, 2H), 3.71 (s, 3H), 3.67 (t, J=5.6, 2H), 2.52-2.49 (m, 2H).

Example 20

Preparation of N-(2,5-difluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 518 ([M+H]$^+$).
$^1$H-NMR (300 MHz, DMSO-d$_6$): δ (ppm)=8.61 (s, 1H), 7.61-7.50 (m, 3H), 7.42 (m, 1H), 7.29 (d, J=6.9, 2H), 7.27-7.21 (m, 1H), 7.18 (d, J=8.5, 2H), 6.94-6.86 (m, 1H), 6.84 (d, J=8.5, 2H), 6.38 (t, J=5.8, 1H), 4.36 (d, J=5.5, 2H), 4.23 (s, 2H), 3.71 (s, 3H), 3.68 (m, 2H), 2.54-2.49 (m, 2H).

Example 21

Preparation of N-(2,5-dichlorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 550, 552, 554 ([M+H]$^+$).
$^1$H-NMR (300 MHz, DMSO-d$_6$): δ (ppm)=8.43 (s, 1H), 7.67 (d, J=2.5, 1H), 7.61-7.52 (m, 2H), 7.48 (d, J=8.6, 2H), 7.31-7.27 (m, 2H), 7.21-7.16 (m, 3H), 6.85 (m, 2H), 6.39 (t, J=6.0, 1H), 4.36 (d, J=5.6, 2H), 4.24 (s, 2H), 3.71 (s, 3H), 3.71-3.67 (m, 2H), 2.54-2.49 (m, 2H).

Example 22

Preparation of N-(2-fluoro-5-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 514 ([M+H]$^+$).
$^1$H-NMR (300 MHz, DMSO-d$_6$): δ (ppm)=8.39 (s, 1H), 7.61-7.50 (m, 3H), 7.30 (d, J=7.8, 2H), 7.24 (d, J=7.7, 1H), 7.18 (d, J=8.0, 2H), 7.07-7.01 (m, 1H), 6.93-6.88 (br. m, 1H), 6.84 (d, J=7.7, 2H), 6.37 (t, J=5.6, 1H), 4.36 (d, J=5.3, 2H), 4.21 (s, 2H), 3.71 (s, 3H), 3.68-3.65 (m, 2H), 2.52-2.49 (m, 2H), 2.24 (s, 3H).

Example 23

Preparation of N-(2-chloro-5-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 530, 532 ([M+H]$^+$).
$^1$H-NMR (300 MHz, DMSO-d$_6$): δ (ppm)=8.26 (br. s, 1H), 7.64-7.49 (m, 3H), 7.35-7.25 (m, 4H), 7.18 (d, J=8.7, 2H), 6.96 (br. d, J=2.0, 1H), 6.84 (dd, J=8.7, 1.9, 2H), 6.37 (t, J=6.0, 1H), 4.36 (d, J=5.6, 2H), 4.21 (s, 2H), 3.71 (s, 3H), 3.71-3.63 (m, 2H), 2.51-2.49 (m, 2H), 2.27 (s, 3H).

Example 24

Preparation of N-(5-chloro-2-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 530, 532 ([M+H]$^+$).
$^1$H-NMR (300 MHz, DMSO-d$_6$): δ (ppm)=8.27 (s, 1H), 7.61-7.49 (m, 3H), 7.35-7.26 (m, 3H), 7.18 (m, 3H), 7.08 (dd, J=1.9, 8.0, 1H), 6.84 (d, J=8.4, 2H), 6.37 (t, J=5.8, 1H), 4.36 (d, J=5.4, 2H), 4.23 (s, 2H), 3.71 (s, 3H), 3.68 (t, J=5.4, 2H), 2.53-2.49 (m, 2H), 2.15 (s, 3H).

Example 25

Preparation of N-(5-fluoro-2-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 514 ([M+H]$^+$).
$^1$H-NMR (300 MHz, DMSO-d$_6$): δ (ppm)=8.22 (s, 1H), 7.61-7.50 (m, 3H), 7.30-7.28 (m, 2H), 7.20-7.12 (m, 4H), 6.88-6.81 (m, 3H), 6.37 (t, J=6.0, 1H), 4.36 (d, J=5.7, 2H), 4.23 (s, 2H), 3.71 (s, 3H), 3.70-3.66 (m, 2H), 2.55-2.50 (m, 2H), 2.14 (s, 3H).

Example 26

Preparation of N-(2-fluoro-5-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 568 ([M+H]$^+$)
$^1$H-NMR (300 MHz, DMSO-d$_6$): δ (ppm)=8.76 (s, 1H), 7.91 (d, J=5.5, 1H), 7.61-7.42 (m, 5H), 7.30 (d, J=8.0, 2H), 7.18 (d, J=8.7, 2H), 6.84 (d, J=8.7, 2H), 6.38 (br. t, J=5.9, 1H), 4.36 (d, J=5.7, 2H), 4.24 (s, 2H), 3.71 (s, 3H), 3.69-3.67 (m, 2H), 2.51-2.49 (m, 2H).

Example 27

Preparation of N-(2-chloro-5-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 584, 586 ([M+H]$^+$).
$^1$H-NMR (300 MHz, DMSO-d$_6$): δ (ppm)=8.58 (s, 1H), 7.94 (s, 1H), 7.70 (d, J=8.3, 1H), 7.61-7.46 (m, 4H), 7.29 (d, J=7.3, 2H), 7.18 (d, J=8.4, 2H), 6.84 (d, J=8.2, 2H), 6.39 (br. t, J=5.9, 1H), 4.36 (d, J=5.3, 2H), 4.25 (s, 2H), 3.71 (s, 3H), 3.71-3.69 (m, 2H), 2.55-2.50 (m, 2H).

Example 28

Preparation of N-(5-chloro-2-methoxyphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 546, 548 ([M+H]$^+$).
$^1$H-NMR (300 MHz, DMSO-d$_6$): δ (ppm)=7.87 (s, 1H), 7.82 (br. d, J=2.0, 1H), 7.61-7.53 (m, 3H), 7.29 (br.d, J=4.7, 2H), 7.17 (d, J=8.7, 2H), 7.02 (br. s, 2H), 6.83 (br. d, J=8.7, 2H), 6.39 (t, J=6.0, 1H), 4.36 (d, J=5.7, 2H), 4.21 (s, 2H), 3.82 (s, 3H), 3.71 (s, 3H), 3.66 (dd ('t'), J=5.7, 2H), 2.51-2.49 (m, 2H).

Example 29

Preparation of N-(3-fluoro-4-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 514 ([M+H]$^+$).
$^1$H-NMR (300 MHz, DMSO-d$_6$): δ (ppm)=8.78 (s, 1H), 7.60-7.52 (m, 3H), 7.37 (d, J=12.8, 1H), 7.29 (d, J=8.2, 2H), 7.18-7.09 (m, 4H), 6.83 (d, J=8.7, 2H), 6.36 (br. t, 1H), 4.35 (d, J=5.5, 2H), 4.22 (s, 2H), 3.70 (s, 3H), 3.68-3.64 (t, J=5.5, 2H), 2.51-2.49 (m, 2H), 2.14 (s, 3H).

Example 30

Preparation of N-(3,4-dichlorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 550, 552, 554 ([M+H]$^+$).
$^1$H-NMR (300 MHz, DMSO-d$_6$): δ (ppm)=8.98 (br. s, 1H), 7.85 (s, 1H), 7.61-7.47 (m, 5H), 7.29 (d, J=6.8, 2H), 7.18 (d, J=8.7, 2H), 6.83 (d, J=6.8, 2H), 6.37 (t, J=6.1, 1H), 4.36 (d, J=5.6, 2H), 4.23 (s, 2H), 3.71 (s, 3H), 3.68 (t, J=5.4, 2H), 2.51-2.49 (m, 2H).

Example 31

Preparation of N-(3-chloro-4-fluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 534, 536 ([M+H]$^+$)
$^1$H-NMR (300 MHz, DMSO-d$_6$): δ (ppm)=8.87 (br. s, 1H), 7.74-7.77 (m, 1H), 7.60-7.52 (m, 3H), 7.46-7.41 (m, 1H), .

7.31-7.25 (m, 3H), 7.18 (d, J=8.7, 2H), 6.83 (d, J=8.7, 2H), 6.37 (t, J=6.1, 1H), 4.36 (d, J=5.7, 2H), 4.23 (s, 2H), 3.71 (s, 3H), 3.67 (t, J=5.8, 2H), 2.51-2.49 (m, 2H).

Example 32

Preparation of N-(4-fluoro-3-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 514 ([M+H]$^+$).
$^1$H-NMR (300 MHz, DMSO-d$_6$): δ (ppm)=8.64 (br. s, 1H), 7.60-7.50 (m, 3H), 7.34 (d, J=7.0, 1H), 7.30-7.28 (m, 3H), 7.18 (d, J=8.2, 2H), 7.01 (t, J=9.1, 1H), 6.83 (d, J=7.8, 2H), 6.36 (t, J=5.7, 1H), 4.35 (d, J=5.5, 2H), 4.21 (s, 2H), 3.71 (s, 3H), 3.66 (t, J=5.2, 2H), 2.51-2.49 (m, 2H), 2.18 (s, 3H).

Example 33

Preparation of N-(4-fluoro-3-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 568 ([M+H]$^+$).
$^1$H-NMR (300 MHz, DMSO-d$_6$): δ (ppm)=9.03 (s, 1H), 7.95 (dd, J=6.5, 2.6, 1H), 7.84-7.78 (m, 1H), 7.62-7.50 (m, 3H), 7.37 (dd, J=9.8, 1H), 7.31-7.28 (m, 2H), 7.19-7.15 (m, 2H), 6.86-6.81 (m, 2H), 6.38 (t, J=6.0, 1H), 4.36 (d, J=5.8, 2H), 4.25 (s, 2H), 3.71 (s, 3H), 3.71-3.67 (m, 2H), 2.55-2.49 (m, 2H).

Example 34

Preparation of N-(4-chloro-3-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 584, 586 ([M+H]$^+$).
$^1$H-NMR (300 MHz, DMSO-d$_6$): δ (ppm)=9.13 (s, 1H), 8.07 (d, J=2.5, 1H), 7.82 (dd, J=2.5, 8.9, 1H), 7.61-7.53 (m, 4H), 7.31-7.28 (m, 2H), 7.18 (d, J=8.6, 2H), 6.86-6.82 (m, 2H), 6.38 (t, J=6.0, 1H), 4.35 (d, J=5.6, 2H), 4.25 (s, 2H), 3.71 (s, 3H), 3.71-3.68 (m, 2H), 2.52-2.49 (m, 2H).

Example 35

Preparation of N-(3,5-difluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 518 ([M+H]$^+$).
$^1$H-NMR (300 MHz, DMSO-d$_6$): δ (ppm)=9.07 (s, 1H), 7.61-7.52 (m, 3H), 7.31-7.25 (m, 4H), 7.17 (d, J=8.7, 2H), 6.86-6.82 (m, 2H), 6.76-6.69 (m, 1H), 6.38 (t, J=6.0, 1H), 4.35 (d, J=5.7, 2H), 4.24 (s, 2H), 3.71 (s, 3H), 3.71-3.66 (m, 2H), 2.54-2.49 (m, 2H).

Example 36

Preparation of N-(3-fluoro-5-trifluoromethylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 568 ([M+H]$^+$)
$^1$H-NMR (300 MHz, DMSO-d$_6$): δ (ppm)=9.22 (br. s, 1H), 7.80-7.70 (m, 2H), 7.62-7.50 (m, 3H), 7.29 (d, J=6.7, 2H), 7.17 (d, J=8.6, 2H), 7.17-7.15 (m, 1H), 6.84 (d, J=8.7, 2H), 6.39 (t, J=5.9, 1H), 4.36 (d, J=5.7, 2H), 4.26 (s, 2H), 3.71 (s, 3H), 3.71-3.65 (m, 2H), 2.55-2.50 (m).

Example 37

Preparation of N-(3,5-dichlorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 550, 552, 554 ([M+H]$^+$).
$^1$H-NMR (300 MHz, DMSO-d$_6$): δ (ppm)=9.05 (br. s, 1H), 7.64-7.42 (m, 5H), 7.31 (br. d, J=6.7, 2H), 7.17 (d, J=8.7, 2H), 7.11-7.09 (m, 1H), 6.83 (d, J=8.7, 2H), 6.35 (t, J=6.0, 1H), 4.36 (d, J=5.7, 2H), 4.21 (s, 2H), 3.70 (s, 3H), 3.71-3.63 (m, 2H), 2.51-2.49 (m, 2H).

Example 38

Preparation of N-(2,6-difluorophenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 518 ([M+H]$^+$).
$^1$H-NMR (300 MHz, DMSO-d$_6$): δ (ppm)=8.42 (br. s, 1H), 7.62-7.50 (m, 3H), 7.32-7.22 (m, 3H), 7.18 (d, J=8.6, 2H), 7.15-7.05 (m, 2H), 6.84 (d, J=8.7, 2H), 6.37 (t, J=5.9, 1H), 4.36 (d, J=5.7, 2H), 4.22 (s, 2H), 3.71 (s, 3H), 3.71-3.65 (m, 2H), 2.55-2.50 (m, 2H).

Example 39

Preparation of N-(3-chloro-4-methylphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 530, 532 ([M+H]$^+$)
$^1$H-NMR (300 MHz, DMSO-d$_6$): δ (ppm)=8.77 (s, 1H), 7.64-7.49 (m, 4H), 7.35-7.27 (m, 3H), 7.19-7.16 (m, 3H), 6.83 (d, J=8.7, 2H), 6.36 (t, J=6.0, 1H), 4.35 (d, J=5.7, 2H), 4.22 (s, 2H), 3.71 (s, 3H), 3.71-3.64 (m, 2H), 2.51-2.49 (m, 2H), 2.24 (s, 3H)

Example 40

Preparation of N-(3-chloro-4-methoxyphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 546, 548 ([M+H]$^+$).
$^1$H-NMR (300 MHz, DMSO-d$_6$): δ (ppm)=8.67 (br. s, 1H), 7.70-7.50 (m, 4H), 7.37 (d, J=9.0, 1H), 7.29 (d, J=8.0, 2H), 7.17 (d, J=7.8, 2H), 7.03 (d, J=8.2, 1H), 6.84 (d, J=7.4, 2H), 6.36 (t, J=5.4, 1H), 4.35 (d, J=4.8, 2H), 4.21 (s, 2H), 3.79 (s, 3H), 3.71 (s, 3H), 3.71-3.62 (m, 2H), 2.55-2.50 (m, 2H).

Example 41

Preparation of N-(2-trifluoromethoxyphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 566 ([M+H]$^+$).
$^1$H-NMR (300 MHz, DMSO-d$_6$): δ (ppm)=8.49 (s, 1H), 7.61-7.48 (m, 4H), 7.34-7.27 (m, 4H), 7.22-7.16 (m, 3H), 6.83 (d, J=8.7, 2H), 6.37 (t, J=6.0, 1H), 4.36 (d, J=5.5, 2H), 4.22 (s, 2H), 3.71 (s, 3H), 3.68 (t, J=5.6, 2H), 2.52-2.49 (m, 2H).

Example 42

Preparation of N-(4-trifluoromethoxyphenyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 566 ([M+H]$^+$).
$^1$H-NMR (300 MHz, DMSO-d$_6$): δ (ppm)=8.89 (s, 1H), 7.65-7.49 (m, 5H), 7.29 (d, J=8.7, 2H), 7.25-7.17 (m, 4H), 6.83 (d, J=8.0, 2H), 6.37 (t, J=5.8, 1H), 4.36 (d, J=5.5, 2H), 4.24 (s, 2H), 3.71 (s, 3H), 3.68 (t, J=5.5, 2H), 2.51-2.49 (m, 2H).

Example 43

Preparation of N-(2-carboxyphenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 526 ([M+H]$^+$).
$^1$H-NMR (300 MHz, DMSO-d$_6$): δ (ppm)=13.7-13.3 (br. s, 1H), 11.06 (br. s, 1H), 8.41 (d, J=8.4, 1H), 7.96 (d, J=6.8, 1H), 7.61-7.50 (m, 4H), 7.30 (d, J=6.9, 2H), 7.18 (d, J=8.5, 2H), 7.02 (t, J=7.6, 1H), 6.84 (d, J=8.5, 2H), 6.39 (t, J=5.9, 1H), 4.36 (d, J=5.6, 2H), 4.26 (s, 2H), 3.74-3.71 (s, 5H), 2.56-2.55 (m, 2H).

Example 44

Preparation of N-(3-carboxyphenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 526 ([M+H]$^+$).
$^1$H-NMR (300 MHz, DMSO-d$_6$): δ (ppm)=12.77 (br. s, 1H), 8.91 (s, 1H), 8.11 (s, 1H), 7.73 (br. d, J=8.1, 1H), 7.61-7.50 (m, 4H), 7.37-7.29 (m, 3H), 7.17 (d, J=8.6, 2H), 6.83 (d, J=8.6, 2H), 6.35 (t, J=6.0, 1H), 4.36 (d, J=5.7, 2H), 4.24 (s, 2H), 3.71 (s, 3H), 3.71-3.67 (m, 2H), 2.51-2.49 (m, 2H).

Example 45

Preparation of N-(4-carboxyphenyl)-2-[(4-methoxybenzyl)-amino]-4-oxo-3-phenyl-3,5,7,8-tetrahydropyrido[4,3-d]pyrimidine-6(4H)-carboxamide MS-APCI: m/z: 526 ([M+H]$^+$).
$^1$H-NMR (300 MHz, DMSO-d$_6$): δ (ppm)=12.51 (br. s, 1H), 9.04 (s, 1H), 7.81 (d, J=8.8, 2H), 7.61-7.52 (m, 5H), 7.29 (d, J=6.8, 2H), 7.18 (d, J=7.6, 2H), 6.83 (d, J=8.7, 2H), 6.36 (t, J=6.0, 1H), 4.35 (d, J=5.7, 2H), 4.25 (s, 2H), 3.71 (s, 3H), 3.71-3.67 (m, 2H), 2.51-2.49 (m, 2H).

Example 46

Preparation of N-(3,5-dichlorophenyl)-2-[(4-methoxybenzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=9.05 (br. s, 1H), 7.64-7.42 (m, 5H), 7.31 (br. d, J 6.7, 2H), 7.17 (d, J=8.7, 2H), 7.11-7.09 (m, 1H), 6.83 (d, J=8.7, 2H), 6.35 (t, J=6.0, 1H), 4.36 (d, J=5.7, 2H), 4.21 (s, 2H), 3.70 (s, 3H), 3.71-3.63 (m, 2H), 2.51-2.49 (m, 2H).

Example 47

Preparation of N-(3-fluoro-5-trifluoromethylphenyl)-2-[(4-methoxybenzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=9.22 (br. s, 1H), 7.80-7.70 (m, 2H), 7.62-7.50 (m, 3H), 7.29 (d, J=6.7, 2H), 7.17 (d, J=8.6, 2H), 7.17-7.15 (m, 1H), 6.84 (d, J=8.7, 2H), 6.39 (t, J=5.9, 1H), 4.36 (d, J=5.7, 2H), 4.26 (s, 2H), 3.71 (s, 3H), 3.71-3.65 (m, 2H), 2.55-2.50 (m, 2H).

Example 48

Preparation of N-(tert-butyl)-2-[(4-methoxybenzyl)amino]-4-oxo-3-phenyl-3,5,7,8-tetrahydropyrido[4,3-d]pyrimidine-6(4H)-carboxamide MS-APCI: m/z: 462 ([M+H]$^+$).
$^1$H-NMR (300 MHz, DMSO-d$_6$): δ (ppm)=7.61-7.49 (m, 3H), 7.28 (m, 2H), 7.17 (d, J=8.7, 2H), 6.83 (d, J=8.5, 2H), 6.30 (t, J=5.9, 1H), 5.88 (s, 1H), 4.35 (d, J=5.7, 2H), 4.02 (s, 2H), 3.71 (s, 3H), 3.50 (t, J=5.6, 2H), 2.42 (t, J=5.3, 2H), 1.26 (s, 9H).

Example 49

Preparation of N-hexyl-2-[(4-methoxybenzyl)amino]-4-oxo-3-phenyl-3,5,7,8-tetrahydropyrido[4,3-d]pyrimidine-6(4H)-carboxamide MS-APCI: m/z: 490 ([M+H]$^+$).

Example 50

Preparation of N-(cyclohexyl)-2-[(4-methoxybenzyl)amino]-4-oxo-3-phenyl-3,5,7,8-tetrahydropyrido[4,3-d]pyrimidine-6(4H)-carboxamide MS-APCI: m/z: 488 ([M+H]$^+$).

Example 51

Preparation of N-(2-thiophen-2-yl-ethyl)-2-[(4-methoxybenzyl)amino]-4-oxo-3-phenyl-3,5,7,8-tetrahydropyrido[4,3-d]-pyrimidine-6(4H)-carboxamide MS-APCI: m/z: 516 ([M+H]$^+$).

Example 52

Preparation of N-(2,4-dichlorophenyl)-2-[(4-methoxybenzyl)amino]-4-oxo-3-(2-methoxyphenyl)-3,5,7,8-tetrahydropyrido[4,3-d]pyrimidine-6(4H)-carboxamide $^1$H-NMR (300 MHz, DMSO-d$_6$): δ (ppm)=8.42 (s, 1H), 7.59 (d, J=2.4, 1H), 7.54-7.48 (m, 2H), 7.36 (dd, J=2.4, 8.7, 1H), 7.26-7.08 (m, 5H), 6.85 (d, J=8.7, 2H), 6.51 (t, J=5.9, 1H), 4.44 (dd, J=6.4, 15.1, 1H), 4.27 (dd, J=5.7, 15.2, 1H), 4.21 (s, 2H), 3.75 (s, 3H), 3.72 (s, 3H), 3.72-3.66 (m, 2H), 2.52-2.49 (m, 2H).

Example 53

Preparation of N-(2,4-dichlorophenyl)-2-[(4-methoxybenzyl)amino]-3-(3-methoxyphenyl)-4-oxo-3,5,7,8-tetrahydropyrido[4,3-d]pyrimidine-6(4H)-carboxamide $^1$H-NMR (300 MHz, DMSO-d$_6$): δ (ppm)=8.44 (s, 1H), 7.60 (d, J=2.4, 1H), 7.53-7.45 (m, 2H), 7.34 (dd, J=2.4, 8.7, 1H), 7.19 (d, J=8.7, 2H), 7.09 (dd, J=2.5, 7.7, 1H), 6.90 (t, J=2.1, 1H), 6.86-6.83 (m, 1H), 6.84 (d, J=8.7, 2H), 6.46 (t, J=5.9, 1H), 4.37 (dd, J=5.0, 2H), 4.23 (s, 2H), 3.79 (s, 3H), 3.71 (s, 3H), 3.71-3.66 (m, 2H), 2.52-2.49 (m, 2H).

Example 54

Preparation of N-(2,4-dichlorophenyl)-2-[(4-methoxybenzyl)amino]-3-(4-methoxyphenyl)-4-oxo-3,5,7,8-tetrahydropyrido[4,3-d]pyrimidine-6(4H)-carboxamide $^1$H-NMR (300 MHz, DMSO-d$_6$): δ (ppm)=8.43 (s, 1H), 7.59 (d, J=2.4, 1H), 7.52 (d, J=8.7, 1H), 7.36 (dd, J=2.4, 8.7, 1H), 7.21-7.17 (m, 4H), 7.10 (d, J=9.0, 2H), 6.84 (d, J=8.7, 2H), 6.45 (t, J=6.0, 1H), 4.35 (d, J=5.9, 2H), 4.22 (s, 2H), 3.83 (s, 3H), 3.71 (s, 3H), 3.71-3.66 (m, 2H), 2.52-2.49 (m, 2H).

Example 55

Preparation of N-(2,4-dichlorophenyl)-2-[(4-methoxybenzyl)amino]-3-(3-methylphenyl)-4-oxo-3,5,7,8-tetrahydropyrido[4,3-d]pyrimidine-6(4H)-carboxamide $^1$H-NMR (300 MHz, DMSO-d$_6$): δ (ppm)=8.43 (s, 1H), 7.59 (d, J=1.4, 1H), 7.52 (d, J=8.7, 1H), 7.46 (t, J=7.7, 1H), 7.38-7.32 (m, 2H), 7.18 (d, J=8.2, 2H), 7.10-7.06 (m, 2H), 6.84 (d, J=8.2, 2H), 6.38 (t, J=5.7, 1H), 4.43-4.28 (m, 2H), 4.22 (s, 2H), 3.71 (s, 3H), 3.71-3.67 (m, 2H), 2.51 (m, 2H), 2.38 (s, 3H).

Example 56

Preparation of N-(2,4-dichlorophenyl)-2-[(4-methoxybenzyl)amino]-3-(4-methylphenyl)-4-oxo-3,5,7,8-tetrahydropyrido[4,3-d]pyrimidine-6(4H)-carboxamide $^1$H-NMR (300 MHz, DMSO-d$_6$): δ (ppm)=8.43 (s, 1H), 7.59 (d, J=2.4, 1H), 7.52 (d, J=8.7, 1H), 7.39-7.34 (m, 3H), 7.17 (t, J=7.9, 4H), 6.84 (d, J=8.7, 2H), 6.38 (t, J=6.0, 1H), 4.35 (d, J=7.8, 2H), 4.22 (s, 2H), 3.71 (s, 3H), 3.71-3.66 (m, 2H), 2.54-2.49 (m, 2H), 2.40 (s, 3H).

Example 57

Preparation of N-(2,4-dichlorophenyl)-3-(3-chlorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.60-7.58 (m, 3H), 7.54-7.50 (m, 2H), 7.36 (dd, J=2.4, 8.7, 1H), 7.31-7.27 (m, 1H), 7.19 (d, J=8.6, 2H), 6.84 (d, J=8.6, 2H), 6.67 (t, J=5.9, 1H), 4.44-4.28 (m, 2H), 4.23 (s, 2H), 3.72 (s, 3H), 3.72-3.67 (m, 2H), 2.52-2.50 (m, 2H).

Example 58

Preparation of N-(2,4-dichlorophenyl)-3-(4-chlorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.64-7.59 (m, 3H), 7.52 (d, J=8.2, 1H), 7.38-7.34 (m, 3H), 7.19 (d, J=8.7, 2H), 6.84 (d, J=8.7, 2H), 6.65 (t, J=6.0, 1H), 4.35 (d, J=5.8, 2H), 4.23 (s, 2H), 3.72 (s, 3H), 3.72-3.68 (m, 2H), 2.52-2.49 (m, 2H).

Example 59

Preparation of N-(2,4-dichlorophenyl)-3-(2-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.60-7.37 (m, 7H), 7.18 (d, J=8.6, 2H), 6.95-6.86 (m, 1H), 6.85 (d, J=8.7, 2H), 4.37 (d, J=6.0, 2H), 4.23 (s, 2H), 3.72 (s, 3H), 3.72-3.69 (m, 2H), 2.54-2.49 (m, 2H).

Example 60

Preparation of N-(2,4-dichlorophenyl)-3-(3-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.65-7.58 (m, 2H), 7.52 (d, J=8.7, 1H), 7.41-7.29 (m, 3H), 7.18-7.15 (m, 3H), 6.85 (d, J=8.7, 2H), 6.63 (t, J=5.8, 1H), 4.37 (t, J=6.3, 2H), 4.23 (s, 2H), 3.72 (s, 3H), 3.72-3.66 (m, 2H), 2.54-2.49 (m, 2H).

Example 61

Preparation of N-(2,4-dichlorophenyl)-3-(4-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.60 (d, J=2.4, 1H), 7.52 (d, J=8.7, 1H), 7.40-7.34 (m, 5H), 7.19 (d, J=8.7, 2H), 6.84 (d, J=8.7, 2H), 6.58 (t, J=5.9, 1H), 4.36 (d, J=5.7, 2H), 4.23 (s, 2H), 3.71 (s, 3H), 3.71-3.66 (m, 2H), 2.54-2.49 (m, 2H).

Example 62

Preparation of N-(2,4-dichlorophenyl)-3-(4-aminophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.41 (s, 1H), 7.59 (d, J=2.4, 1H), 7.52 (d, J=8.7, 1H), 7.36 (dd, J=2.4, 8.7, 1H), 7.18 (d, J=8.6, 2H), 6.84 (dd, J=2.6, 8.7, 4H), 6.67 (d, J=8.6, 2H), 6.28 (t, J=6.0, 1H), 5.40 (s, 2H), 4.35 (d, J=5.8, 2H), 4.21 (s, 2H), 3.71 (s, 3H), 3.71-3.66 (m, 2H), 2.52-2.50 (m, 2H).

Example 63

Preparation of N-(2,4-dichlorophenyl)-3-(4-dimethylaminophenyl)-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=8.42 (s, 1H), 7.59 (d, J=2.4, 1H), 7.52 (d, J=8.7, 1H), 7.36 (dd, J=2.4, 8.7, 1H), 7.18 (d, J=8.6, 2H), 7.03 (d, J=8.9, 2H), 6.84 (d, J=8.6, 4H), 6.31 (t, J=5.8, 1H), 4.35 (d, J=5.9, 2H), 4.22 (s, 2H), 3.71 (s, 3H), 3.71-3.66 (m, 2H), 2.97 (s, 6H), 2.52-2.50 (m, 2H).

Example 64

Preparation of N-(2,4-dichlorophenyl)-3-(4-acetylamino-phenyl)-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=10.15 (br. s., NH), 8.42 (br. s., NH), 7.75 (d, J=8.8, 2H), 7.59 (d, J=2.4, 1H), 7.51 (d, J=8.7, 1H), 7.37 (dd, 1H), 7.16-7.19 (m, 4H), 6.84 (d, J=8.7, 2H), 6.45 (t, J=5.9, NH), 4.35 (d, J=5.9, 2H), 4.22 (s, 2H), 3.71 (s, 3H), 3.67 (m, 2H), 2.50 (m, 2H), 2.08 (s, 3H).

Example 65

Preparation of N-(2,4-dichlorophenyl)-2-[(4-methoxybenzyl)amino]-4-oxo-3-(4-sulfamoylphenyl)-3,5,7,8-tetrahydropyrido[4,3-d]pyrimidine-6(4H)-carboxamide $^1$H-NMR (300 MHz, DMSO-$d_6$): δ (ppm)=8.45 (br. s., NH), 7.97 (d, J=8.6, 2H), 7.59 (d, J=2.4, 1H), 7.50-7.53 (m, 5H), 7.35 (dd, J=2.4, 8.7, 1H), 7.19 (d, J=8.7, 2H), 6.84 (d, J=8.7, 2H), 6.73 (t, J=5.6, NH), 4.36 (d, J=5.6, 2H), 4.22 (s, 2H), 3.71 (s, 3H), 3.68 (t, J=5.2, 2H), 2.52 (m, 2H).

Example 66

Preparation of N-(2,4-dichlorophenyl)-3-(3-carboxyphenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-$d_6$): δ (ppm)=13.25 (br. s., OH), 8.48 (br. s., NH), 8.11-8.14 (m, 1H), 7.82 (s, 1H), 7.75 (t, J=7.9, 1H), 7.56-7.64 (m, 3H), 7.41 (dd, J=2.4, 8.7, 1H), 7.22 (d, J=8.7, 2H), 6.88 (d, J=8.7, 2H), 6.68 (t, J=5.9, NH), 4.33-4.48 (m, 2H), 4.28 (s, 2H), 3.76 (s, 3H), 3.72-3.74 (m, 2H), 2.59 (m, 2H).

Example 67

Preparation of N-(2,4-dichlorophenyl)-2-[(4-methoxybenzyl)amino]-4-oxo-3-(pyridin-3-yl)-3,5,7,8-tetrahydropyrido[4,3-d]-pyrimidine-6(4H)-carboxamide $^1$H-NMR (300 MHz, DMSO-$d_6$): δ (ppm)=8.69-8.72 (m, 1H), 8.51 (d, J=2.0, 1H), 8.44 (br. s., NH), 7.80 (m, 1H), 7.59-7.64 (m, 2H), 7.52 (d, J=8.7, 1H), 7.35 (dd, J=2.4, 8.7, 1H), 7.19 (d, J=8.7, 2H), 6.85 (dd, J=2.1, 6.7, 2H), 6.79 (t, J=5.7, NH), 4.36 (d, J=5.7, 2H), 4.23 (s, 2H), 3.71 (s, 3H), 3.69 (m, 2H), 2.54 (m, 2H).

Example 68

Preparation of N-(2,4-dichlorophenyl)-3-(benzo[1,3]dioxo-5-yl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-$d_6$): δ (ppm)=8.43 (br. s., NH), 7.59 (d, J=2.4, 1H), 7.51 (d, J=8.7, 1H), 7.35 (dd, J=2.4, 8.7, 1H), 7.19 (d, J=8.6, 2H), 7.05 (d, J=8.2, 1H), 6.91 (d, J=2.0, 1H), 6.83 (d, J=8.6, 2H), 6.73 (dd, J=2.1, 8.2, 1H), 6.59 (br. s., NH), 6.12 (s, 2H), 4.37 (m, 2H), 4.21 (s, 2H), 3.71 (s, 3H), 3.67 (t, J=5.1, 2H), 2.51 (m, 2H).

Example 69

Preparation of N-(2,4-dichlorophenyl)-2-[(4-methoxybenzyl)amino]-3-(naphthalen-2-yl)-4-oxo-3,5,7,8-tetrahydropyrido[4,3-d]pyrimidine-6(4H)-carboxamide $^1$H-NMR (300 MHz, DMSO-$d_6$): δ (ppm)=8.45 (br. s., NH), 8.10 (d, J=8.8, 1H), 7.99 (m, 2H), 7.93 (d, J=1.9, 1H), 7.59-7.64 (m, 3H), 7.53 (d, J=8.7, 1H), 7.33-7.38 (m, 2H), 7.18 (d, J=8.7, 2H), 6.82 (d, J=8.7, 2H), 6.67 (t, J=5.8, NH), 4.31-4.44 (m, 2H), 4.25 (s, 2H), 3.69-3.71 (m, 5H), 2.57 (t, J=4.5, 2H).

Example 70

Preparation of N-(2,4-dichlorophenyl)-2-[(4-methoxybenzyl)amino]-4-oxo-3-(thiophen-2-yl)-3,5,7,8-tetrahydropyrido[4,3-d]-pyrimidine-6(4H)-carboxamide $^1$H-NMR (300 MHz, DMSO-$d_6$): δ (ppm)=8.43 (br. s., NH), 7.73 (m, 1H), 7.58 (d, J=2.4, 1H), 7.52 (d, J=8.7, 1H), 7.35 (dd, J=2.4, 8.7, 1H), 7.12-7.22 (m, 4H), 6.91 (t, J=5.6, NH), 6.84 (d, J=8.6, 2H), 4.38 (d, J=5.6, 2H), 4.21 (s, 2H), 3.72 (s, 3H), 3.67 (t, J=5.5, 2H), 2.51 (m, 2H).

Example 71

Preparation of N-(2,4-dichlorophenyl)-2-[(4-methoxybenzyl)amino]-4-oxo-3-(n-propyl)-3,5,7,8-tetrahydropyrido[4,3-d]-pyrimidine-6(4H)-carboxamide $^1$H-NMR (300 MHz, DMSO-$d_6$): δ (ppm)=8.39 (br. s., NH), 7.56-7.59 (m, 2H), 7.52 (d, J=8.7, 1H), 7.35 (dd, J=2.4, 8.7, 1H), 7.25 (d, J=8.6, 2H), 6.87 (d, J=8.6, 2H), 4.48 (d, J=5.3, 2H), 4.20 (s, 2H), 3.90 (m, 2H), 3.72 (s, 3H), 3.67 (t, J=5.6, 2H), 2.47 (t, J=5.6, 2H), 1.53 (m, 2H), 0.90 (t, J=7.4, 3H).

Example 72

Preparation of N-(2,4-dichlorophenyl)-3-cyclohexyl-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=8.36 (br. s., NH), 7.59 (d, J=2.4, 1H), 7.53 (d, J=8.7, 1H), 7.35 (dd, J=2.4, 8.7, 1H), 7.24 (d, J=8.7, 2H), 6.88 (dd, J=2.1, 6.7, 2H), 4.48 (d, J=4.8, 2H), 4.16 (s, 2H), 3.72 (s, 3H), 3.61 (t, J=5.7, 2H), 2.51 (m, 2H), 2.43 (t, J=5.5, 2H), 1.76-1.80 (m, 2H), 1.22-1.64 (m, 8H).

Example 73

Preparation of N-(2,4-dichlorophenyl)-3-cyclopropyl-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=8.38 (br. s., NH), 7.59 (d, J=2.4, 1H), 7.52 (d, J=8.7, 1H), 7.41 (t, J=5.6, NH), 7.27-7.39 (m, 3H), 6.88 (d, J=8.6, 2H), 4.51 (d, J=5.6, 2H), 4.18 (s, 2H), 3.72 (s, 3H), 3.61 (t, J=5.5, 2H), 2.60 (m, 1H), 2.44 (m, 2H), 1.19 (m, 2H), 0.70 (m, 2H).

Example 74

Preparation of N-(2,4-dichlorophenyl)-2-[(4-methoxybenzyl)amino]-3-(4-nitrophenyl)-4-oxo-3,5,7,8-tetrahydropyrido[4,3-d]-pyrimidine-6(4H)-carboxamide $^1$H-NMR (300 MHz, DMSO-$d_6$): δ (ppm)=8.45 (br. s., NH), 8.40 (dd, J=2.0, 6.9, 2H), 7.65 (d, J=6.9, 2H), 7.59 (d, J=2.4, 1H), 7.51 (d, J=8.7, 1H), 7.34 (dd, J=2.4, 8.7, 1H), 7.19 (d, J=8.6, 2H), 6.83 (d, J=8.7, 2H), 6.70 (br. s., NH), 4.36 (m, 2H), 4.24 (s, 2H), 3.71 (s, 3H), 3.68 (t, J=5.7, 2H), 2.55 (m, 2H).

Example 75

Preparation of N-(3,4-difluorophenyl)-2-[(4-methoxybenzyl)amino]-4-oxo-3-(2-methoxyphenyl)-3,5,7,8-tetrahydropyrido[4,3-d]pyrimidine-6(4H)-carboxamide $^1$H-NMR (300 MHz, DMSO-$d_6$): δ (ppm)=8.89 (br. s, 1H), 7.66-7.59 (m, 1H), 7.54-7.48 (m, 1H), 7.30-7.08 (m, 7H), 6.85 (d, J=8.7, 2H), 6.50 (br. t, J=6.0, 1H), 4.47-4.40 (m, 1H), 4.30-4.22 (m, 3H), 3.75 (s, 3H), 3.71 (s, 3H), 3.69-3.64 (m, 2H).

Example 76

Preparation of N-(3,4-difluorophenyl)-2-[(4-methoxybenzyl)amino]-3-(3-methoxyphenyl)-4-oxo-3,5,7,8-tetrahydropyrido[4,3-d]pyrimidine-6(4H)-carboxamide $^1$H-NMR (300 MHz, DMSO-$d_6$): δ (ppm)=8.90 (br. s, 1H), 7.66-7.59 (m, 1H), 7.47 (t, J=8.1, 1H), 7.31-7.25 (m, 2H), 7.18 (d, J=8.7, 2H), 7.11-7.07 (m, 1H), 6.90 (t, J=2.1, 1H), 6.86-6.81 (m, 3H), 6.45 (br. t, J=6.0, 1H), 4.36 (br. t, J=5.1, 2H), 4.23 (br. s, 2H), 3.79 (s, 3H), 3.71 (s, 3H), 3.66 (br. t, J=5.5, 2H).

Example 77

Preparation of N-(3,4-difluorophenyl)-2-[(4-methoxybenzyl)amino]-3-(4-methoxyphenyl)-4-oxo-3,5,7,8-tetrahydropyrido[4,3-d]pyrimidine-6(4H)-carboxamide $^1$H-NMR (300 MHz, DMSO-$d_6$): δ (ppm)=8.89 (br. s, 1H), 7.66-7.59 (m, 1H), 7.30-7.25 (m, 2H), 7.20, 7.17 (AB, J=5.4, 4H), 7.10 (d, J=9.0, 2H), 6.84 (d, J=8.7, 2H), 6.44 (br. t, J=6.1, 1H), 4.35 (br. d, J=5.8, 2H), 4.22 (br. s, 2H), 3.83 (s, 3H), 3.71 (s, 3H), 3.66 (br. t, J=5.6, 2H).

Example 78

Preparation of N-(3,4-difluorophenyl)-2-[(4-methoxybenzyl)amino]-3-(3-methylphenyl)-4-oxo-3,5,7,8-tetrahydropyrido[4,3-d]pyrimidine-6(4H)-carboxamide $^1$H-NMR (300 MHz, DMSO-$d_6$): δ (ppm)=8.89 (br. s, 1H), 7.66-7.58 (m, 1H), 7.46 (t, J=7.7, 1H), 7.35-7.30 (m, 1H), 7.27-7.22 (m, 2H), 7.18 (d, J=8.7, 2H), 7.15-7.05 (m, 2H), 6.84 (d, J=8.7, 2H), 6.37 (br. t, J=6.0, 1H), 4.43-4.27 (m, 2H), 4.22 (br. s, 2H), 3.71 (s, 3H), 3.67 (br. t, J=5.7, 2H), 2.37 (s, 3H).

Example 79

Preparation of N-(3,4-difluorophenyl)-2-[(4-methoxybenzyl)amino]-3-(4-methylphenyl)-4-oxo-3,5,7,8-tetrahydropyrido[4,3-d]pyrimidine-6(4H)-carboxamide $^1$H-NMR (300 MHz, DMSO-$d_6$): δ (ppm)=8.89 (br. s, 1H), 7.66-7.59 (m, 1H), 7.37 (d, J=8.0, 2H), 7.30-7.25 (m, 2H), 7.18, 7.15 (AB, J=6.2, 4H), 6.83 (d, J=8.7, 2H), 6.37 (t, J=6.0, 1H), 4.35 (br. d, J=5.8, 2H), 4.22 (br. s, 2H), 3.71 (s, 3H), 3.67 (br. t, J=5.6, 2H), 2.40 (s, 3H).

Example 80

Preparation of N-(3,4-difluorophenyl)-3-(3-chlorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-$d_6$): δ (ppm)=8.90 (br. s, 1H), 7.66-7.56 (m, 3H), 7.49 (br. s, 1H), 7.34-7.25 (m, 3H), 7.19 (d, J=8.6, 2H), 6.84 (d, J=8.6, 2H), 6.66 (br. t, J=5.8, 1H), 4.44-4.28 (m, 2H), 4.23 (br. s, 2H), 3.71 (s, 3H), 3.67 (br. t, J=5.7, 2H).

Example 81

Preparation of N-(3,4-difluorophenyl)-3-(4-chlorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-$d_6$): δ (ppm)=8.90 (br. s, 1H), 7.66-7.58 (m, 3H), 7.35 (d, J=8.7, 2H), 7.30-7.21 (m, 2H), 7.18 (d, J=8.7, 2H), 6.84 (d, J=8.7, 2H), 6.64 (br. t, J=5.9, 1H), 4.35 (br. d, J=5.8, 2H), 4.23 (br. s, 2H), 3.71 (s, 3H), 3.67 (br. t, J=5.7, 2H).

Example 82

Preparation of N-(3,4-difluorophenyl)-3-(2-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-$d_6$): δ (ppm)=8.90 (br. s, 1H), 7.66-7.56 (m, 2H), 7.50-7.34 (m, 3H), 7.31-7.25 (m, 2H), 7.18 (d, J=8.7, 2H), 6.92-6.87 (m, 1H), 6.85 (d, J=8.7, 2H), 4.37 (br. d, J=5.7, 2H), 4.23 (br. s, 2H), 3.71 (s, 3H), 3.68 (br. t, J=5.7, 2H).

Example 83

Preparation of N-(3,4-difluorophenyl)-3-(3-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.91 (br. s, 1H), 7.66-7.58 (m, 2H), 7.41-7.22 (m, 4H), 7.20-7.15 (m, 3H), 6.84 (d, J=8.7, 2H), 6.62 (br. t, J=6.0, 1H), 4.36 (br. t, J=6.3, 2H), 4.23 (br. s, 2H), 3.71 (s, 3H), 3.67 (br. t, J=5.7, 2H).

Example 84

Preparation of N-(3,4-difluorophenyl)-3-(4-fluorophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.90 (br. s, 1H), 7.66-7.58 (m, 1H), 7.40-7.35 (m, 4H), 7.30-7.23 (m, 2H), 7.18 (d, J=8.7, 2H), 6.84 (d, J=8.7, 2H), 6.57 (br. t, J=6.0, 1H), 4.35 (br. d, J=5.9, 2H), 4.23 (br. s, 2H), 3.71 (s, 3H), 3.67 (br. t, J=5.6, 2H).

Example 85

Preparation of N-(3,4-difluorophenyl)-3-(4-aminophenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.88 (br. s, 1H), 7.66-7.58 (m, 1H), 7.30-7.25 (m, 2H), 7.17 (d, J=8.6, 2H), 6.87-6.82 (m, 4H), 6.67 (d, J=8.6, 2H), 6.28 (br. t, J=6.0, 1H), 5.40 (br. s, 2H), 4.35 (br. d, J=5.8, 2H), 4.21 (br. s, 2H), 3.71 (s, 3H), 3.66 (br. t, J=5.5, 2H).

Example 86

Preparation of N-(3,4-difluorophenyl)-3-(4-dimethylaminophenyl)-2-[(4-methoxybenzyl)amino]-4-oxo-3,5,7,8-tetrahydropyrido[4,3-d]pyrimidine-6(4H)-carboxamide $^1$H-NMR (300 MHz, DMSO-d$_6$): δ (ppm)=8.89 (br. s, 1H), 7.66-7.58 (m, 1H), 7.30-7.25 (m, 2H), 7.18 (d, J=8.6, 2H), 7.03 (d, J=8.9, 2H), 6.84 (d, J=8.8, 4H), 6.30 (br. t, J=6.0, 1H), 4.35 (br. d, J=5.8, 2H), 4.22 (br., s, 2H), 3.71 (s, 3H), 3.66 (br. t, J=5.7, 2H), 2.97 (s, 6H).

Example 87

Preparation of N-(3,4-difluorophenyl)-3-(4-acetylamino-phenyl)-2-[(4-methoxybenzyl)amino]-4-oxo-3,5,7,8-tetrahydropyrido[4,3-d]pyrimidine-6(4H)-carboxamide $^1$H-NMR (300 MHz, DMSO-d$_6$): δ (ppm)=10.14 (s, 1H), 8.88 (s, 1H), 7.75 (d, J=8.7, 2H), 7.70-7.55 (m, 1H), 7.26 (d, J=6.9, 2H), 7.20-7.16 (m, 4H), 6.83 (d, J=8.6, 2H), 6.43 (t, 1H), 4.34 (d, J=5.8, 2H), 4.22 (s, 2H), 3.71 (s, 3H), 3.66 (m, 2H), 2.54-2.49 (m, 2H), 2.08 (s, 3H).

Example 88

Preparation of N-(3,4-difluorophenyl)-2-[(4-methoxybenzyl)amino]-4-oxo-3-(4-sulfamoylphenyl)-3,5,7,8-tetrahydropyrido-[4,3-d]pyrimidine-6(4H)-carboxamide $^1$H-NMR (300 MHz, DMSO-d$_6$): δ (ppm)=8.90 (s, 1H), 7.97 (d, J=8.5, 2H), 7.65-7.53 (m, 1H), 7.51 (d, J=8.5, 4H), 7.26 (d, J=9.0, 2H), 7.18 (d, J=8.6, 2H), 6.84 (d, J=8.7, 2H), 6.71 (m, 1H), 4.35 (d, J=5.6, 2H), 4.22 (s, 2H), 3.71 (s, 3H), 3.66 (t, 2H), 2.54-2.49 (m, 2H).

Example 89

Preparation of N-(3,4-difluorophenyl)-3-(3-carboxyphenyl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=13.20 (br. s, 1H), 8.90 (s, 1H), 8.07 (d, J=10.4, 1H), 7.77 (s, 1H), 7.76-7.54 (m, 3H), 7.24 (d, J=8.9, 2H), 7.17 (d, J=8.6, 2H), 6.83 (d, J=8.7, 2H), 6.62 (t, J=5.9, 6, 1H), 4.38 (m, 2H), 4.23 (s, 2H), 3.71 (s, 3H), 3.66 (t, 2H), 2.54-2.49 (m, 2H).

Example 90

Preparation of N-(3,4-difluorophenyl)-2-[(4-methoxybenzyl)amino]-4-oxo-3-(pyridin-3-yl)-3,5,7,8-tetrahydropyrido[4,3-d]-pyrimidine-6(4H)-carboxamide $^1$H-NMR (300 MHz, DMSO-d$_6$): δ (ppm)=8.90 (s, 1H), 8.71-8.69 (d, J=6.3, 1H), 8.51 (s, 1H), 7.83-7.79 (m, 1H), 7.63-7.58 (m, 2H), 7.26 (d, J=6.2, 2H), 7.18 (d, J=8.7, 2H), 6.84 (d, J=8.7, 2H), 6.79 (t, 1H), 4.36 (d, J=5.6, 2H), 4.23 (s, 2H), 3.71 (s, 3H), 3.66 (t, 2H), 2.54-2.49 (m, 2H).

Example 91

Preparation of N-(3,4-difluorophenyl)-3-(benzo[1,3]dioxo-5-yl)-2-[(4-methoxybenzyl)amino]-4-oxo-3,5,7,8-tetrahydropyrido[4,3-d]-pyrimidine-6(4H)-carboxamide $^1$H-NMR (300 MHz, DMSO-d$_6$): δ (ppm)=8.89 (s, 1H), 7.65-7.58 (m, 1H), 7.25 (d, J=6.4, 2H), 7.18 (d, J=8.6, 2H), 7.05 (d, J=8.1, 1H), 6.91 (d, J=2, 1H), 6.83 (d, J=8.6, 2H), 6.74 (d, J=8.1, 2H), 6.58 (t, J=5.8, 6.1, 1H), 6.12 (s, 2H), 4.36 (m, 2H), 4.22 (s, 2H), 3.71 (s, 3H), 3.65 (t, J=5.3, 5.4, 2H), 2.54-2.49 (m, 2H).

Example 92

Preparation of N-(3,4-difluorophenyl)-2-[(4-methoxybenzyl)amino]-3-(naphthalen-2-yl)-4-oxo-3,5,7,8-tetrahydropyrido[4,3-d]pyrimidine-6(4H)-carboxamide $^1$H-NMR (300 MHz, DMSO-d$_6$): δ (ppm)=8.91 (s, 1H), 8.10 (d, J=8.7, 1H), 8.06-7.99 (m, 1H), 7.92 (d, J=1.8, 1H), 7.66-7.60 (m, 3H), 7.35 (d, J=10.6, 1H), 7.26 (d, J=5.0, 2H), 7.17 (d, J=8.6, 2H), 6.83 (d, J=8.7, 2H), 6.66 (t, 1H), 4.34 (m, 2H), 4.25 (s, 2H), 3.70 (s, 3H), 3.68 (t, 2H), 2.54-2.49 (m, 2H).

Example 93

Preparation of N-(3,4-difluorophenyl)-2-[(4-methoxybenzyl)amino]-4-oxo-3-(thiophen-2-yl)-3,5,7,8-tetrahydropyrido[4,3-d]-pyrimidine-6(4H)-carboxamide $^1$H-NMR (300 MHz, DMSO-$d_6$): δ (ppm)=8.88 (s, 1H), 7.73 (d, J=5.4, 1H), 7.65-7.58 (m, 1H), 7.30-7.12 (m, 6H), 6.92 (t, 1H), 6.84 (d, J=8.6, 2H), 4.38 (d, J=5.8, 2H), 4.22 (s, 2H), 3.71 (s, 3H), 3.65 (t, $J_1$=5.1, $J_2$=5.5, 2H), 2.54-2.49 (m, 2H).

Example 94

Preparation of N-(3,4-difluorophenyl)-2-[(4-methoxybenzyl)amino]-4-oxo-3-propyl-3,5,7,8-tetrahydropyrido[4,3-d]-pyrimidine-6(4H)-carboxamide $^1$H-NMR (300 MHz, DMSO-$d_6$): δ (ppm)=8.85 (s, 1H), 7.65-7.56 (m, 2H), 7.30-7.23 (m, 4H), 6.87 (d, J=8.7, 2H), 4.48 (d, J=5.4, 2H), 4.20 (s, 2H), 3.87 (t, $J_1$=7.5, $J_2$=7.7, 2H), 3.72 (s, 3H), 3.61 (t, $J_1$=5.7, $J_2$=5.7, 2H), 2.46 (m, 2H), 1.55 (m, 2H), 0.89 (t, $J_1$=7.2, $J_2$=7.4, 3H).

Example 95

Preparation of N-(3,4-difluorophenyl)-3-cyclohexyl-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=8.84 (s, 1H), 7.65-7.40 (m, 2H), 7.26-7.23 (m, 4H), 6.87 (d, J=8.7, 2H), 4.47 (d, J=5.1, 2H), 4.30 (m, 1H), 4.16 (s, 2H), 3.71 (s, 3H), 3.60 (t, $J_1$=5.6, $J_2$=5.7, 2H), 2.54-2.49 (m, 2H), 2.39 (t, $J_1$=5.3, $J_2$=5.7, 2H), 1.80-1.20 (m, 8H).

Example 96

Preparation of N-(3,4-difluorophenyl)-3-cyclopropyl-2-[(4-methoxybenzyl)amino]-4-oxo-3,5,7,8-tetrahydropyrido[4,3-d]pyrimidine-6(4H)-carboxamide $^1$H-NMR (300 MHz, DMSO-$d_6$): δ (ppm)=8.84 (s, 1H), 7.65-7.58 (m, 1H), 7.41 (t, $J_1$=5.5, $J_2$=5.8, 1H), 7.30-7.24 (m, 4H), 6.88 (d, J=8.5, 2H), 4.50 (d, J=5.5, 2H), 4.17 (s, 2H), 3.72 (s, 3H), 3.60 (t, $J_1$=5.5, $J_2$=5.5, 2H), 2.60-2.57 (m, 1H), 2.44 (t, 2H), 1.21 (m, 2H), 0.73 (m, 2H).

Example 97

Preparation of N-(3,4-difluorophenyl)-2-[(4-methoxybenzyl)amino]-3-(4-nitrophenyl)-4-oxo-3,5,7,8-tetrahydropyrido[4,3-d]-pyrimidine-6(4H)-carboxamide $^1$H-NMR (300 MHz, DMSO-$d_6$): δ (ppm)=8.90 (s, 1H), 8.41 (d, J=8.9, 2H), 7.66 (d, J=8.8, 2H), 7.64-7.58 (m, 1H), 7.26 (d, J=6.4, 2H), 7.18 (d, J=8.5, 2H), 6.84 (d, J=8.6, 2H), 6.69 (t, 1H), 4.35 (d, J=5.2, 2H), 4.24 (s, 2H), 3.71 (s, 3H), 3.67 (t, 2H), 2.54-2.49 (m, 2H).

Example 98

Preparation of N-(2,4-dichlorophenyl)-2-benzylamino-4-oxo-3-phenyl-3,5,7,8-tetrahydropyrido[4,3-d]pyrimidine-6(4H)-carboxamide $^1$H-NMR (400 MHz, DMSO-$d_6$): δ (ppm)=8.45 (s, 1H), 7.60-7.48 (m, 5H), 7.36-7.17 (m, 8H), 6.50 (d, J=8.0, 1H), 4.43 (d, J=8.0, 2H), 4.21 (s, 2H), 3.66 (t, J=4.0, 2H), 2.53-2.46 (m, 2H).

Example 99

Preparation of N-(2,4-dichlorophenyl)-2-[(2-methoxybenzyl)amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.43 (s, 1H), 7.63-7.50 (m, 5H), 7.38-7.33 (m, 3H), 7.20 (t, J=7.2, 1H), 7.10 (d, J=7.2, 1H), 6.94 (d, J=7.7, 1H), 6.88 (t, J=7.3, 1H), 6.04 (t, J=5.8, 1H), 4.42 (d, J=5.7, 2H), 4.23 (s, 2H), 3.72 (s, 3H), 3.67 (t, J=5.6, 2H), 2.51-2.49 (m, 2H).

Example 100

Preparation of N-(2,4-dichlorophenyl)-2-[(3-methoxybenzyl)amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.43 (s, 1H), 7.61-7.50 (m, 5H), 7.37-7.31 (m, 3H), 7.19 (t, J=8.0, 1H), 6.82-6.75 (m, 3H), 6.45 (t, J=6.0, 1H), 4.41 (d, J=5.7, 2H), 4.23 (s, 2H), 3.72 (s, 3H), 3.68 (t, J=5.6, 2H), 2.51-2.49 (m, 2H).

Example 101

Preparation of N-(2,4-dichlorophenyl)-2-[(3-methylbenzyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.43 (s, 1H), 7.61-7.50 (m, 5H), 7.37-7.31 (m, 3H), 7.16 (t, J=7.2, 1H), 7.04-7.02 (m, 3H), 6.42 (t, J=5.8, 1H), 4.41 (d, J=5.7, 2H), 4.23 (s, 2H), 3.68 (t, J=5.5, 2H), 2.51-2.49 (m, 2H), 2.27 (s, 3H).

Example 102

Preparation of N-(2,4-dichlorophenyl)-2-[(4-methylbenzyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.43 (s, 1H), 7.60-7.50 (m, 5H), 7.37-7.29 (m, 3H), 7.13 (d, J=8.2, 2H), 7.08 (d, J=8.2, 2H), 6.42 (t, J=5.8, 1H), 4.39 (d, J=5.6, 2H), 4.22 (s, 2H), 3.68 (t, J=5.6, 2H), 2.51-2.49 (m, 2H), 2.25 (s, 3H).

Example 103

Preparation of N-(2,4-dichlorophenyl)-2-[(3-chlorobenzyl)amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.44 (s, 1H), 7.62-7.50 (m, 5H), 7.37-7.21 (m, 7H), 6.55 (t, J=6.0, 1H), 4.42 (d, J=5.5, 2H), 4.22 (s, 2H), 3.68 (t, J=5.5, 2H), 2.51-2.49 (m, 2H).

Example 104

Preparation of N-(2,4-dichlorophenyl)-2-[(4-chlorobenzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=8.43 (s, 1H), 7.59-7.50 (m, 5H), 7.37-7.25 (m, 7H), 6.54 (t, J=5.8, 1H), 4.40 (d, J=5.8, 2H), 4.22 (s, 2H), 3.67 (t, J=5.4, 2H), 2.51-2.49 (m, 2H).

Example 105

Preparation of N-(2,4-dichlorophenyl)-2-[(2-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-d$_6$): δ (ppm)=8.43 (s, 1H), 7.63-7.50 (m, 5H), 7.37-7.33 (m, 3H), 7.30-7.23 (m, 2H), 7.16-7.09 (m, 2H), 6.44 (t, J=5.8, 1H), 4.49 (d, J=5.7, 2H), 4.23 (s, 2H), 3.67 (t, J=5.7, 2H), 2.51-2.49 (m, 2H).

Example 106

Preparation of N-(2,4-dichlorophenyl)-2-[(3-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-d$_6$): δ (ppm)=8.44 (s, 1H), 7.62-7.50 (m, 5H), 7.37-7.29 (m, 4H), 7.10-7.02 (m, 3H), 6.54 (t, J=5.6, 1H), 4.44 (d, J=5.5, 2H), 4.23 (s, 2H), 3.67 (t, J=5.5, 2H), 2.51-2.49 (m, 2H).

Example 107

Preparation of N-(2,4-dichlorophenyl)-2-[(4-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-d$_6$): δ (ppm)=8.43 (s, 1H), 7.61-7.50 (m, 5H), 7.37-7.26 (m, 5H), 7.12-7.06 (m, 2H), 6.53 (t, J=5.9, 1H), 4.40 (d, J=5.7, 2H), 4.23 (s, 2H), 3.68 (t, J=5.6, 2H), 2.51-2.49 (m, 2H).

Example 108

Preparation of N-(2,4-dichlorophenyl)-4-oxo-3-phenyl-2-[(pyridin-2-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 8.41 (d, J=4.7, 1H), 7.72 (td, J=1.8, J=7.6, 1H), 7.63-7.50 (m, 5H), 7.41-7.20 (m, 5H), 6.48 (t, J=5.6, 1H), 4.53 (d, J=5.4, 2H), 4.24 (s, 2H), 3.67 (t, J=5.6, 2H), 2.51-2.49 (m, 2H).

Example 109

Preparation of N-(2,4-dichlorophenyl)-4-oxo-3-phenyl-2-[(pyridin-3-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.48 (d, J=1.68, 1H), 8.43-8.40 (m, 2H), 7.67-7.50 (m, 6H), 7.37-7.29 (m, 4H), 6.58 (t, J=5.8, 1H), 4.43 (d, J=5.8, 2H), 4.22 (s, 2H), 3.68 (t, J=5.6, 2H), 2.51-2.49 (m, 2H).

Example 110

Preparation of N-(2,4-dichlorophenyl)-4-oxo-3-phenyl-2-[(pyridin-4-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.47-8.43 (m, 3H), 7.63-7.49 (m, 5H), 7.40-7.33 (m, 3H), 7.23 (d, J=5.9, 2H), 6.58 (t, J=5.8, 1H), 4.44 (d, J=5.7, 2H), 4.23 (s, 2H), 3.66 (t, J=5.5, 2H), 2.51-2.49 (m, 2H).

Example 111

Preparation of N-(2,4-dichlorophenyl)-2-[(3-dimethyl-methylaminobenzyl)amino]-4-oxo-3-phenyl-3,5,7,8-tetrahydropyrido-[4,3-d]pyrimidine-6(4H)-carboxamide $^1$H-NMR (300 MHz, DMSO-d$_6$): δ (ppm)=8.43 (s, 1H), 7.61-7.50 (m, 5H), 7.37-7.30 (m, 3H), 7.07 (t, J=7.8, 1H), 6.60-6.51 (m, 3H), 6.33 (t, J=5.9, 1H), 4.38 (d, J=5.7, 2H), 4.23 (s, 2H), 3.68 (t, J=5.5, 2H), 2.86 (s, 6H), 2.51-2.49 (m, 2H).

Example 112

Preparation of N-(2,4-dichlorophenyl)-2-[(3-acetylamino-benzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=9.84 (s, 1H), 8.43 (s, 1H), 7.61-7.34 (m, 10H), 7.18 (t, J=7.8, 1H), 6.90 (d, J=7.6, 1H), 6.48 (t, J=6.0, 1H), 4.41 (d, J=5.8, 2H), 4.23 (s, 2H), 3.68 (t, J=5.5, 2H), 2.51-2.50 (m, 2H), 2.03 (s, 3H).

Example 113

Preparation of N-(2,4-dichlorophenyl)-2-[(3-carboxy-benzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=12.90 (broad s, 1H), 8.43 (s, 1H), 7.88 (s, 1H), 7.79 (d, J=7.6, 1H), 7.65-7.45 (m, 6H), 7.45-7.25 (m, 4H), 6.60 (t, J=6.0, 1H), 4.48 (d, J=6.0, 2H), 4.22 (s, 2H), 3.68 (t, J=5.4, 2H), 2.54-2.49 (m, 2H).

Example 114

Preparation of N-(2,4-dichlorophenyl)-2-[(benzo[1,3]dioxo-5-ylmethyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=8.44 (s, 1H), 7.65-7.50 (m, 5H), 7.40-7.30 (m, 3H), 6.83 (m, 2H), 6.75 (m, 1H), 6.40 (t, J=5.7, 1H), 5.96 (s, 2H), 4.33 (d, J=5.5, 2H), 4.23 (s, 2H), 3.69 (t, J=5.5, 2H), 2.54-2.49 (m, 2H).

Example 115

Preparation of N-(2,4-dichlorophenyl)-2-[(4-methoxyphenyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.46 (s, 1H), 7.65-7.50 (m, 6H), 7.45-7.35 (m, 3H), 7.25 (d, J=8.9, 2H), 6.85 (d, J=8.9, 2H), 4.26 (s, 2H), 3.73 (s, 3H), 3.69 (m, 2H), 2.54-2.49 (m, 2H).

Example 116

Preparation of N-(2,4-dichlorophenyl)-4-oxo-3-phenyl-2-phenylamino-3,5,7,8-tetrahydropyrido[4,3-d]pyrimidine-6(4H)-carboxamide $^1$H-NMR (300 MHz, DMSO-$d_6$): δ (ppm)=8.48 (s, 1H), 7.65-7.50 (m, 6H), 7.45-7.35 (m, 5H), 7.27 (t, J=7.7, 2H), 7.07 (t, J=7.1, 1H), 4.28 (s, 2H), 3.71 (t, J=5.5, 2H), 2.54-2.49 (m, 2H).

Example 117

Preparation of N-(2,4-dichlorophenyl)-4-oxo-3-phenyl-2-[(thiophen-2-ylmethyl)amino]-3,5,7,8-tetrahydropyrido[4,3-d]-pyrimidine-6(4H)-carboxamide $^1$H-NMR (300 MHz, DMSO-$d_6$): δ (ppm)=8.46 (s, 1H), 7.60-7.50 (m, 5H), 7.40-7.30 (m, 2H), 7.26 (m, 2H), 6.91 (m, 2H), 6.59 (m, 1H), 4.56 (d, J=5.6, 2H), 4.24 (s, 2H), 3.72 (t, J=5.6, 2H), 2.60 (m, 2H).

Example 118

Preparation of N-(2,4-dichlorophenyl)-2-[(furan-2-ylmethyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.45 (s, 1H), 7.60-7.50 (m, 5H), 7.37 (dd, J=2.4, 8.7, 1H), 7.29 (m, 2H), 6.35 (m, 2H), 6.20 (m, 1H), 4.41 (d, J=5.2, 2H), 4.24 (s, 2H), 3.70 (t, J=5.4, 2H), 2.56 (m, 2H).

Example 119

Preparation of N-(2,4-dichlorophenyl)-2-cyclohexylamino-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.44 (s, 1H), 7.65-7.50 (m, 5H), 7.36 (dd, J=8.7, 2.4, 1H), 7.30 (m, 2H), 4.96 (d, J=8.1, 1H), 4.23 (s, 2H), 3.86 (br. s, 1H), 3.70 (t, J=5.6, 2H), 2.57 (m, 2H), 1.80-1.70 (m, 2H), 1.53 (m, 2H), 1.30-1.00 (m. 6H).

Example 120

Preparation of N-(2,4-dichlorophenyl)-2-(tert-butylamino)-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.46 (s, 1H), 7.65-7.50 (m, 5H), 7.40-7.30 (m, 3H), 4.25 (s, 2H), 4.11 (s, 1H), 3.72 (t, J=5.7, 2H), 2.61 (m, 2H), 1.29 (s, 9H).

Example 121

Preparation of N-(2,4-dichlorophenyl)-2-[(cyclohexylmethyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.44 (s, 1H), 7.65-7.50 (m, 5H), 7.36 (dd, J=8.7, 2.4, 1H), 7.27 (d, J=6.7, 2H), 5.67 (t, J=5.5, 1H), 4.23 (s, 2H), 3.70 (t, J=5.5, 2H), 3.08 (t, J=5.9, 2H), 2.54-2.49 (m, 2H), 1.70-1.50 (m, 6H), 1.15-1.10 (m, 3H), 0.90-0.75 (m, 2H).

Example 122

Preparation of N-(2,4-dichlorophenyl)-2-(2,2-dimethylpropylamino)-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.45 (s, 1H), 7.65-7.50 (m, 5H), 7.40-7.30 (m, 3H), 5.12 (t, J=6.1, 1H), 4.24 (s, 2H), 3.70 (t, J=5.7, 2H), 3.13 (d, J=6.0, 2H), 2.55 (m, 2H), 0.76 (s, 9H).

Example 123

Preparation of N-(2,4-dichlorophenyl)-4-oxo-3-phenyl-2-(n-propylamino)-3,5,7,8-tetrahydropyrido[4,3-d]pyrimidine-6(4H)-carboxamide $^1$H-NMR (300 MHz, DMSO-$d_6$): δ (ppm)=8.44 (s, 1H), 7.65-7.50 (m, 5H), 7.36 (dd, J=2.4, 8.7, 1H), 7.26 (m, 2H), 5.78 (t, J=5.7, 1H), 4.23 (s, 2H), 3.70 (t, J=5.5, 2H), 3.17 (m, 2H), 2.56 (m, 2H), 1.46 (m, 2H), 0.77 (t, J=7.4, 3H).

Example 124

Preparation of N-(2,4-dichlorophenyl)-4-oxo-3-phenyl-2-(piperidin-1-yl)-3,5,7,8-tetrahydropyrido[4,3-d]pyrimidine-6(4H)-carboxamide $^1$H-NMR (300 MHz, DMSO-$d_6$): δ (ppm)=8.49 (s, 1H), 7.60 (m, 1H), 7.51 (m, 3H), 7.45-7.35 (m, 4H), 4.27 (s, 2H), 3.72 (t, J=5.6, 2H), 2.99 (t, J=5.3, 4H), 2.61 (m, 2H), 1.34 (m, 2H), 1.15 (m, 4H).

Example 125

Preparation of N-(2,4-dichlorophenyl)-2-(3,4-dihydro-1H-isoquinolin-2-yl)-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.51 (s, 1H), 7.60 (d, J=2.3, 1H), 7.55-7.35 (m, 7H), 7.09 (m, 3H), 7.00 (m, 1H), 4.31 (s, 2H), 4.30 (s, 2H), 3.74 (t, J=5.5, 2H), 3.20 (t, J=5.5, 2H), 2.67 (m, 2H), 2.17 (m, 2H).

Example 126

Preparation of N-(2,4-dichlorophenyl)-2-(benzylmethylamino)-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.50 (s, 1H), 7.61 (d, J=2.4, 1H), 7.55-7.45 (m, 3H), 7.45-7.35 (m, 4H), 7.30-7.20 (m, 3H), 7.10 (m, 2H), 4.30 (s, 2H), 4.28 (s, 2H), 3.73 (t, J=5.7, 2H), 2.63 (m, 2H), 2.32 (s, 3H).

Example 127

Preparation of N-(2,4-dichlorophenyl)-4-oxo-2-phenethylamino-3-phenyl-3,5,7,8-tetrahydropyrido[4,3-d]pyrimidine-6(4H)-carboxamide $^1$H-NMR (300 MHz, DMSO-$d_6$): δ (ppm)=8.45 (s, 1H), 7.60 (d, J=2.4, 1H), 7.55-7.50 (m, 4H), 7.40-7.35 (m, 1H), 7.30-7.10 (m, 7H), 5.72 (t, J=5.5, 1H), 4.24 (s, 2H), 3.71 (t, J=5.5, 2H), 3.43 (m, 2H), 2.76 (t, J=7.2, 2H), 2.60 (m, 2H).

Example 128

Preparation of N-(2,4-dichlorophenyl)-2-[(3-aminobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.43 (s, 1H), 7.61-7.50 (m, 5H), 7.37-7.32 (m, 3H), 6.90 (t, J=7.6, 1H), 6.87-6.33 (m, 3H), 6.28 (t, J=5.7, 1H), 4.97 (broad s, 2H), 4.32 (d, J=5.8, 2H), 4.23 (s, 2H), 3.68 (t, J=5.6, 2H), 2.51-2.49 (m, 2H).

Example 129

Preparation of N-(3,4-difluorophenyl)-2-benzylamino-4-oxo-3-phenyl-3,5,7,8-tetrahydropyrido[4,3-d]pyrimidine-6(4H)-carboxamide $^1$H-NMR (400 MHz, DMSO-$d_6$): δ (ppm)=8.90 (s, 1H), 7.64-7.50 (m, 4H), 7.33-7.17 (m, 9H), 6.49 (d, J=4.0, 1H), 4.42 (d, J=4.0, 2H), 4.22 (s, 2H), 3.65 (t, J=4.0, 2H), 2.53-2.46 (m, 2H).

Example 130

Preparation of N-(3,4-difluorophenyl)-2-[(2-methoxybenzyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.89 (s, 1H), 7.67-7.54 (m, 4H), 7.38-7.35 (m, 2H), 7.32-7.18 (m, 3H), 7.09 (d, J=7.3, 1H), 6.95-6.85 (m, 2H), 6.04 (t, J=5.6, 1H), 4.41 (d, J=5.5, 2H), 4.24 (s, 2H), 3.72 (s, 3H), 3.66 (t, J=5.7, 2H), 2.52-2.49 (m, 2H).

Example 131

Preparation of N-(3,4-difluorophenyl)-2-[(3-methoxybenzyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.90 (s, 1H), 7.66-7.53 (m, 4H), 7.33-7.16 (m, 5H), 6.82-6.74 (m, 3H), 6.44 (t, J=5.8, 1H), 4.41 (d, J=5.5, 2H), 4.23 (s, 2H), 3.72 (s, 3H), 3.67 (t, J=5.5, 2H), 2.52-2.45 (m, 2H).

Example 132

Preparation of N-(3,4-difluorophenyl)-2-[(3-methylbenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.66-7.50 (m, 4H), 7.34-7.24 (m, 4H), 7.16 (t, J=7.5, 1H), 7.02 (m, 3H), 6.41 (t, J=6.0, 1H), 4.40 (d, J=5.7, 2H), 4.23 (s, 2H), 3.67 (t, J=5.7, 2H), 2.52-2.45 (m, 2H), 2.27 (s, 3H).

Example 133

Preparation of N-(3,4-difluorophenyl)-2-[(4-methylbenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.66-7.51 (m, 4H), 7.32-7.22 (m, 4H), 7.12 (d, J=8.2, 2H), 7.07 (d, J=8.2, 2H), 6.40 (t, J=5.8, 1H), 4.38 (d, J=5.6, 2H), 4.23 (s, 2H), 3.66 (t, J=5.6, 2H), 2.53-2.45 (m, 2H), 2.25 (s, 3H).

Example 134

Preparation of N-(3,4-difluorophenyl)-2-[(3-chlorobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.66-7.51 (m, 4H), 7.35-7.21 (m, 8H), 6.54 (t, J=5.9, 1H), 4.42 (d, J=5.6, 2H), 4.23 (s, 2H), 3.67 (t, J=5.6, 2H), 2.53-2.45 (m, 2H).

Example 135

Preparation of N-(3,4-difluorophenyl)-2-[(4-chlorobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.66-7.51 (m, 4H), 7.28-7.25 (m, 8H), 6.53 (t, J=6.1, 1H), 4.40 (d, J=5.5, 2H), 4.23 (s, 2H), 3.66 (t, J=5.4, 2H), 2.52-2.45 (m, 2H).

Example 136

Preparation of N-(3,4-difluorophenyl)-2-[(2-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.89 (s, 1H), 7.66-7.52 (m, 4H), 7.37-7.34 (m, 2H), 7.30-7.23 (m, 4H), 7.16-7.09 (m, 2H), 6.44 (t, J=5.8, 1H), 4.48 (d, J=5.6, 2H), 4.23 (s, 2H), 3.65 (t, J=5.5, 2H), 2.52-2.45 (m, 2H).

Example 137

Preparation of N-(3,4-difluorophenyl)-2-[(3-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.66-7.51 (m, 4H), 7.36-7.25 (m, 5H), 7.10-6.99 (m, 3H), 6.53 (t, J=6.0, 1H), 4.44 (d, J=5.5, 2H), 4.23 (s, 2H), 3.66 (t, J=5.6, 2H), 2.52-2.45 (m, 2H).

Example 138

Preparation of N-(3,4-difluorophenyl)-2-[(4-fluorobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.67-7.52 (m, 4H), 7.33-7.25 (m, 6H), 7.12-7.06 (m, 2H), 6.50 (t, J=5.9, 1H), 4.40 (d, J=5.4, 2H), 4.23 (s, 2H), 3.67 (t, J=5.4, 2H), 2.52-2.45 (m, 2H).

Example 139

Preparation of N-(3,4-difluorophenyl)-4-oxo-3-phenyl-2-[(pyridin-2-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.90 (s, 1H), 8.80 (d, J=5.0, 1H), 7.76-7.70 (m, 1H), 7.69-7.55 (m, 4H), 7.41-7.38 (m, 2H), 7.33-7.19 (m, 4H), 6.50 (t, J=5.6, 1H), 4.53 (d, J=5.5, 2H), 4.27 (s, 2H), 3.66 (t, J=5.7, 2H), 2.52-2.45 (m, 2H).

Example 140

Preparation of N-(3,4-difluorophenyl)-4-oxo-3-phenyl-2-[(pyridin-3-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.90 (s, 1H), 8.47 (d, J=1.9, 1H), 8.41 (m, 1H), 7.68-7.50 (m, 5H), 7.34-7.24 (m, 5H), 6.58 (t, J=5.7, 1H), 4.43 (d, J=5.6, 2H), 4.23 (s, 2H), 3.67 (t, J=5.5, 2H), 2.52-2.45 (m, 2H).

Example 141

Preparation of N-(3,4-difluorophenyl)-4-oxo-3-phenyl-2-[(pyridin-4-ylmethylbenzyl)amino]-3,5,7,8-tetrahydropyrido[4,3-d]-pyrimidine-6(4H)-carboxamide $^1$H-NMR (300 MHz, DMSO-d$_6$): δ (ppm)=8.89 (s, 1H), 8.46 (d, J=6.0, 2H), 7.65-7.54 (m, 4H), 7.40-7.33 (m, 2H), 7.30-7.21 (m, 4H), 6.58 (t, J=5.9, 1H), 4.44 (d, J=5.8, 2H), 4.23 (s, 2H), 3.65 (t, J=5.4, 2H), 2.45 (t, J=5.3, 2H).

Example 142

Preparation of N-(3,4-difluorophenyl)-2-[(3-dimethyl-methylaminobenzyl)amino]-4-oxo-3-phenyl-3,5,7,8-tetrahydropyrido-[4,3-d]pyrimidine-6(4H)-carboxamide $^1$H-NMR (300 MHz, DMSO-d$_6$): δ (ppm)=8.90 (s, 1H), 7.66-7.51 (m, 4H), 7.33-7.25 (m, 4H), 7.07 (t, J=7.8, 1H), 6.59-6.51 (m, 3H), 6.33 (t, J=6.1, 1H), 4.38 (d, J=5.6, 2H), 4.23 (s, 2H), 3.67 (t, J=5.5, 2H), 2.86 (s, 6H), 2.52-2.45 (m, 2H).

Example 143

Preparation of N-(3,4-difluorophenyl)-2-[(3-acetylaminobenzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=9.84 (s, 1H), 8.89 (s, 1H), 7.66-7.50 (m, 4H), 7.48 (s, 1H), 7.42-7.30 (m, 3H), 7.27-7.23 (m, 2H), 7.18 (t, J=7.8, 1H), 6.88 (d, J=7.7, 1H), 6.47 (t, J=5.9, 1H), 4.41 (d, J=5.7, 2H), 4.23 (s, 2H), 3.66 (t, J=5.4, 2H), 2.52-2.45 (m, 2H), 2.03 (s, 3H).

Example 144

Preparation of N-(3,4-difluorophenyl)-2-[(3-carboxybenzyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=12.88 (br s, 1H), 8.89 (s, 1H), 7.87 (s, 1H), 7.78 (d, J=7.7, 1H), 7.68-7.50 (m, 5H), 7.41 (t, J=7.7, 1H), 7.35-7.23 (m, 4H), 6.59 (t, J=5.9, 1H), 4.47 (d, J=5.8, 2H), 4.23 (s, 2H), 3.66 (app t, 2H).

Example 145

Preparation of N-(3,4-difluorophenyl)-2-[(benzo[1,3]dioxo-5-ylmethyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=8.90 (s, 1H), 7.65-7.50 (m, 4H), 7.33-7.22 (m, 4H), 6.81 (d, J=8.8, 2H), 6.72 (app d, 1H), 6.39 (t, J=5.9, 1H), 5.95 (s, 2H), 4.32 (d, J=5.7, 2H), 4.22 (s, 2H), 3.67 (t, J=5.4, 2H).

Example 146

Preparation of N-(3,4-difluorophenyl)-2-[(4-methoxyphenyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=8.91 (s, 1H), 7.70-7.50 (m, 4H), 7.46 (s, 1H), 7.39 (d, J=8.3, 2H), 7.35-7.20 (m, 4H), 6.84 (d, J=9.0, 2H), 4.26 (s, 2H), 3.72 (s, 3H), 3.67 (t, J=5.4, 2H).

Example 147

Preparation of N-(3,4-difluorophenyl)-4-oxo-3-phenyl-2-phenylamino-3,5,7,8-tetrahydropyrido[4,3-d]pyrimidine-6(4H)-carboxamide $^1$H-NMR (300 MHz, DMSO-d$_6$): δ (ppm)=8.92 (s, 1H), 7.70-7.50 (m, 5H), 7.48-7.38 (m, 4H), 7.36-7.20 (m, 4H), 7.09 (t, J=7.3, 1H), 4.28 (s, 2H), 3.69 (t, J=5.5, 2H).

Example 148

Preparation of N-(3,4-difluorophenyl)-4-oxo-3-phenyl-2-[(thiophen-2-ylmethyl)amino]-3,5,7,8-tetrahydropyrido[4,3-d]-pyrimidine-6(4H)-carboxamide $^1$H-NMR (300 MHz, DMSO-d$_6$): δ (ppm)=8.91 (s, 1H), 7.70-7.50 (m, 4H), 7.49-7.21 (m, 5H), 6.98-6.86 (m, 2H), 6.58 (t, J=5.9, 1H), 4.55 (d, J=5.6, 2H), 4.24 (s, 2H), 3.70 (t, J=5.5, 2H), 2.68-2.55 (m, 2H).

Example 149

Preparation of N-(3,4-difluorophenyl)-2-[(furan-2-ylmethyl)amino]-4-oxo-3-phenyl-3,5,7,8-tetrahydropyrido[4,3-d]-pyrimidine-6(4H)-carboxamide $^1$H-NMR (300 MHz, DMSO-d$_6$): δ (ppm)=8.91 (s, 1H), 7.70-7.50 (m, 5H), 7.36-7.22 (m, 4H), 6.41-6.32 (m, 2H), 6.24-6.16 (m, 1H), 4.40 (d, J=5.6, 2H), 4.24 (s, 2H), 3.68 (t, J=5.5, 2H).

Example 150

Preparation of N-(3,4-difluorophenyl)-2-cyclohexylamino-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.70-7.50 (m, 4H), 7.37-7.22 (m, 4H), 4.95 (d, J=8.1, 1H), 4.23 (s, 2H), 3.95-3.80 (m, 1H), 3.68 (t, J=5.5, 2H), 1.80-1.65 (m, 2H), 1.60-1.42 (m, 3H), 1.35-1.00 (m, 5H).

Example 151

Preparation of N-(3,4-difluorophenyl)-2-(tert-butylamino)-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.91 (s, 1H), 7.70-7.50 (m, 4H), 7.40-7.30 (m, 2H), 7.27 (d, J=6.8, 2H), 4.25 (s, 2H), 4.10 (s, 1H), 3.70 (t, J=5.7, 2H), 1.28 (s, 9H).

Example 152

Preparation of N-(3,4-difluorophenyl)-2-[(cyclohexylmethyl)amino]-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.90 (s, 1H), 7.70-7.50 (m, 4H), 7.40-7.22 (m, 4H), 5.66 (t, J=5.5, 1H), 4.23 (s, 2H), 3.68 (t, J=5.5, 2H), 3.07 (t, J=5.6, 2H), 2H overlapped with DMSO-signal, 1.72-1.45 (m, 6H), 1.25-1.05 (m, 3H), 0.90-0.70 (m, 2H).

Example 153

Preparation of N-(3,4-difluorophenyl)-2-(2,2-dimethylpropylamino)-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.91 (s, 1H), 7.70-7.50 (m, 4H), 7.40-7.20 (m, 4H), 5.11 (t, J=6.0, 1H), 4.24 (s, 2H), 3.68 (t, J=5.4, 2H), 3.12 (d, J=6.0, 2H), 0.75 (s, 9H).

Example 154

Preparation of N-(3,4-difluorophenyl)-4-oxo-3-phenyl-2-(n-propylamino)-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.70-7.50 (m, 4H), 7.36-7.20 (m, 4H), 5.77 (t, J=5.6, 1H), 4.23 (s, 2H), 3.68 (t, J=5.6, 2H), 3.17 (q, J=6.5, 2H), 1.45 (sixtet, J=7.3, 2H), 0.76 (t, J=7.4, 3H).

Example 155

Preparation of N-(3,4-difluorophenyl)-4-oxo-3-phenyl-2-(piperidin-1-yl)-3,5,7,8-tetrahydropyrido[4,3-d]pyrimidine-6(4H)-carboxamide $^1$H-NMR (300 MHz, DMSO-$d_6$): δ (ppm)=8.93 (s, 1H), 7.70-7.20 (m, 8H), 4.27 (s, 2H), 3.70 (t, J=5.6, 2H), 3.02-2.95 (m, 4H), 2.60 (t, J=5.4, 2H), 1.40-1.25 (m, 2H), 1.22-1.10 (m, 4H).

Example 156

Preparation of N-(3,4-difluorophenyl)-2-(3,4-dihydro-1H-isoquinolin-2-yl)-4-oxo-3-phenyl-3,5,7,8-tetrahydropyrido[4,3-d]-pyrimidine-6(4H)-carboxamide $^1$H-NMR (300 MHz, DMSO-$d_6$): δ (ppm)=8.95 (s, 1H), 7.70-7.60 (m, 1H), 7.58-7.40 (m, 5H), 7.38-7.22 (m, 2H), 7.18-7.05 (m, 3H), 7.02-6.92 (m, 1H), 4.30 (s, 4H), 3.73 (t, J=5.5, 2H), 3.20 (t, J=5.5, 2H), 2.70-2.60 (m, 2H), 2.20-2.10 (m, 2H).

Example 157

Preparation of N-(3,4-difluorophenyl)-2-(benzylmethylamino)-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.94 (s, 1H), 7.70-7.60 (m, 1H), 7.55-7.35 (m, 5H), 7.33-7.20 (m, 5H), 7.18-7.02 (m, 2H), 4.29 (s, 4H), 3.71 (t, J=5.5, 2H), 2.68-2.58 (m, 2H), 2.31 (s, 3H).

Example 158

Preparation of N-(3,4-difluorophenyl)-4-oxo-2-phenethylamino-3-phenyl-3,5,7,8-tetrahydropyrido[4,3-d]pyrimidine-6(4H)-carboxamide $^1$H-NMR (300 MHz, DMSO-$d_6$): δ (ppm)=8.91 (s, 1H), 7.70-7.50 (m, 4H), 7.38-7.10 (m, 9H), 5.71 (t, J=5.5, 1H), 4.24 (s, 2H), 3.70 (t, J=5.6, 2H), 3.50-3.38 (m, 2H), 2.75 (t, J=7.2, 2H), 2.62-2.56 (m, 2H).

Example 159

Preparation of N-(3,4-difluorophenyl)-2-[(3-aminobenzyl)-amino]-4-oxo-3-phenyl-3,5,7,8-tetrahydropyrido[4,3-d]pyrimidine-6(4H)-carboxamide $^1$H-NMR (300 MHz, DMSO-$d_6$): δ (ppm)=8.90 (s, 1H), 7.62-7.52 (m, 4H), 7.35-7.25 (m, 4H), 6.90 (t, J=7.7, 1H), 6.42-6.33 (m, 3H), 6.28 (t, J=5.8, 1H), 4.97 (s, 2H), 4.31 (d, J=5.8, 2H), 4.24 (s, 2H), 3.67 (t, J=5.3, 2H), 2.52-2.45 (m, 2H).

Example 160

Preparation of N-(2,4-dichlorophenyl)-2-[(4-methoxybenzyl)amino]-4-oxo-3-phenyl-3,5,7,8-tetrahydropyrido[4,3-d]-pyrimidine-6(4H)-carbothioamide

[Chemical formula 31]

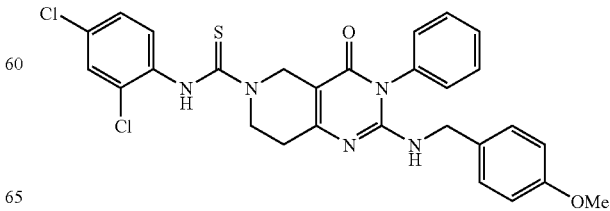

$^1$H-NMR (400 MHz, CDCl$_3$): δ (ppm)=7.77 (d, J=8.0, 1H), 7.48-7.59 (m, 4H), 7.40 (d, J=4.0, 1H), 7.32 (s, 1H), 7.24 (dd, J=8.0, 4.0, 2H), 7.13 (d, J=8.0, 2H), 6.83 (d, J=8.0, 2H), 4.57 (s, 2H), 4.50 (d, J=4.0, 2H), 4.45-4.38 (m, 3H), 3.78 (s, 3H), 2.48 (t, J=4.0, 2H).

Example 161

Preparation of N-(3,4-difluorophenyl)-2-[(4-methoxybenzyl)amino]-4-oxo-3-phenyl-3,5,7,8-tetrahydropyrido[4,3-d]-pyrimidine-6(4H)-carbothioamide $^1$H-NMR (400 MHz, CDCl$_3$): δ (ppm)=7.58-7.48 (m, 4H), 7.22 (d, J=8.0, 2H), 7.18 (m, 4H), 6.94-6.89 (m, 1H), 6.83 (d, J=8.0, 2H), 4.49 (d, J=8.0, 4H), 4.57 (q, J=4.0, 1H), 4.38 (t, J=4.0, 2H), 3.78 (s, 3H), 2.82 (t, J=8.0, 2H).

Example 162

Preparation of N-(4-chlorophenyl)-2-[(4-methoxybenzyl)-amino]-4-oxo-3-phenyl-3,5,6,8-tetrahydropyrido[3,4-d]pyrimidine-7(4H)-carboxamide The compound obtained in Reference Example 6 and 4-chloro-phenyl isocyanate were reacted and treated in a similar manner to Example 1 to give the title compound.

MS-APCI: m/z: 516, 518 ([M+H]$^+$).

$^1$H-NMR (300 MHz, DMSO-d$_6$): δ (ppm)=8.75 (s, 1H), 7.60-7.49 (m, 7H), 7.27 (dd, J=1.9, 9.0, 2H), 7.18 (d, J=8.7, 2H), 6.84 (d, J=8.7, 2H), 6.38 (t, J=6.0, 1H), 4.35 (d, J=5.9, 2H), 4.27 (s, 2H), 3.71 (s, 3H), 3.64 (t, J=5.6, 2H), 2.37 (t, J=5.7, 2H).

Example 163

Preparation of 6-(4-chlorobenzoyl)-2-[(4-methoxybenzyl)-amino]-3-phenyl-5,6,7,8-tetrahydropyrido[4,3-d]pyrimidin-4(3H)-one To a solution of the compound obtained in Reference Example 6 (0.1 g) in methylene chloride (2 ml) were added 4-chlorobenzoyl chloride (32 µl) and diisopropylethylamine (197 µl), and the mixture was stirred at room temperature for 2 hours. The reaction mixture was diluted with chloroform, and washed with a saturated aqueous sodium hydrogen carbonate solution. The organic layer was dried over anhydrous sodium sulfate, and concentrated under reduced pressure. The obtained residue was purified by preparative reverse-phase column chromatography to give the title compound (105 mg).

MS-APCI: m/z: 501, 503 ([M+H]$^+$).

The compounds of Examples 164 and 165 were obtained by reacting and treating according to the process of Example 163.

Example 164

Preparation of 6-(benzo[b]thiophen-2-carbonyl)-2-[(4-methoxybenzyl)amino]-3-phenyl-5,6,7,8-tetrahydropyrido[4,3-d]-pyrimidin-4(3H)-one MS-APCI: m/z: 523 ([M+H]$^+$).

Example 165

Preparation of 2-[(4-methoxybenzyl)amino]-6-[(E)-3-(4-methoxyphenyl)-acryloyl)]-3-phenyl-5,6,7,8-tetrahydropyrido[4,3-d]-pyrimidin-4(3H)-one MS-APCI: m/z: 523 ([M+H]$^+$).

Example 166

Preparation of 6-[(4-tert-butylbenzene)sulfonyl]-2-[(4-methoxybenzyl)amino]-3-phenyl-5,6,7,8-tetrahydropyrido[4,3-d]-pyrimidin-4(3H)-one To a solution of the compound obtained in Reference Example 6 (0.1 g) in methylene chloride (2 ml) were added 4-tert-butyl benzenesulfonylchloride (59 mg) and diisopropylethylamine (197 µl), and the mixture was stirred at room temperature overnight. The reaction mixture was diluted with chloroform, and washed with a saturated aqueous sodium hydrogen carbonate solution. The organic layer was dried over anhydrous sodium sulfate and concentrated under reduced pressure. The obtained residue was purified by preparative reverse-phase column chromatography to give the title compound (95 mg).

MS-APCI: m/z: 559 ([M+H]$^+$).

$^1$H-NMR (300 MHz, DMSO-d$_6$): δ (ppm)=8.75 (s, 1H), 7.60-7.49 (m, 7H), 7.27 (dd, J=1.9, 9.0, 2H), 7.18 (d, J=8.7, 2H), 6.84 (d, J=8.7, 2H), 6.38 (t, J=6.0, 1H), 4.35 (d, J=5.9, 2H), 4.27 (s, 2H), 3.71 (s, 3H), 3.64 (t, J=5.6, 2H), 2.37 (t, J=5.7, 2H).

Example 167

Preparation of N-(3-chlorophenyl)-2-(methylthio)-4-oxo-3-phenyl-3,5,7,8-tetrahydropyrido[4,3-d]pyrimidine-6(4H)-carboxamide The compound obtained in Reference Example 13 and 3-chlorophenylisocyanate were reacted and treated in a similar manner to Example 1 to give the title compound.

MS-APCI: m/z: 427, 429 ([M+H]$^+$).

Example 168

Preparation of N-(2,4-dichlorophenyl)-2-(benzylthio)-4-oxo-3-phenyl-3,5,7,8-tetrahydropyrido[4,3-d]pyrimidine-6(4H)-carboxamide The compound obtained in Reference Example 15 was reacted and treated in a similar manner to Example 1 to give the title compound.

MS-APCI: m/z: 537, 539, 541 ([M+H]$^+$).

¹H-NMR (300 MHz, DMSO-d₆): δ (ppm)=8.56 (s, 1H), 7.61 (d, J=2.4, 1H), 7.56-7.50 (m, 4H), 7.39-7.23 (m, 8H), 4.34-4.32 (m, 4H), 3.77 (t, J=5.6, 2H), 2.77 (t, J=5.2, 2H).

Example 169

Preparation of N-(3,4-difluorophenyl)-2-(benzylthio)-4-oxo-3-phenyl-3,5,7,8-tetrahydropyrido[4,3-d]pyrimidine-6(4H)-carboxamide The title compound was obtained by reacting and treating according to the process of Example 168.
¹H-NMR (300 MHz, DMSO-d₆): δ (ppm)=8.98 (s, 1H), 7.67-7.52 (m, 4H), 7.38-7.23 (m, 9H), 4.34 (s, 2H), 4.32 (s, 2H), 3.75 (t, J=5.5, 2H), 2.76 (br. t, 2H).

Example 170

Preparation of N-(2,4-dichlorophenyl)-2-[(4-methoxybenzoyl)amino]-4-oxo-3-phenyl-3,5,7,8-tetrahydropyrido[4,3-d]-pyrimidine-6(4H)-carboxamide The compound obtained in Reference Example 18 was reacted and treated in a similar manner to Example 1 to give the title compound.
¹H-NMR (300 MHz, DMSO-d₆): δ (ppm)=8.61 (s, 1H), 8.11 (d, J=8.8, 2H), 7.61 (d, J=2.4, 1H), 7.50-7.33 (m, 7H), 7.12 (d, J=8.8, 2H), 4.31 (s, 2H), 3.89 (s, 3H), 3.67 (t, J=5.8, 2H), 2.48-2.40 (m, 2H).

Example 171

Preparation of N-(3,4-difluorophenyl)-2-[(4-methoxybenzoyl)amino]-4-oxo-3-phenyl-3,5,7,8-tetrahydropyrido[4,3-d]-pyrimidine-6(4H)-carboxamide The compound of Example 171 was obtained according to the process of Example 170.
¹H-NMR (300 MHz, DMSO-d₆): δ (ppm)=9.01 (s, 1H), 8.11 (d, J=9.0, 2H), 7.64-7.56 (m, 1H), 7.50-7.19 (m, 7H), 7.11 (d, J=9.0, 2H), 4.32 (s, 2H), 3.89 (s, 3H), 3.65 (t, J=6.0, 2H), 2.48-2.40 (m, 2H).

INDUSTRIAL APPLICABILITY

The compound of the present invention and a pharmaceutically acceptable salt thereof have MGAT inhibitory activity, and are useful as an agent for treatment or prophylaxis of adiposity, metabolic syndromes, hyperlipidemia, hyper neutral lipemia, hyper VLDL-mia, hyper fatty acidemia, diabetes mellitus, and arteriosclerosis.

The invention claimed is:

1. A compound having a bicyclic pyrimidine structure of the following formula (I) or a pharmaceutically acceptable salt thereof:

[Chemical formula 1]

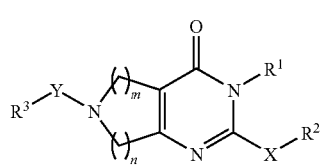

(I)

wherein $R^1$ is an optionally substituted cyclic lower alkyl group, an optionally substituted cyclic lower alkenyl group, an optionally substituted phenyl group, an optionally substituted naphthyl group, or a saturated or unsaturated optionally substituted heterocyclic group, $R^2$ is a hydrogen atom, an optionally substituted lower alkyl group, an optionally substituted lower alkenyl group, an optionally substituted lower alkynyl group, an optionally substituted cyclic lower alkyl group, an optionally substituted cyclic lower alkenyl group, an optionally substituted lower alkanoyl group, an optionally substituted phenylcarbonyl group, an optionally substituted phenyl group, or an optionally substituted naphthyl group, $R^3$ is a hydrogen atom, an optionally substituted lower alkyl group, an optionally substituted lower alkenyl group, an optionally substituted lower alkynyl group, an optionally substituted cyclic lower alkyl group, an optionally substituted cyclic lower alkenyl group, an optionally substituted phenyl group, or an optionally substituted naphthyl group, X is an oxygen atom, a sulfur atom, or —N($R^4$)—, $R^4$ is a hydrogen atom or a lower alkyl group, or $R^2$ and $R^4$ may combine each other to form a cyclic amino group, Y is the following (II), (III) or (IV):

[Chemical formula 2]

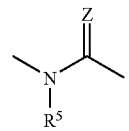

(II)

(III)

(IV)

$R^5$ is a hydrogen atom or a lower alkyl group,

Z is an oxygen atom or a sulfur atom, and m and n are each an integer of 1 or 2.

2. The compound according to claim 1 or a pharmaceutically acceptable salt thereof, wherein X is a sulfur atom or —N($R^4$)— ($R^4$ is the same as defined in claim 1).

3. The compound according to claim 1 or a pharmaceutically acceptable salt thereof, wherein Y is the following (II) or (III):

[Chemical formula 3]

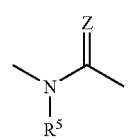

(II)

-continued

(III)

($R^5$ and Z are the same as defined in claim 1).

4. The compound according to claim 1 or a pharmaceutically acceptable salt thereof, wherein in the formula (I), $R^1$ is a cyclic $C_{3-8}$ alkyl group, a cyclic $C_{3-8}$ alkenyl group, a phenyl group, a naphthyl group, or a saturated or unsaturated heterocyclic group, $R^2$ is a hydrogen atom, a $C_{1-8}$ alkyl group, a $C_{2-8}$ alkenyl group, a $C_{2-8}$ alkynyl group, a cyclic $C_{3-8}$ alkyl group, a cyclic $C_{3-8}$ alkenyl group, a $C_{1-8}$ alkanoyl group, a phenylcarbonyl group, a phenyl group, or a naphthyl group, $R^3$ is a hydrogen atom, a $C_{1-8}$ alkyl group, a $C_{2-8}$ alkenyl group, a $C_{2-8}$ alkynyl group, a cyclic $C_{3-8}$ alkyl group, a cyclic $C_{3-8}$ alkenyl group, a phenyl group, or a naphthyl group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 4]

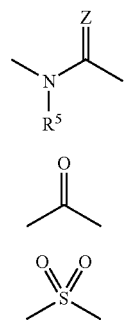

$R^5$ is a hydrogen atom or a $C_{1-8}$ alkyl group,

Z is an oxygen atom or a sulfur atom, m and n are an integer of 1 or 2, in which the above-mentioned alkyl, alkenyl, alkynyl and alkanoyl groups for $R^2$ and $R^3$ may be substituted by 1 to 3 substituents selected from a halogen atom, a cyclic $C_{3-8}$ alkyl group, a phenyl group, a phenyloxy group, a $C_{1-8}$ alkoxy group, a trifluoromethoxy group, a $C_{1-8}$ alkylthio group, a hydroxy group, a nitro group, a cyano group, a carboxyl group, a $C_{1-8}$ alkoxycarbonyl group, a benzyloxycarbonyl group, a carbamoyl group, a mono- or di-substituted $C_{1-8}$ alkylaminocarbonyl group, a cyclic aminocarbonyl group, an amino group, a mono- or di-substituted $C_{1-8}$ alkylamino group, a cyclic amino group, a $C_{1-8}$ alkylsulfonylamino group, a benzenesulfonylamino group, a $C_{1-8}$ alkanoylamino group, a benzoylamino group, a $C_{1-8}$ alkoxycarbonylamino group, a carbamoylamino group, a mono- or di-substituted $C_{1-8}$ alkylaminocarbonylamino group, a cyclic aminocarbonylamino group, a sulfamoyl group, a mono- or di-substituted $C_{1-8}$ alkylaminosulfonyl group, a cyclic aminosulfonyl group and a saturated or unsaturated heterocyclic group, when the above-mentioned alkyl group for $R^2$ and $R^3$ is substituted by a phenyl group, then said phenyl group may further be substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a $C_{1-8}$ alkylthio group, a nitro group, a cyano group, a carboxyl group, a $C_{1-8}$ alkoxycarbonyl group, a carbamoyl group, an amino group, a mono- or di-substituted $C_{1-8}$ alkylamino group, a $C_{1-8}$ alkanoylamino group, a carbamoylamino group and a sulfamoyl group, the above-mentioned cyclic alkyl, cyclic alkenyl, phenylcarbonyl, phenyl, naphthyl and saturated or unsaturated heterocyclic groups for $R^1$ may be substituted by 1 to 3 substituents selected from a halogen atom, a $C_{1-8}$ alkyl group, a cyclic $C_{3-8}$ alkyl group, a phenyl group, a phenyloxy group, a $C_{1-8}$ alkoxy group, a trifluoromethyl group, a trifluoromethoxy group, a $C_{1-8}$ alkylthio group, a hydroxy group, a hydroxy-$C_{1-8}$ alkyl group, a nitro group, a cyano group, a carboxyl group, a $C_{1-8}$ alkoxycarbonyl group, a benzyloxycarbonyl group, a carbamoyl group, a mono- or di-substituted $C_{1-8}$ alkylaminocarbonyl group, a cyclic aminocarbonyl group, an amino group, a mono- or di-substituted $C_{1-8}$ alkylamino group, a cyclic amino group, a $C_{1-8}$ alkylsulfonylamino group, a benzenesulfonylamino group, a $C_{1-8}$ alkanoylamino group, a benzoylamino group, a $C_{1-8}$ alkoxycarbonylamino group, a carbamoylamino group, a mono- or di-substituted $C_{1-8}$ alkylaminocarbonylamino group, a cyclic aminocarbonylamino group, a sulfamoyl group, a mono- or di-substituted $C_{1-8}$ alkylaminosulfonyl group and a cyclic aminosulfonyl group, and the above-mentioned cyclic alkyl, cyclic alkenyl, phenylcarbonyl, phenyl and naphthyl groups for $R^2$ and $R^3$ may be substituted by 1 to 3 substituents selected from a halogen atom, a $C_{1-8}$ alkyl group, a cyclic $C_{3-8}$ alkyl group, a phenyl group, a phenyloxy group, a $C_{1-8}$ alkoxy group, a trifluoromethyl group, a trifluoromethoxy group, a $C_{1-8}$ alkylthio group, a hydroxy group, a hydroxy-$C_{1-8}$ alkyl group, a nitro group, a cyano group, a carboxyl group, a $C_{1-8}$ alkoxycarbonyl group, a benzyloxycarbonyl group, a carbamoyl group, a mono- or di-substituted $C_{1-8}$ alkylaminocarbonyl group, a cyclic aminocarbonyl group, an amino group, a mono- or di-substituted $C_{1-8}$ alkylamino group, a cyclic amino group, a $C_{1-8}$ alkylsulfonylamino group, a benzenesulfonylamino group, a $C_{1-8}$ alkanoylamino group, a benzoylamino group, a $C_{1-8}$ alkoxycarbonylamino group, a carbamoylamino group, a mono- or di-substituted $C_{1-8}$ alkylaminocarbonylamino group, a cyclic aminocarbonylamino group, a sulfamoyl group, a mono- or di-substituted $C_{1-8}$ alkylaminosulfonyl group and a cyclic aminosulfonyl group.

5. The compound according to claim 4 or a pharmaceutically acceptable salt thereof, wherein in the formula (I), $R^1$ is a cyclic $C_{3-8}$ alkyl group, a cyclic $C_{3-8}$ alkenyl group, a phenyl group, or a saturated or unsaturated heterocyclic group, $R^2$ is a $C_{1-8}$ alkyl group, a cyclic $C_{3-8}$ alkyl group, or a phenyl group, $R^3$ is a $C_{1-8}$ alkyl group, a $C_{2-8}$ alkenyl group, a cyclic $C_{3-8}$ alkyl group, a cyclic $C_{3-8}$ alkenyl group, or a phenyl group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 5]

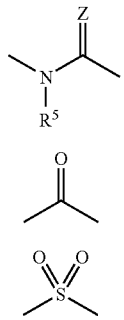

(II)

(III)

(IV)

$R^5$ is a hydrogen atom or a $C_{1-8}$ alkyl group,

Z is an oxygen atom or a sulfur atom, m and n are an integer of 1 or 2, in which the above-mentioned alkyl and alkenyl groups for $R^2$ and $R^3$ may be substituted by 1 to 3 substituents selected from a halogen atom, a phenyl group, a phenyloxy group, a $C_{1-8}$ alkoxy group, a trifluoromethoxy group, a cyano group, a carboxyl group, a carbamoyl group, an amino group, a mono- or di-substituted $C_{1-8}$ alkylamino group, a $C_{1-8}$ alkanoylamino group, a sulfamoyl group and a saturated or unsaturated heterocyclic group, when the above-mentioned alkyl group for $R^2$ and $R^3$ is substituted by a phenyl group, then said phenyl group may further be substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, the above-mentioned cyclic alkyl, cyclic alkenyl, phenyl and saturated or unsaturated heterocyclic groups for $R^1$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, and the above-mentioned cyclic alkyl, cyclic alkenyl and phenyl for $R^2$ and $R^3$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group.

6. The compound according to claim 5 or a pharmaceutically acceptable salt thereof, wherein in the formula (I), $R^1$ is a cyclic $C_{3-8}$ alkyl group, a phenyl group, or a saturated or unsaturated heterocyclic group, $R^2$ is a $C_{1-8}$ alkyl group, a cyclic $C_{3-8}$ alkyl group, or a phenyl group, $R^3$ is a $C_{1-8}$ alkyl group, a cyclic $C_{3-8}$ alkyl group, or a phenyl group, X is an oxygen atom, a sulfur atom, or —N($R^4$)—, $R^4$ is a hydrogen atom or a $C_{1-8}$ alkyl group, or $R^2$ and $R^4$ may combine each other to form a cyclic amino group, Y is the following (II), (III) or (IV):

[Chemical formula 6]

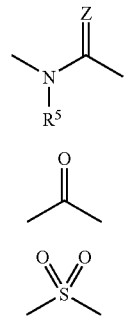

(II)

(III)

(IV)

$R^5$ is a hydrogen atom or a $C_{1-8}$ alkyl group,

Z is an oxygen atom or a sulfur atom, m and n are an integer of 1 or 2, in which the above-mentioned alkyl group for $R^2$ and $R^3$ may be substituted by 1 to 3 substituents selected from a halogen atom, a phenyl group, a phenyloxy group, a $C_{1-8}$ alkoxy group, a trifluoromethoxy group, a cyano group, a carboxyl group, a carbamoyl group, an amino group, a mono- or di-substituted $C_{1-8}$ alkylamino group, a $C_{1-8}$ alkanoylamino group, a sulfamoyl group and a saturated or unsaturated heterocyclic group, when the above-mentioned alkyl group for $R^2$ and $R^3$ is substituted by a phenyl group, then said phenyl group may further be substituted by 1 to 3 substituents selected from a halogen atom, a $C_{1-8}$ alkyl group, a phenyl group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, the above-mentioned cyclic alkyl, phenyl and saturated or unsaturated heterocyclic groups for $R^1$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group, and the above-mentioned cyclic alkyl and phenyl for $R^2$ and $R^3$ may be substituted by 1 to 3 substituents selected from a halogen atom, a $C_{1-8}$ alkyl group, a phenyl group, a phenyloxy group, a $C_{1-8}$ alkoxy group, a trifluoromethyl group, a trifluoromethoxy group, a cyano group, a carboxyl group, a carbamoyl group, an amino group, a mono- or di-substituted $C_{1-8}$ alkylamino group, a $C_{1-8}$ alkanoylamino group and a sulfamoyl group.

7. The compound according to claim 4 or a pharmaceutically acceptable salt thereof, wherein X is a sulfur atom or —N($R^4$)— ($R^4$ is the same as defined in claim 4).

8. The compound according to claim 4 or a pharmaceutically acceptable salt thereof, wherein Y is the following (II) or (III):

[Chemical formula 7]

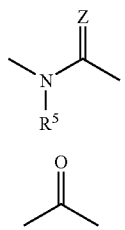
(II)

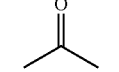
(III)

($R^5$ and Z are the same as defined in claim 4).

9. The compound according to claim 5 or a pharmaceutically acceptable salt thereof, wherein X is a sulfur atom or —N($R^4$)— ($R^4$ is the same as defined in claim 5).

10. The compound according to claim 5 or a pharmaceutically acceptable salt thereof, wherein Y is the following (II) or (III):

[Chemical formula 8]

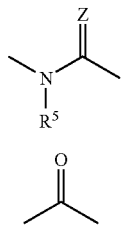
(II)

(III)

($R^5$ and Z are the same as defined in claim 5).

11. The compound according to claim 6 or a pharmaceutically acceptable salt thereof, wherein X is a sulfur atom or —N($R^4$)— ($R^4$ is the same as defined in claim 6).

12. The compound according to claim 6 or a pharmaceutically acceptable salt thereof, wherein Y is the following (II) or (III):

[Chemical formula 9]

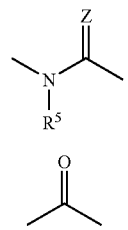
(II)

(III)

($R^5$ and Z are the same as defined in claim 6).

13. A pharmaceutical composition containing a compound as set forth in claim 1 or a pharmaceutically acceptable salt thereof.

14. A method for inhibiting monoacylglycerol acyltransferase, which comprises administering to a patient a compound as set forth in claim 1 or a pharmaceutically acceptable salt thereof.

15. A method for inhibiting fat absorption, which comprises administering to a patient a compound as set forth in claim 1 or a pharmaceutically acceptable salt thereof.

16. A method for treatment of adiposity, metabolic syndromes, hyperlipidemia, hyper neutral lipemia, hyper VLDL-mia, hyper fatty acidemia, and diabetes mellitus, which comprises administering to a patient in need thereof a compound as set forth in claim 1 or a pharmaceutically acceptable salt thereof.

* * * * *